(12) United States Patent
Harmon et al.

(10) Patent No.: US 12,421,306 B1
(45) Date of Patent: Sep. 23, 2025

(54) LUNG-TARGETING SINGLE-DOMAIN ANTIBODIES AND PURIFICATION METHODS

(71) Applicant: National Technology & Engineering Solutions of Sandia, LLC, Albuquerque, NM (US)

(72) Inventors: Brooke Nicole Harmon, Livermore, CA (US); Maxwell Stefan, Pleasanton, CA (US); Jennifer Schwedler, Livermore, CA (US); Yooli Kim Light, Pleasanton, CA (US); Catherine Margaret Mageeney, Livermore, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 204 days.

(21) Appl. No.: 17/953,930

(22) Filed: Sep. 27, 2022

(51) Int. Cl.
  *C07K 16/18* (2006.01)
  *A61K 39/00* (2006.01)
  *A61P 11/00* (2006.01)

(52) U.S. Cl.
  CPC .............. *C07K 16/18* (2013.01); *A61P 11/00* (2018.01); *A61K 2039/505* (2013.01); *C07K 2317/22* (2013.01); *C07K 2317/569* (2013.01)

(58) Field of Classification Search
  CPC ................ C07K 16/18; C07K 2317/22; C07K 2317/569; A61P 11/00; A61K 2039/505
  See application file for complete search history.

(56) References Cited

PUBLICATIONS

Mitchell, Laura S., and Lucy J. Colwell. "Analysis of nanobody paratopes reveals greater diversity than classical antibodies." Protein Engineering, Design and Selection 31.7-8 (2018): 267-275. (Year: 2018).*
Edwards, Bryan M., et al. "The remarkable flexibility of the human antibody repertoire; isolation of over one thousand different antibodies to a single protein, BLyS." Journal of molecular biology 334.1 (2003): 103-118. (Year: 2003).*
He, Xian, et al. "Identification of a nanobody specific to human pulmonary surfactant protein A." Scientific Reports 7.1 (2017): 1412. (Year: 2017).*
Kiyoshi, Masato, et al. "Affinity improvement of a therapeutic antibody by structure-based computational design: generation of electrostatic interactions in the transition state stabilizes the antibody-antigen complex." PloS one 9.1 (2014): e87099. (Year: 2014).*
Rudikoff, Stuart, et al. "Single amino acid substitution altering antigen-binding specificity." Proceedings of the National Academy of Sciences 79.6 (1982): 1979-1983. (Year: 1982).*
Bao, Guangfa, et al. "Nanobody: a promising toolkit for molecular imaging and disease therapy." EJNMMI research 11 (2021): 1-13. (Year: 2021).*
Tijink, Bernard M., et al. "Improved tumor targeting of anti-epidermal growth factor receptor Nanobodies through albumin binding: taking advantage of modular Nanobody technology." Molecular cancer therapeutics 7(8) (2008): 2288-2297. (Year: 2008).*
Henry, Kevin A., Jamshid Tanha, and Greg Hussack. "Identification of cross-reactive single-domain antibodies against serum albumin using next-generation DNA sequencing." Protein Engineering, Design and Selection 28.10 (2015): 379-383. (Year: 2015).*
Wilton, Emily E. et al.; "sdAb-DB: The Single Domain Antibody Database"; 10.1021/acssynbio.8b00407; pubs.acs.org/synthbio; ACS Synth. Biol. 2018, 7, 2480-2484.
Løset, Geir A°ge et al.; "Expanding the Versatility of Phage Display II: Improved Affinity Selection of Folded Domains on Protein VII and IX of the Filamentous Phage"; Plos One; Feb. 2011; vol. 6; Issue 2; e17433, 10 pages.
Stefan, Maxwell A. et al.; "Development of potent and effective synthetic SARS-CoV-2 neutralizing nanobodies"; https://doi.org/10.1080/19420862.2021.1958663; MABS; 2021, vol. 13, No. 1, e1958663 (13 pages).
Roovers, Rob C. et al.; "A bi-paratopic anti-EGFR nanobody efficiently inhibits solid tumour growth"; Int J Cancer. Oct. 15, 2011; 129(8): 2013-2024. doi:10.1002/ijc.26145.
Gustafson, Heather H. et al.; "Current state of in vivo panning technologies: designing specificity and affinity into the future of drug targeting"; Adv Drug Deliv Rev. May 2018; 130: 39-49. doi: 10.1016/j.addr.2018.06.015.
Mcbride, Amber A. et al.; "Pulmonary Delivery of Magnetically Targeted Nano-in-Microparticles"; Methods Mol Biol. 2017; 1530: 369-378. doi: 10.1007/978-1-4939-6646-2_23.
Franks, Teri J. et al.; "Resident Cellular Components of the Human Lung; Current Knowledge and Goals for Research on Cell Phenotyping and Function"; www.atsjournals.org; 10.1513/pats.200803-025HR; Proc. Am. Thorac. Soc.; vol. 5. pp. 763-766, 2008; Received in original form Mar. 21, 2008; accepted in final form May 16, 2008.

* cited by examiner

*Primary Examiner* — Julie Wu
*Assistant Examiner* — Bryan William Heck
(74) *Attorney, Agent, or Firm* — Eschweiler & Potashnik, LLC; Samantha Updegraff

(57) ABSTRACT

Disclosed herein are single-domain antibodies (sdABs) configured for targeting to human or mammalian lung tissue. Constructs and methods of using such sdABs are also described herein, such as methods of binding with and transporting other sdABs or other cargo with beneficial functionalities, binding to and transporting biochemical or pharmaceutical species with beneficial functionalities, and a method of treating, diagnosing, or prophylactically treating a disease, condition, or malignancy. A purification method for in vivo treatment or testing is also provided.

20 Claims, 15 Drawing Sheets
Specification includes a Sequence Listing.

| SEQ ID NO. | CDR1 | SEQ ID NO. | CDR2 | SEQ ID NO. | CDR3 | Secondary Identifier |
|---|---|---|---|---|---|---|
| 1 | GTYSITH | 26 | DWGSPSTY | 51 | LARWEQSQNVFRRSW | sanid3-1 |
| 2 | RTFQQDG | 27 | SQQQNWVY | 52 | HIQPGQVAE | sanid3-2 |
| 3 | GTFDQYT | 28 | SWSGSFAY | 53 | QLVDGKRKG | sanid3-3 |
| 4 | TFFSFQG | 29 | SFTDGSTY | 54 | HIQPGQVTP | sanid3-4 |
| 5 | GTSRSYH | 30 | GGTGGNGW | 55 | THFNWQNVR | sanid3-5 |
| 6 | FAYSIDI | 31 | SWRGGPSK | 56 | LTVDKGGSI | sanid3-6 |
| 7 | STFQYSD | 32 | STRGHWTY | 57 | NIQVNQFSD | sanid3-7 |
| 8 | STFSGYH | 33 | RSSGTFTY | 58 | ESADWIVPN | sanid3-8 |
| 9 | GPFSGYD | 34 | STSAHWTY | 59 | FWEWRATNH | sanid3-9 |
| 10 | RTFTAVW | 35 | RTSGDWAH | 60 | HVRPGGPHI | sanid3-10 |
| 11 | RTFDTWD | 36 | SRSGNWTY | 61 | PNLQCNIQI | sanid3-11 |
| 12 | QTFSQFT | 37 | ASSGKSTD | 62 | GKTHNSAKF | sanid3-12 |
| 13 | GADGEYS | 38 | SATGSFTY | 63 | FPLHDQGGGKKL | sanid3-13 |
| 14 | RISSDYD | 39 | RRTSQWTY | 64 | WFGSLLGLF | sanid3-14 |
| 15 | GTFREYQ | 40 | AGQGHATY | 65 | SYRWDTSSTQPE | sanid3-15 |
| 16 | QFFSIST | 41 | SWRDKTTH | 66 | VKATTGRSF | sanid3-16 |
| 17 | RIFSHYR | 42 | HQSQHTQY | 67 | VRTDNGEYY | sanid3-17 |
| 18 | GTYQIYS | 43 | SWTGFSTY | 68 | DFGRAYNGQVNV | sanid3-18 |
| 19 | QTSTFQP | 44 | SRYGQSYY | 69 | VLHNTNQSEDIDYTQ | sanid3-19 |
| 20 | QPFGIYG | 45 | SRQGFTVQ | 70 | VLQWQTADV | sanid3-20 |
| 21 | RSFSDYI | 46 | SRTAWWAW | 71 | FEQNIDTWY | sanid3-21 |
| 22 | TTFQRSD | 47 | QAAQGWTY | 72 | FVAASGIST | sanid3-22 |
| 23 | RAFGIYR | 48 | GSDGGHVL | 73 | KWNHDKDHESRI | sanid3-23 |
| 24 | FSFRYYG | 49 | HQSGGWTY | 74 | VLQTTEQKIFEDYIN | sanid3-24 |
| 25 | RADSWQD | 50 | QRAQHWTY | 75 | RLPAFSGNARSPYDN | sanid3-25 |

*Fig. 3*

*Fig. 4*

| SEQ ID NO. | Full Nanobody: FR1-CDR1-FR2-CDR2-FR3-CDR3-FR4 | Secondary Identifier |
|---|---|---|
| 76 | EVQLQASGGGFVQPGGSLRLSCAASGGTYSITHMGWFRQAPGKEREFVSAISDWGSPSTYYADSVKGRFTISRDNSKNTVYLQMNSLRAEDTATYYCALARWEQSQNVFRRSWYWGQGTQVTVSS | sanid3-1 |
| 77 | EVQLQASGGGFVQPGGSLRLSCAASGRTFQQDGMGWFRQAPGKEREFVSAISSQQQNWVYYADSVKGRFTISRDNSKNTVYLQMNSLRAEDTATYYCAHIQPGQVAEYWGQGTQVTVSS | sanid3-2 |
| 78 | EVQLQASGGGFVQPGGSLRLSCAASGGTFDQYTMGWFRQAPGKEREFVSAISSWSGSFAYYADSVKGRFTISRDNSKNTVYLQMNSLRAEDTATYYCAQLVDGKRKGYWGQGTQVTVSS | sanid3-3 |
| 79 | EVQLQASGGGFVQPGGSLRLSCAASGTFFSFQGMGWFRQAPGKEREFVSAISSFTDGSTYYADSVKGRFTISRDNSKNTVYLQMNSLRAEDTATYYCAHIQPGQVTPYWGQGTQVTVSS | sanid3-4 |
| 80 | EVQLQASGGGFVQPGGSLRLSCAASGGTSRSYHMGWFRQAPGKEREFVSAISGGTGGNGWYADSVKGRFTISRDNSKNTVYLQMNSLRAEDTATYYCATHFNWQNVRYWGQGTQVTVSS | sanid3-5 |
| 81 | EVQLQASGGGFVQPGGSLRLSCAASGFAYSIDIMGWFRQAPGKEREFVSAISSWRGGPSKYADSVKGRFTISRDNSKNTVYLQMNSLRAEDTATYYCALTVDKGGSIYWGQGTQVTVSS | sanid3-6 |
| 82 | EVQLQASGGGFVQPGGSLRLSCAASGSTFQYSDMGWFRQAPGKEREFVSAISSTRGHWTYYADSVKGRFTISRDNSKNTVYLQMNSLRAEDTATYYCANIQVNQFSDYWGQGTQVTVSS | sanid3-7 |
| 83 | EVQLQASGGGFVQPGGSLRLSCAASGSTFSGYHMGWFRQAPGKEREFVSAISRSSGTFTYYADSVKGRFTISRDNSKNTVYLQMNSLRAEDTATYYCAESADWIVPNYWGQGTQVTVSS | sanid3-8 |
| 84 | EVQLQASGGGFVQPGGSLRLSCAASGGPFSGYDMGWFRQAPGKEREFVSAISSTSAHWTYYADSVKGRFTISRDNSKNTVYLQMNSLRAEDTATYYCAFWEWRATNHYWGQGTQVTVSS | sanid3-9 |
| 85 | EVQLQASGGGFVQPGGSLRLSCAASGRTFTAVWMGWFRQAPGKEREFVSAISRTSGDWAHYADSVKGRFTISRDNSKNTVYLQMNSLRAEDTATYYCAHVRPGGPHIYWGQGTQVTVSS | sanid3-10 |
| 86 | EVQLQASGGGFVQPGGSLRLSCAASGRTFDTWDMGWFRQAPGKEREFVSAISSRSGNWTYYADSVKGRFTISRDNSKNTVYLQMNSLRAEDTATYYCAPNLQCNIQIYWGQGTQVTVSS | sanid3-11 |
| 87 | EVQLQASGGGFVQPGGSLRLSCAASGQTFSQFTMGWFRQAPGKEREFVSAISASSGKSTDYADSVKGRFTISRDNSKNTVYLQMNSLRAEDTATYYCAGKTHNSAKFYWGQGTQVTVSS | sanid3-12 |
| 88 | EVQLQASGGGFVQPGGSLRLSCAASGGADGEYSMGWFRQAPGKEREFVSAISSATGSFTYYADSVKGRFTISRDNSKNTVYLQMNSLRAEDTATYYCAFPLHDQGGGKKLYWGQGTQVTVSS | sanid3-13 |
| 89 | EVQLQASGGGFVQPGGSLRLSCAASGRISSDYDMGWFRQAPGKEREFVSAISRRTSQWTYYADSVKGRFTISRDNSKNTVYLQMNSLRAEDTATYYCAWFGSLLGLFYWGQGTQVTVSS | sanid3-14 |
| 90 | EVQLQASGGGFVQPGGSLRLSCAASGGTFREYQMGWFRQAPGKEREFVSAISAGQGHATYYADSVKGRFTISRDNSKNTVYLQMNSLRAEDTATYYCASYRWDTSSTQPEYWGQGTQVTVSS | sanid3-15 |

*Fig. 5*

| 91 | EVQLQASGGGFVQPGGSLRLSCAASGQFFSISTMGWFRQAPGKEREF VSAISSWRDKTTHYADSVKGRFTISRDNSKNTVYLQMNSLRAEDTATYY CAVKATTGRSFYWGQGTQVTVSS | sanid3-16 |
|---|---|---|
| 92 | EVQLQASGGGFVQPGGSLRLSCAASGRIFSHYRMGWFRQAPGKEREF VSAISHQSQHTQYYADSVKGRFTISRDNSKNTVYLQMNSLRAEDTATYY CAVRTDNGEYYYWGQGTQVTVSS | sanid3-17 |
| 93 | EVQLQASGGGFVQPGGSLRLSCAASGGTYQIYSMGWFRQAPGKEREF VSAISSWTGFSTYYADSVKGRFTISRDNSKNTVYLQMNSLRAEDTATYY CADFGRAYNGQVNVYWGQGTQVTVSS | sanid3-18 |
| 94 | EVQLQASGGGFVQPGGSLRLSCAASGQTSTFQPMGWFRQAPGKEREF VSAISSRYGQSYYYADSVKGRFTISRDNSKNTVYLQMNSLRAEDTATYY CAVLHNTNQSEDIDYTQYWGQGTQVTVSS | sanid3-19 |
| 95 | EVQLQASGGGFVQPGGSLRLSCAASGQPFGIYGMGWFRQAPGKEREF VSAISSRQGFTVQYADSVKGRFTISRDNSKNTVYLQMNSLRAEDTATYY CAVLQWQTADVYWGQGTQVTVSS | sanid3-20 |
| 96 | EVQLQASGGGFVQPGGSLRLSCAASGRSFSDYIMGWFRQAPGKEREF VSAISSRTAWWAWYADSVKGRFTISRDNSKNTVYLQMNSLRAEDTATYY CAFEQNIDTWYYWGQGTQVTVSS | sanid3-21 |
| 97 | EVQLQASGGGFVQPGGSLRLSCAASGTTFQRSDMGWFRQAPGKEREF VSAISQAAQGWTYYADSVKGRFTISRDNSKNTVYLQMNSLRAEDTATYY CAFVAASGISTYWGQGTQVTVSS | sanid3-22 |
| 98 | EVQLQASGGGFVQPGGSLRLSCAASGRAFGIYRMGWFRQAPGKEREF VSAISGSDGGHVLYADSVKGRFTISRDNSKNTVYLQMNSLRAEDTATYY CAKWNHDKDHESRIYWGQGTQVTVSS | sanid3-23 |
| 99 | EVQLQASGGGFVQPGGSLRLSCAASGFSFRYYGMGWFRQAPGKEREF VSAISHQSGGWTYYADSVKGRFTISRDNSKNTVYLQMNSLRAEDTATYY CAVLQTTEQKIFEDYINYWGQGTQVTVSS | sanid3-24 |
| 100 | EVQLQASGGGFVQPGGSLRLSCAASGRADSWQDMGWFRQAPGKEREF VSAISQRAQHWTYYADSVKGRFTISRDNSKNTVYLQMNSLRAEDTATYY CARLPAFSGNARSPYDNYWGQGTQVTVSS | sanid3-25 |

*Fig. 6*

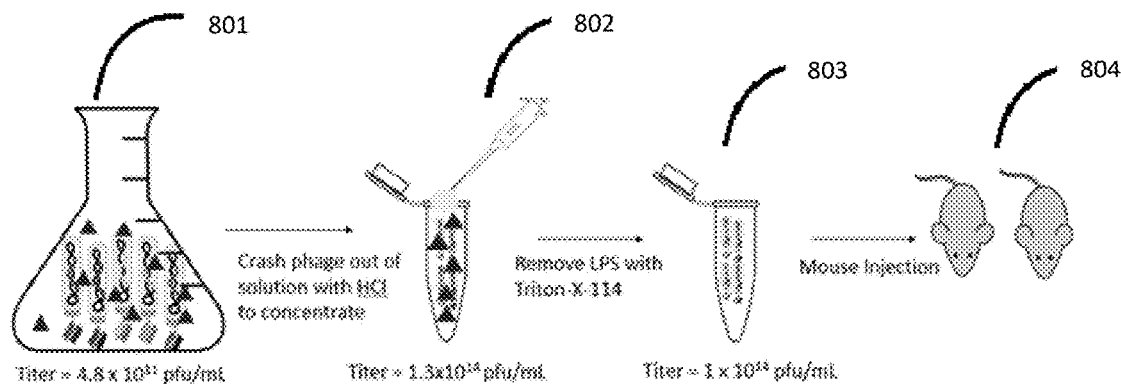
Fig. 8
| Phage Purification Pipeline | |
|---|---|
| Treatment | M13 Phage Titer (pfu/mL) |
| Stock from Antibody Design Lab | $2.6 \times 10^{12}$ |
| Liquid Culture Stock | $4.8 \times 10^{11}$ |
| Isoelectric Precipitation | $1.3 \times 10^{14}$ |
| Endotoxin removed phage prep | $1 \times 10^{14}$ |
Fig. 9
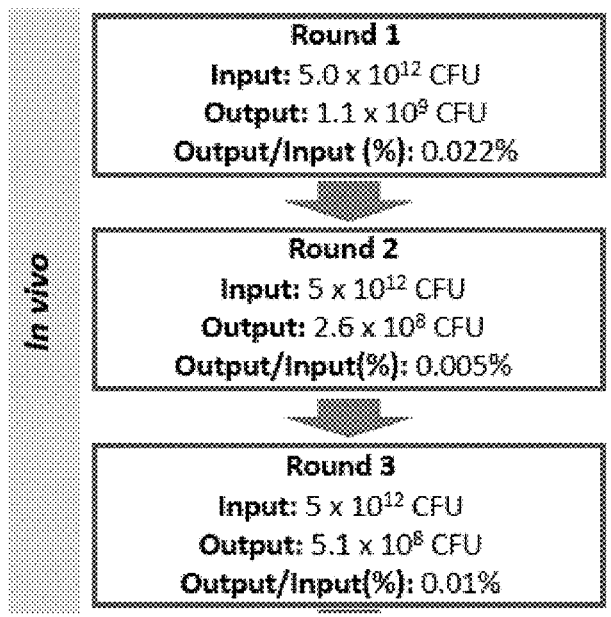
Fig. 10

| SEQ ID NO: | Enrichment Factor | |
|---|---|---|
| | R2 | R3 |
| 76 | 0.8 | 172.7 |
| 77 | 12.5 | 113.4 |
| 78 | 26.2 | 110.8 |
| 79 | 1.4 | 97.9 |
| 80 | 1.3 | 93.6 |
| 81 | 13.0 | 92.4 |
| 82 | 4.8 | 86.0 |
| 83 | 9.3 | 84.7 |
| 84 | 3.9 | 82.0 |
| 85 | 26.6 | 80.5 |
| 86 | 1.4 | 79.8 |
| 87 | 3.8 | 75.6 |
| 88 | 5.2 | 72.3 |
| 89 | 4.4 | 71.0 |
| 90 | 13.6 | 66.7 |
| 91 | 6.7 | 65.1 |
| 92 | 8.1 | 63.4 |
| 93 | 3.4 | 63.2 |
| 94 | 1.9 | 60.9 |
| 95 | 4.6 | 59.7 |
| 96 | 3.0 | 54.4 |
| 97 | 2.4 | 51.9 |
| 98 | 2.4 | 50.6 |
| 99 | 15.9 | 49.0 |
| 100 | 70.9 | 46.6 |

*FIG. 11*

| SEQ ID NOs | |
|---|---|
| | FR1 |
| 405 | EVQLQASGGGFVQPGGSLRLSCAASG |
| | FR2 |
| 406 | MGWFRQAPGKEREFVSAIS |
| | FR3 |
| 407 | YADSVKGRFTISRDNSKNTVYLQMNSLRAEDTATYYCA |
| | FR4 |
| 408 | YWGQGTQVTVSS |

*Fig. 16*

EVQLQASGGGFVQPGGSLRLSCAASG-CDR1-MGWFRQAPGKEREFVSAIS-CDR2-
YADSVKGRFTISRDNSKNTVYLQMNSLRAEDTATYYCA-CDR3-YWGQGTQVTVSS     (SEQ ID NO:183)

EVQLQASGGGFVQPGGSLRLSCAASG-CDR1-MGWFRQAPGKEREFVSAIS-CDR2-
YADSVKGRFTISRDNSKNTVYLQMNSLRAEDTATYYCA-CDR3-YWGQGTQVTVSS     (SEQ ID NO:184)

EVQLQASGGGFVQAGGSLRLSCAASG-CDR1-MGWFRQAPGKEREFVAAIS-CDR2-
YYADSVKGRFTISRDNAKNTVYLQMNSLKPEDTATYYCA-CDR3-YWGQGTQVTVSS    (SEQ ID NO:185)

EVQLQASGGGFVQAGGSLRLSCAASG-CDR1-MGWFRQAPGKEREFVAAIS-CDR2-
YYADSVKGRFTISRDNAKNTVYLQMNSLKPEDTATYYCA-CDR3-YWGQGTQVTVSS    (SEQ ID NO:186)

| | |
|---|---|
| EVQLQASGGGFVQAGGSLRLSCAASG | (SEQ ID NO:190) |
| EVQLQASGGGFVQPGGSLRLSCAASG | (SEQ ID NO:191) |
| QVQLVESGGGSVQAGGSLRLSCTASGGSEY | (SEQ ID NO:192) |
| QVQLVESGGGSVQAGGSLRLSCTASG | (SEQ ID NO:193) |
| QVQLVESGGGSVQAGGSLRLSCTASGFSRE | (SEQ ID NO:194) |
| QVQLQESGPSLVRPSQTLSLTCTISGFSRE | (SEQ ID NO:195) |
| QVQLQESGPSLVRPSQTLSLTCTISG | (SEQ ID NO:196) |
| QVQLVESGGNLVQPGGSLRLSCAASGFTFG | (SEQ ID NO:197) |
| QVQLVESGGNLVQPGGSLRLSCAASG | (SEQ ID NO:198) |
| QVQLVESGGALVQPGGSLRLSCAASGFPVN | (SEQ ID NO:199) |
| QVQLVESGGALVQPGGSLRLSCAASGFTFG | (SEQ ID NO:200) |
| QVQLVESGGGLVQPGGSLRLSCAASGFTFG | (SEQ ID NO:201) |
| QVQLVESGGALVQPGGSLRLSCAASG | (SEQ ID NO:202) |
| QVQLVESGGGLVQAGGSLRLSCAASG | (SEQ ID NO:203) |
| QVQLVESGGGLMQAGGSLRLSCAVSG | (SEQ ID NO:204) |
| QVQLQESGGGLVQAGGSLRLSCAASG | (SEQ ID NO:205) |
| HVQLVESGGGLVQAGGSLRLSCAASG | (SEQ ID NO:206) |
| DVQLVESGGGLVQAGGSLRLSCAASG | (SEQ ID NO:207) |
| EVQLVESGGGLVQAGGSLRLSCAASG | (SEQ ID NO:208) |
| EVQLVESGGGVVQPGRSLRLSCAASGFTFD | (SEQ ID NO:209) |
| EVQLVESGGGVVQPGRSLRLSCAASG | (SEQ ID NO:210) |
| DVQLQASGGGLVQAGGSLRLSCAASGFKIT | (SEQ ID NO:211) |
| DVQLQASGGGLVQAGGSLRLSCAASG | (SEQ ID NO:212) |

*Fig. 18A*

```
FR2
MGWFRQAPGKEREFVAAIS       (SEQ ID NO:220)
MGWFRQAPGKEREFVSAIS       (SEQ ID NO:221)
--WFRQAPGQEREAVA          (SEQ ID NO:222)
--WFRQAPGQEREAVAAIA       (SEQ ID NO:223)
--WVRQAPGKALEWLG          (SEQ ID NO:224)
--WVRQAPGKALEWLGRI        (SEQ ID NO:225)
--WFRQAPGQEREWLG          (SEQ ID NO:226)
--WFRQAPGQEREWLGRI        (SEQ ID NO:227)
--WVRQAPGGGLEWVA          (SEQ ID NO:228)
--WYRQATGKEREWVA          (SEQ ID NO:229)
MSWYRQATGKEREWVA          (SEQ ID NO:230)
MGWFRQAPGKEREFVAAIR       (SEQ ID NO:231)
MGWFRQAPGKEREFVAAI        (SEQ ID NO:232)
MGWFRQAPGKEREFVA          (SEQ ID NO:233)
MGWYRQAPGKERELVA          (SEQ ID NO:234)
MGWYRQAPGKERELVAA         (SEQ ID NO:235)
MGWYRQAPGKERELVAAID       (SEQ ID NO:236)
MGWYRQAPGKERELVAVIS       (SEQ ID NO:237)
MGWFRQAPGKEREGVA          (SEQ ID NO:238)
--WFRQAPGKEREGVA          (SEQ ID NO:239)
MGWFRQAPGKEREFVA          (SEQ ID NO:240)
--WFRQAPGKEREFVA          (SEQ ID NO:241)
--WVRQAPGKGPEWVA          (SEQ ID NO:242)
--WFRQAPGKEREFVS          (SEQ ID NO:243)
```

*Fig. 18B*

```
FR3
-YADSVKGRFTISRDNAKNTVYLQMNSLKPEDTATYYCA-          (SEQ ID NO:250)
YYADSVKGRFTISRDNAKNTVYLQMNSLKPEDTATYYCA-          (SEQ ID NO:251)
-YADSVKGRFTISRDNSKNTVYLQMNSLRAEDTATYYCA-          (SEQ ID NO:252)
YYADSVKGRFTISRDNSKNTVYLQMNSLRAEDTATYYCA-          (SEQ ID NO:253)
--------RFTISRDNAKNTVTLQMNNLKPEDTAIYYCA-          (SEQ ID NO:254)
--------RFTISRDNAKNTVTLQMNNLKPEDTAIYYCAA          (SEQ ID NO:255)
--------RLTITRDISKSQVSLSLSSVTLEDTAEYYCV-          (SEQ ID NO:256)
--------RLTITRDISKSQVSLSLSSVTLEDTAEYYCVY          (SEQ ID NO:257)
--------RFTISRDIAKNTVTLQMNNLKPEDTAIYYVY-          (SEQ ID NO:258)
--------RFTISRDIAKNTVTLQMNNLKPEDTAIYYVYA          (SEQ ID NO:259)
YYADSVKGRFTISRDNAKNTVTLQMNNLKPEDTAIYYCA-          (SEQ ID NO:260)
YYADSVKGRFTISRDNAKNTVTLQMNNLKPEDTAIYYCAA          (SEQ ID NO:261)
-YEDSVKGRFCISRDDARNTVYLQMNSLKPEDTAVYYCNV          (SEQ ID NO:262)
-YEDSVKGRFCISRDDARNTVYLQMNSLKPEDTAVYYCN-          (SEQ ID NO:263)
-YADSVKGRFTISRDNAKNSVYLQMNSLRVEDTAVYYCAR          (SEQ ID NO:264)
-YADSVKGRFTISRDNAKNSVYLQMNSLRVEDTAVYYCA-          (SEQ ID NO:265)
-YADSVKGRFTISRDNARNTVYLQMNSLKPEDTAVYYCAR          (SEQ ID NO:266)
-YADSVKGRFTISRDNARNTVYLQMNSLKPEDTAVYYCA-          (SEQ ID NO:267)
-YADSVKGRFTISRDNARNTVYLQMNSLKPEDTAVYYCAR          (SEQ ID NO:268)
--------RFTISRDNARNTVYLQMNSLKPEDTAVYYCAR          (SEQ ID NO:269)
-YADSVKGRFTISRDKGKNTVYLQMDSLKPEDTATYYCAA          (SEQ ID NO:270)
--------RFTISRDKGKNTVYLQMDSLKPEDTATYYCAA          (SEQ ID NO:271)
-YADSVKGRFTISRDKGKNTVYLQMDSLKPEDTATYYCA-          (SEQ ID NO:272)
--------RFTISRDKGKNTVYLQMDSLKPEDTATYYCA-          (SEQ ID NO:273)
YYADSVKGRFTISRDKAKNTVYLQMNSLKYEDTAVYYCA-          (SEQ ID NO:274)
-YADSVKGRFTISRDKAKNTVYLQMNSLKYEDTAVYYCA-          (SEQ ID NO:275)
YYADSVKGRFTISRDNAKNTVYLQMNSLKPEDTAVYYCA-          (SEQ ID NO:276)
LHNPALKSRLTITRDISKSQVSLSLSSVTLEDTAEYYCV-          (SEQ ID NO:277)
LHNPALKSRLTITRDISKSQVSLSLSSVTLEDTAEYYCVY          (SEQ ID NO:278)
LHNPALKSRFTISRDIAKNTVTLQMNNLKPEDTAIYYVYA          (SEQ ID NO:279)
-YADSVKGRFTISRDNAKNTVYLQMNSLKPEDTAVYYCAA          (SEQ ID NO:280)
-YADSVKGRFTISRDNAKNTVYLQMNSLKPEDTAVYYCA-          (SEQ ID NO:281)
YYADSVKGRFTISRDNAKNTVYLQMNSLKPEDTAVYYCAA          (SEQ ID NO:282)
--------RFTISRDNSKNTLYLQMNSLRAEDTAVYYCAK          (SEQ ID NO:283)
--------RFTISRDNAKNTVYLQMNSLKPEDTADYYCAA          (SEQ ID NO:284)
```

| | |
|---|---|
| YWGQGTQVTVSS | (SEQ ID NO:290) |
| -WGQGTQVTVSS | (SEQ ID NO:291) |
| VWGPGLLLTVSS | (SEQ ID NO:292) |
| -WGPGLLLTVSS | (SEQ ID NO:293) |
| -WGQGTLVTVS- | (SEQ ID NO:294) |
| -WGQGTLVTVSS | (SEQ ID NO:295) |
| -WGQGTQVTVS- | (SEQ ID NO:296) |
| -WGQGTQVTVSS | (SEQ ID NO:297) |
| QWGQGTQVTVSS | (SEQ ID NO:298) |
| YWGQGTQVTVS- | (SEQ ID NO:299) |
| -WGQGTTVVVSS | (SEQ ID NO:300) |
| -WGKGTQVTVSS | (SEQ ID NO:301) |

*Fig. 18D*

LUNG-TARGETING SINGLE-DOMAIN ANTIBODIES AND PURIFICATION METHODS

STATEMENT OF GOVERNMENT INTEREST

This invention was made with Government support under Contract No. DE-NA0003525 awarded by the United States Department of Energy/National Nuclear Security Administration. The U.S. Government has certain rights in the invention

REFERENCE TO A SEQUENCE LISTING APPENDIX

The application contains a Sequence Listing which has been submitted electronically in .XML format and is hereby incorporated by reference in its entirety. Said .XML copy, created on Jan. 10, 2025, is named "SD-15930.xml" and is 316,827 bytes in size. The sequence listing contained in this .XML file is part of the specification and is hereby incorporated by reference herein in its entirety.

FIELD

The present disclosure relates to single-domain antibodies (sdABs), the variable target binding domain of a heavy chain only antibody. In particular, the sdABs disclosed herein are configured to target moieties enriched or specific to cells in human or mammalian lung tissue.

BACKGROUND

Therapeutic agents for various internal diseases are conventionally applied to the body systemically, either through oral consumption, inhalation, intravenous/intraperitoneal injection, mucosal absorption, or radiation therapy. These therapies are applied to the whole body or a broad area, and thus, pose risks to the whole body or broad area, or at a minimum are significantly diluted as they proceed throughout the bloodstream or into off-target tissues of a patient. For example, anti-cancer chemotherapy provides a cancer killing agent that attacks harmful cancer cells, but is also harmful to other 'normal' rapidly dividing cells in the body, inappropriately affecting the gut, for instance. Similarly, radiation is harmful to the body as a whole, even though targeted radiation therapy more specifically affects the anatomical location where the cancer resides, thereby reducing off-target side effects of whole-body irradiation. Targeted therapeutics, i.e., agents that are delivered specifically to a particular tissue or organ system, are advantageous in eliminating or decreasing unwanted side-effects in the rest of the body, because a more concentrated dosage can be delivered directly to the area of infection or concern. Also, with targeted therapeutics, barriers obstructing therapeutic efficacy are bypassed, such as poor gastrointestinal absorption and first-pass metabolism of pharmaceuticals or other therapeutic agents, which occurs in the liver. In such therapeutic systems lower overall dosage amounts can be used since they are more efficiently delivered to the problem area, and are not subject to the same rate of systemic dilution, rapid metabolism or excretion as non-targeted therapies.

Infections or other problems originating in the pulmonary system may be targeted efficiently by aerosol inhalation, or by peripheral injection (IP/IV) of a lung-targeting moiety that will be conducted via circulation and accumulate in lung tissue. The lungs have a very large absorptive surface area ($\sim$100 m$^2$) that is highly vascularized and has a highly permeable membrane ($\sim$0.2-0.7 μm thickness) in the alveolar sacs to facilitate gas exchange but also can be exploited for efficient drug delivery. Challenges remain with delivery of effective treatment agents to the lungs.

SUMMARY

Disclosed herein are sdABs configured for binding to cells in the human or mammalian pulmonary system. Methods of using such sdABs are also described herein, such as methods of binding to lung cells, binding with and transporting other sdABs with beneficial functionalities, binding to and transporting biochemical or pharmaceutical species with beneficial functionalities, including diagnosing, prophylactically treating, or treating a disease, malignancy or condition.

SdABs, as disclosed herein, are the antigen binding region of heavy chain only antibodies first identified in camels. These sdABs described here are synthetic humanized sdABs developed based on a library as described below. SdABs can also be produced as heavy chain only antibodies which are smaller and more modular than conventional antibodies with the ability to engage the immune response. SdABs disclosed herein may be formulated to include the Fc region to generate heavy chain only antibodies (HC Abs).

These shuttle sdABs can be coupled to therapeutic sdABs, antibodies, delivery vehicles, therapeutics, and/or heavy chain only antibodies in a modular manner. These therapeutic sdABs can be produced as heavy chain only antibodies for specific respiratory viruses, such as SARS-CoV-2, or other viral infections. It has been demonstrated that once the protein sequence, or genetic coding, of a virus has been identified, a sdABsdAB-based countermeasure can be developed within 120 days. Speeding up the discovery of neutralizing antibodies could reduce the impact and spread of future viral outbreaks. Neutralizing heavy chain only antibodies and sdABs represent an attractive strategy due to their modular nature, capability to be deployed in multivalent sdAB combinations, and their corresponding ability to work effectively against families of viruses and emerging variants. Importantly, utilizing heavy chain only antibodies further allows exploitation of distinct immune pathways specifically linked to a given virus or family of viruses. Thus, sdAB treatments can be selected to therapeutically target commonalities between viral family members and their variants, but also can be rapidly adapted to additional disparate variants as they emerge.

Modular sdABs can be combined with other sdABs to provide specificity to a target tissue as well as neutralizing activity against a given virus. The bispecific nature of combining sdABs can increase therapeutic efficacy by clearing the infection locally, and reducing the likelihood of systemic complications.

Additionally, due to the small size of the sdABs, they can be released into the blood and penetrate tissues more thoroughly than conventional antibodies. SdAB therapies can also target an infection site directly, decreasing the dose needed and increasing efficacy. SdABs can also be administered via aerosol, so they can be given to a patient by inhalation. Conventional antibody treatments are less versatile.

These qualities and features of sdABs make tissue-targeted sdAB therapies potentially much more effective than current solutions. These treatments are also easier and cheaper to manufacture.

In particular, provided herein are lung-tissue targeting sdAB-based constructs comprising a shuttle sdAB and a biochemical, diagnostic, or pharmaceutical cargo. In an embodiment, a lung-tissue targeting shuttle sdAB construct comprises: a sdAB and an Fc domain with hinge region of human IgG1 protein. The sdAB is coupled to the hinge region of the Fc domain. The sdAB construct is configured to target lung tissue as indicated by experiments showing specific enrichment of the sdABs in the lung tissue. While it was not conclusively, experimentally determined that "binding" under some definitions of that term technically took place between the sdAB and an epitope on the lung tissue, it was indicated that specific enrichment of the sdABs was found in the lung tissue and that was not found at all or to the same extent in other tissues (e.g., 10% or greater accumulation in the lungs than, for example, the liver). The term "targeting" contemplates an affinity for binding to or some other mechanism of coupling to the tissue.

In some aspects, the techniques described herein relate to a sdAB construct, including a first sdAB with a binding domain, wherein the binding domain includes: a first complementarity determining region including a polypeptide sequence having at least 80% sequence identity to any one of SEQ ID NOs: 1-25; a second complementarity determining region including a polypeptide sequence having at least 80% sequence identity to any one of SEQ ID NOs: 26-50; and a third complementarity determining region including a polypeptide sequence having at least 80% sequence identity to any one of SEQ ID NOs: 51-75.

In some aspects, the techniques described herein relate to a sdAB construct, wherein the binding domain includes: a first complementarity determining region including a polypeptide sequence having at least 90% sequence identity to any one of SEQ ID NOs: 1-25; a second complementarity determining region including a polypeptide sequence having at least 90% sequence identity to any one of SEQ ID NOs: 26-50; and a third complementarity determining region including a polypeptide sequence having at least 90% sequence identity to any one of SEQ ID NOs: 51-75.

In some aspects, the techniques described herein relate to a method for purifying and concentrating a solution including a lysate of a phagemid, including the steps of: causing isoelectric precipitation in the solution by adding a sufficient amount of acid to a solution including a lysate of a phagemid, the phagemid including DNA inserts of a sequence configured to allow for expression of a sdAB; separating the precipitate of the isoelectric precipitation from a supernatant; dissolving the precipitate in a polar liquid to form a purification solution; adding a sufficient amount of an endotoxin removal agent to neutralize endotoxins in the purification solution; separating a purified and concentrated phage lysate from the purification solution.

In embodiments of the binding domain, the first framework region includes a polypeptide sequence having at least 90% sequence identity to any one of SEQ ID NOs: 190-212 or 405. In embodiments, the second framework region includes a polypeptide sequence having at least 90% sequence identity to any one of SEQ ID NOs: 220-243 or 406. In embodiments, the third framework region includes a polypeptide sequence having at least 90% sequence identity to any one of SEQ ID NOs: 250-284 or 407. In embodiments, the fourth framework region includes a polypeptide sequence having at least 90% sequence identity to any one of SEQ ID NOs: 290-301 or 408.

In an embodiment, the antibody or fragment thereof further includes a linker disposed between the first and second binding domains. Non-limiting linkers include any described herein, such as, GGG, SEQ ID NOs: 311-319 and/or A.

In another aspect, the present disclosure features methods of prophylactically treating, diagnosing or treating a disease, malignancy, or condition. In some embodiments, the method includes: administering an isolated or purified antibody or fragment thereof (e.g., any described herein) to a subject in need thereof. In other embodiments, the isolated or purified antibody or fragment thereof is provided as a pharmaceutical composition comprising a shuttle sdAB for a biochemical or pharmaceutically active agent.

In some embodiments, the viral infection includes an infection from a coronavirus. In other embodiments, the coronavirus is SARS-CoV-2 or a variant thereof. A variant as used herein includes mutated versions.

The terms "polynucleotide" and "nucleic acid," used interchangeably herein, refer to a polymeric form of nucleotides of any length, either ribonucleotides or deoxyribonucleotides. Thus, this term includes, but is not limited to, single-stranded (e.g., sense or antisense), double-stranded, or multi-stranded ribonucleic acids (RNAs), deoxyribonucleic acids (DNAs), threose nucleic acids (TNAs), glycol nucleic acids (GNAs), peptide nucleic acids (PNAs), locked nucleic acids (LNAs), or hybrids thereof, genomic DNA, cDNA, DNA-RNA hybrids, or a polymer comprising purine and pyrimidine bases or other natural, chemically or biochemically modified, non-natural, or derivatized nucleotide bases. Polynucleotides can have any useful two-dimensional or three-dimensional structure or motif, such as regions including one or more duplex, triplex, quadruplex, hairpin, and/or pseudoknot structures or motifs.

The term "modified," as used in reference to nucleic acids, means a nucleic acid sequence including one or more modifications to the nucleobase, nucleoside, nucleotide, phosphate group, sugar group, and/or internucleoside linkage (e.g., phosphodiester backbone, linking phosphate, or a phosphodiester linkage).

The term "modified," as used in reference to amino acids, means an amino acid including one or more modifications, such as a post-translation modification (e.g., acetylation, methylation, phosphorylation, ubiquitination, sumoylation, ribosylation, glycosylation, acylation, or isomerization), or including a non-natural amino acid.

The term "modified," as used in reference to a protein, means a polypeptide sequence including one or more amino acid substitution, as compared to the reference sequence for the protein.

"Complementarity" or "complementary" or "complement" refers to the ability of a nucleic acid to form hydrogen bond(s) with another nucleic acid sequence by either traditional Watson-Crick or other non-traditional types, e.g., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. As is known in the art, standard Watson-Crick base-pairing includes: adenine (A) pairing with thymidine (T), adenine (A) pairing with uracil (U), and guanine (G) pairing with cytosine (C). In addition, it is also known in the art that for hybridization between two RNA molecules (e.g., dsRNA), guanine (G) base pairs with uracil (U). A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" or "sufficient complementarity" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Examples of stringent conditions are described in detail in Tijssen (1993), Laboratory Techniques In Biochemistry And Molecular Biology-Hybridization With Nucleic Acid Probes Part 1, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. Hybridization and washing conditions are well known and exemplified in Sambrook J, Fritsch E F, and Maniatis T, "Molecular Cloning: A Laboratory Manual," Second Edition, Cold Spring Harbor Laboratory Press, Cold Spring Harbor (1989), particularly Chapter 11 and Table 11.1 therein; and Sambrook J and Russell W, "Molecular Cloning: A Laboratory Manual," Third Edition, Cold Spring Harbor Laboratory Press, Cold Spring Harbor (2001). The conditions of temperature and ionic strength determine the "stringency" of the hybridization.

Hybridization requires that the two nucleic acids contain complementary sequences, although mismatches between bases are possible. The conditions appropriate for hybridization between two nucleic acids depend on the length of the nucleic acids and the degree of complementation, variables well known in the art. The greater the degree of complementation between two nucleotide sequences, the greater the value of the melting temperature (Tm) for hybrids of nucleic acids having those sequences. For hybridizations between nucleic acids with short stretches of complementarity (e.g., complementarity over 35 or less, 30 or less, 25 or less, 22 or less, 20 or less, or 18 or less nucleotides) the position of mismatches becomes important (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; at least about 22 nucleotides; at least about 25 nucleotides; and at least about 30 nucleotides. Furthermore, the skilled artisan will recognize that the temperature and wash solution salt concentration may be adjusted as necessary according to factors such as length of the region of complementation and the degree of complementation.

It is understood in the art that the sequence of polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. Percent complementarity between particular stretches of nucleic acid sequences within nucleic acids can be determined routinely using BLAST programs (basic local alignment search tools) and PowerBLAST programs known in the art (Altschul S F et al., J. Mol. Biol. 1990; 215:403-10; Zhang J et al., Genome Res. 1997; 7:649-56) or by using the Gap program (Wisconsin Sequence Analysis Package, Version 8 for Unix, Genetics Computer Group, University Research Park, Madison Wis.), using default settings, which uses the algorithm of Smith T F et al., Adv. Appl. Math. 1981; 2(4):482-9.

By "protein," "peptide," or "polypeptide," as used interchangeably, is meant any chain of more than two amino acids, regardless of post-translational modification (e.g., glycosylation or phosphorylation), constituting all or part of a naturally occurring polypeptide or peptide, or constituting a non-naturally occurring polypeptide or peptide, which can include coded amino acids, non-coded amino acids, modified amino acids (e.g., chemically and/or biologically modified amino acids), and/or modified backbones. Non-limiting amino acids include glycine (Gly, G), alanine (Ala, A), valine (Val, V), isoleucine (Ile, I), leucine (Leu, L), cysteine (Cys, C), methionine (Met, M), aspartic acid (Asp, D), glutamic acid (Glu, E), arginine (Arg, R), histidine (His, H), lysine (Lys, K), asparagine (Asn, N), glutamine (Gln, Q), serine (Ser, S), threonine (Thr, T), proline (Pro, P), phenylalanine (Phe, F), tyrosine (Tyr, Y), tryptophan (Trp, W), selenocysteine (Sec, U), and pyrrolysine (Pyl, O).

The term "fragment" means a portion of a nucleic acid or a polypeptide that is at least one nucleotide or one amino acid shorter than the reference sequence. This portion contains, preferably, at least about 85%, 95%, or 99% of the entire length of the reference nucleic acid molecule or polypeptide. A fragment may contain 10, 20, 30, 40, 50, 60, 70, 80, 90, or 100, 200, 300, 400, 500, 600, 700, 800, 900, 1000, 1250, 1500, 1750, 1800 or more nucleotides; or 10, 20, 30, 40, 50, 60, 70, 80, 90, 100, 150, 200, 250, 300, 350, 400, 450, 500, 550, 600, 640 amino acids or more. In another example, any polypeptide fragment can include a stretch of at least about 5 (e.g., about 10, about 20, about 30, about 40, about 50, or about 100) amino acids that are at least about 80%, about 90%, about 95%, about 97%, about 98%, about 99%, or about 100%) identical to any of the sequences described herein. In certain embodiments, a polypeptide disclosed herein includes 2, 3, 4, 5, 6, 7, 8, 9, 10, or more mutations (e.g., one or more conservative amino acid substitutions, as described herein). In yet another example, any nucleic acid fragment can include a stretch of at least about 5 about 10, about 28, about 30, or more nucleotides that are at least about 80%, about 90%, about 95%, about 87%, about 98%, about 99%, or about 100% identical to any of the sequences described herein.

The term "conservative amino acid substitution" refers to the interchangeability in proteins of amino acid residues having similar side chains (e.g., of similar size, charge, and/or polarity). For example, a group of amino acids having aliphatic side chains consists of glycine (Gly, G), alanine (Ala, A), valine (Val, V), leucine (Leu, L), and isoleucine (Ile, I); a group of amino acids having aliphatic-hydroxyl side chains consists of serine (Ser, S) and threonine (Thr, T); a group of amino acids having amide containing side chains consisting of asparagine (Asn, N) and glutamine (Gln, Q); a group of amino acids having aromatic side chains consists of phenylalanine (Phe, F), tyrosine (Tyr, Y), and tryptophan (Trp, W); a group of amino acids having basic side chains consists of lysine (Lys, K), arginine (Arg, R), and histidine (His, H); a group of amino acids having acidic side chains consists of glutamic acid (Glu, E) and aspartic acid (Asp, D); and a group of amino acids having sulfur containing side chains consists of cysteine (Cys, C) and methionine (Met, M).

As used herein, when a polypeptide or nucleic acid sequence is referred to as having "at least X % sequence identity" to a reference sequence, it is meant that at least X percent of the amino acids or nucleotides in the polypeptide or nucleic acid are identical to those of the reference sequence when the sequences are optimally aligned. An optimal alignment of sequences can be determined within the skill in the art, for instance, by the BLAST (Basic Local Alignment Search Tool; Altschul S F et al., J. Mol. Biol. 1990; 215:403-10). This algorithm is accessible using publicly available computer software such as "Best Fit" (Smith T F et al., Adv. Appl. Math. 1981; 2(4):482-9) as incorporated into GeneMatcher Plus™. In addition, those skilled in the art can determine appropriate parameters for measuring alignment, including any algorithms needed to achieve optimal alignment over the length of the sequences being compared. It is understood that for the purposes of determining sequence identity when comparing a DNA sequence to an RNA sequence, a thymine nucleotide is equivalent to an uracil nucleotide.

By "substantial identity" or "substantially identical" is meant a polypeptide or nucleic acid sequence that has the same polypeptide or nucleic acid sequence, respectively, as a reference sequence, or has a specified percentage of amino acid residues or nucleotides, respectively, that are the same at the corresponding location within a reference sequence when the two sequences are optimally aligned. For example, an amino acid sequence that is "substantially identical" to a reference sequence has at least about 90%, 95%, 96%, 97%, 98%, 99%, or 100% sequence identity to the reference amino acid sequence. For polypeptides, the length of comparison sequences will generally be at least 5, 6, 7, 8, 9, 10, 11, 12, 13, 14, 15, 16, 17, 18, 19, 20, 25, 50, 75, 90, 100, 150, 200, 250, 300, or 350 contiguous amino acids (e.g., a full-length sequence). For nucleic acids, the length of comparison sequences will generally be at least 5, 10, 11, 12, 13, 14, 15, 16, 17, 18, 19, 20, 21, 22, 23, 24, or 25 contiguous nucleotides (e.g., the full-length nucleotide sequence). Sequence identity may be measured using sequence analysis software on the default setting (e.g., Sequence Analysis Software Package of the Genetics Computer Group, University of Wisconsin Biotechnology Center, 1710 University Avenue, Madison, Wis., 53705). Such software may match similar sequences by assigning degrees of homology to various substitutions, deletions, and other modifications.

A "vector" or "expression vector" is a replicon, such as plasmid, phage, virus, or cosmid, to which another nucleic acid segment, i.e., an "insert", may be attached so as to bring about the replication of the attached segment in a cell.

An "expression cassette" comprises a nucleic acid coding sequence operably linked, as defined herein, to a promoter sequence, as defined herein.

"Operably linked" or "operatively linked" or "operatively associated with," as used interchangeably, refers to a juxtaposition wherein the components so described are in a relationship permitting them to function in their intended manner. For instance, a promoter is operably linked to a coding sequence if the promoter affects its transcription or expression. A nucleic acid molecule is operatively linked or operably linked to, or operably associated with, an expression control sequence when the expression control sequence controls and regulates the transcription and translation of nucleic acid sequence. The term "operatively linked" includes having an appropriate start signal (e.g., ATG) in front of the nucleic acid sequence to be expressed and maintaining the correct reading frame to permit expression of the nucleic acid sequence under the control of the expression control sequence and production of the desired product encoded by the nucleic acid sequence. If a gene that one desires to insert into a recombinant DNA molecule does not contain an appropriate start signal, such a start signal can be inserted in front of the gene.

By an "effective amount" or a "sufficient amount" of an agent, as used herein, is that amount sufficient to effect beneficial or desired results, such as clinical results, and, as such, an "effective amount" depends upon the context in which it is being applied. For example, in the context of administering an agent that is an antiviral agent, an effective amount of an agent is, for example, an amount sufficient to achieve a reduction in viral load or a mitigation of a symptom related to a viral infection or a delay in a symptom related to a viral infection, as compared to the response obtained without administration of the agent.

By "subject" or "patient" is meant a human or non-human animal (e.g., a mammal).

By "treating" a disease, malignancy, or condition in a subject is meant reducing at least one symptom of the disease, malignancy, or condition by administrating a therapeutic agent to the subject. By "treating prophylactically" or "prophylactically treating" a disease, malignancy, or condition in a subject is meant reducing the frequency of occurrence of or reducing the severity of a disease, malignancy or condition by administering a therapeutic agent to the subject prior to the onset of disease symptoms. Beneficial or desired results can include, but are not limited to, alleviation or amelioration of one or more symptoms or conditions; diminishment of extent of disease, malignancy, or condition; stabilized (i.e., not worsening) state of disease, malignancy, or condition; preventing spread of disease, malignancy, or condition; delay or slowing the progress of the disease, malignancy, or condition; amelioration or palliation of the disease, malignancy, or condition; and/or remission (whether partial or total), whether detectable or undetectable.

By "attached," "attaching," "attachment," or related word forms is meant any covalent or non-covalent bonding interaction between two components. Non-covalent bonding interactions include, without limitation, hydrogen bonding, ionic interactions, halogen bonding, electrostatic interactions, π bond interactions, hydrophobic interactions, inclusion complexes, clathration, van der Waals interactions, and combinations thereof.

A "host cell," as used herein, denotes an in vivo or in vitro eukaryotic cell, a prokaryotic cell (e.g., bacterial or archaeal cell), or a cell from a multicellular organism (e.g., a cell line) cultured as a unicellular entity, which eukaryotic or prokaryotic cells can be, or have been, used as recipients for a nucleic acid, and include the progeny of the original cell which has been transformed by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject bacterial host cell is a genetically modified bacterial host cell by virtue of introduction into a suitable bacterial host cell of an exogenous nucleic acid (e.g., a plasmid or recombinant expression vector) and a subject eukaryotic host cell is a genetically modified eukaryotic host cell (e.g., a mammalian germ cell), by virtue of introduction into a suitable eukaryotic host cell of an exogenous nucleic acid.

By "linker" is meant any useful multivalent (e.g., bivalent) component useful for joining to different portions or segments. Exemplary linkers include a nucleic acid sequence, a chemical linker, etc. In one instance, the linker of the guiding component (e.g., linker L in the interacting portion of the guiding component) can have a length of from about 3 nucleotides to about 100 nucleotides. For example, the linker can have a length of from about 3 nucleotides (nt) to about 90 nt, from about 5 nucleotides (nt) to about 80 nt, from about 6 nucleotides (nt) to about 70 nt, from about 8 nucleotides (nt) to about 50 nt, from about 10 nucleotides (nt) to about 350 nt.

The term "sdAB construct" as used herein means one or more sdABs coupled to another structure, such as, a portion of an antibody, a modified antibody, a synthetic or natural particle, a humanized Fc, a mammalian Fc or other Fc, or another sdAB these may include or may additionally be coupled to other structures such as linkers or hinge regions.

BRIEF DESCRIPTION OF THE DRAWINGS

FIG. 3 provides example sequences for CDRs, including sequences for complementarity determining region 1 (CDR1, SEQ ID NOs:1-25), complementarity determining region 2 (CDR2, SEQ ID NOs: 26-50), and complementarity determining region 3 (CDR3, SEQ ID NOs: 51-75).

FIG. 4 is an example schematic of an antibody having framework regions (FRs) interspersed with complementarity determining regions (CDRs), in which a sdAB can include framework regions 1-4 (FR1, FR2, FR3, and FR4) with interspersed CDR1, CDR2, and CDR3.

FIG. 5 provides example sdAB sequences corresponding to SEQ ID NOs: 76-90.

FIG. 6 provides example sdAB sequences corresponding to SEQ ID NOs: 91-100.

FIG. 8 is a schematic showing an example of the isoelectric precipitation and endotoxin purification steps.

FIG. 9 is a table showing phage titers at certain steps in the example methods disclosed herein.

FIG. 10 is a schematic showing the cfu counts at different rounds of the biopanning disclosed in the Examples.

FIG. 11 is a table showing enrichment factors for various sequences in the second and third rounds of biopanning disclosed in the Examples.

FIG. 16 lists sequences for framework regions FR1, FR2, FR3, and FR4 (SEQ ID NOs. 405-408, respectively).

FIG. 17 provides additional example sequences for framework regions FR1, FR2, FR3, and FR4.

FIGS. 18A-18D provide (A) a sequence alignment of example FR1 sequences (SEQ ID NOs:190-212); (B) a sequence alignment of example FR2 sequences (SEQ ID NOs:220-243); (C) a sequence alignment of example FR3 sequences (SEQ ID NOs:250-284); and (D) a sequence alignment of example FR4 sequences (SEQ ID NOs:290-301).

DETAILED DESCRIPTION

Figure 1:
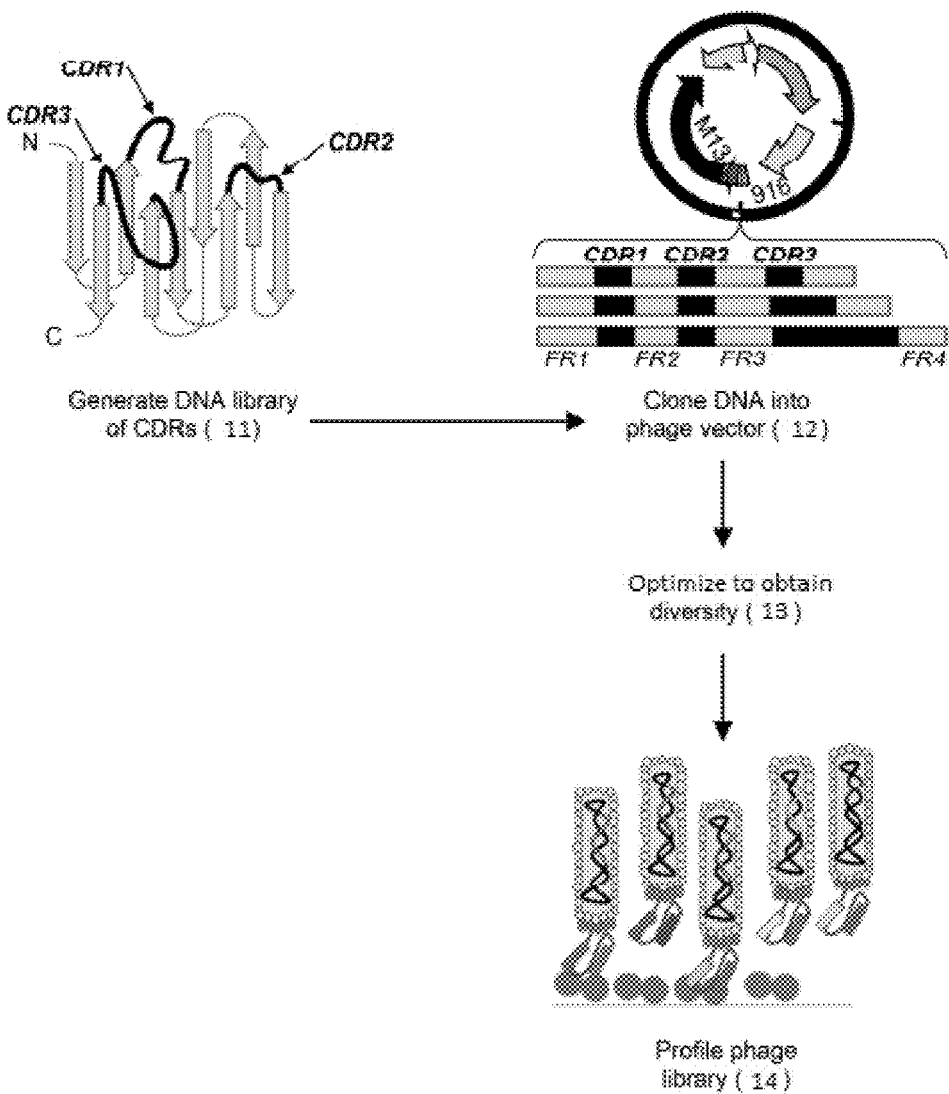
FIG. 1 shows a schematic of an example method for synthesizing a library of sdABs.
Figure 2:
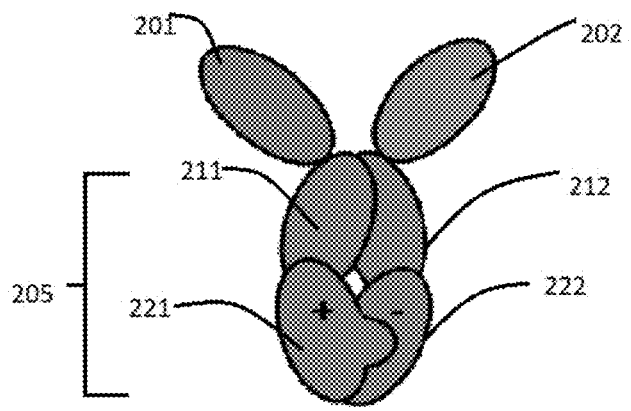
FIG. 2 is a schematic of an example sdAB construct.

This disclosure relates to an isolated or purified sdAB construct comprising a sdAB with a binding region that targets human or mammalian lung tissue (including Alveolar Epithelial Cells, AEC Type I and II, airway epithelial cells, and submucosa). In an embodiment, the lung-targeting sdABs are bound to a humanized Fc and/or the sdAB construct includes a biochemical or pharmaceutical active agent.

From a novel synthetic library that was designed to find highly potent sdABs that are both easier to manufacture and more accessible to certain proteins and smaller tissues than conventional antibodies, the sdABs disclosed herein were identified and tested. Certain sdABs were paired together on a humanized Fc and tested and found to be present in sufficient quantities to indicate effective targeting of and delivery to lung tissue.

As disclosed herein, complementarity determining regions (CDRs) were identified that provide enhanced efficacy in targeting lung tissue, as determined by in vivo testing. Such CDRs can be provided in an antibody having a useful format, such as a sdAB, either separate or joined to a human Fc and/or joined to a useful cargo or other forms described herein.

CDRs for the sdAB were identified starting with using a phage library (FIG. 1). FIG. 1 shows a description of how the library was constructed. The library incorporated both the diversity and prevalence of amino acids at key positions in each of the CDR1 and CDR2 derived from a single domain antibody (sdAb) database. This database contained sequences of validated sdAbs or sdABs from both synthetic and natural sources from both naive and immune repertoires. Components of the database were curated using sequences derived from existing databases (Protein Data Bank and NCBI) and publications.

Such a library can be constructed by generating 11 a DNA library of CDRs with high diversity, cloning 12 the DNA into a phage vector to express sdABs as fusion proteins with the phage coat protein, optimizing 13 the transformation to obtain phages having sufficient diversity, and profiling 14 the phage library by sequencing. Diversity can include distribution in both the amino acid content and the length of the CDRs.

The library used herein was designed to have 3 different CDR3 lengths and incorporated the natural prevalence of amino acid at specific CDR positions for CDR1 and CDR2 derived from 655 effective sdABs selected with information provided in Emily E. Wilton, et al., "sdAb-DB: The Single Domain Antibody Database," *ACS Synthetic Biology* 2018 7 (11), 2480-2484, DOI: 10.1021/acssynbio.8b00407, incorporated herein by reference.

For CDR3 all amino acids were used with the exception of cysteine and methionine. The library was constructed using novel DNA synthesis technology ensuring high quality and full length sdABs with low incidence of stop codons. These attributes allow for the identification of highly potent binders to desired targets with femtomolar to nanomolar dissociation constants. The library was cloned into the pADL20c M13 phagemid vector, which allowed expression of sdABs as a fusion protein to coat protein gIIIp of M13 phage. Purification and concentration steps were also taken to improve the library sample for in vivo testing.

The purified and concentrated library was then screened by intravenous injection into several mice. The mice lungs were harvested one-hour later. The lungs were dissociated, phage extracted, grown up, re-purified, and lung-phages were re-injected into several mice two additional times (as described herein) to ensure lung-targeting sdAB enrichment in the lung above other tissues.

Phage populations at each round were sequenced to gauge enrichment and selection over time. From this in vivo biopanning campaign 25 top candidate sdABs for minimally-invasive lung-targeting were identified.

Further confirmation screening using sdAB-human Fc fusion protein versions of these 25 candidates was also performed by injection into mice, perfusion, and harvest of lungs, and validation by immunohistochemistry staining to show spatial and temporal lung-targeting efficacy of several of the candidates.

Further information on the library is disclosed in the Examples section and in the publication Stefan M A, Light Y K, Schwedler J L, McIlroy P R, Courtney C M, Saada E A, Thatcher C E, Phillips A M, Bourguet F A, Mageeney C M, McCloy S A, Collette N M, Negrete O A, Schoeniger J S, Weilhammer D R, Harmon B. Development of potent and effective synthetic SARS-CoV-2 neutralizing nanobodies. MAbs. 2021 January-December; 13(1):1958663 (published online Aug. 4, 2021) incorporated herein by reference. In particular, plasmids for expression of the sdAB construct comprising the sdABs and a humanized Fc region (Nb-huFc) were produced as described in Stefan M A, et al.

The CDRs identified in the screening process can be provided in the form of an antibody. The antibody can have a useful form, such as one or more of the following domains: a single variable domain (VHH) or sdAB, a variable heavy domain (VH), a variable light domain (VL), a single-chain variable-fragment (scFv) antibody, a monoclonal antibody (mAb), an antigen-binding fragment (Fab), a fragment crystallizable region (Fc region), a heavy-chain only antibody (HcAb), an Immunoglobulin G (IgG) antibody, as well as bivalent, trivalent, tetravalent, multivalent, biparatropic, bispecific, multispecific chimeric, and humanized forms thereof. Any of the forms can include a linker between a first amino acid sequence (any domain herein, e.g., such as VH) and a second amino acid sequence (any domain herein, e.g. such as VL). In some embodiments, the sdAB has a molecular weight of 10 to 20 kDa, such as, e.g., 12 to 16 kDa, or 14 kDa to 15 kDa.

The sdAB construct includes a plurality of VHH domains, in which each VHH domain is different. Furthermore, each VHH domain can bind to the same target, the same portion of the same target, different targets, or different portions of the same target. Non-limiting targets are described herein.

FIG. 2 is a simplified illustration of an example sdAB construct in the form of a modified antibody. The sdAB construct comprises a first sdAB 201 and second sdAB 202. Each of the first and second sdABs comprise first and second binding regions, or first and second paratopes. The sdABs are heavy chains (VHH domains) that are coupled to a useful amino acid sequence, such as a Fc domain 205, e.g., a humanized Fc domain. The Fc domain, as shown, includes CH2 (211, 212) and CH3 (221, 222) domains. The VHH domains can be fused to other humanized forms of constant domains, such as Fc, CH1, CH2, CH3, and CL domains. Such VHH domains can also be fused to other forms, such as IgG1, IgG3, IgA, or IgM.

Yet other forms can include an Fc region and a Fab; or an Fc region and a VHH. The Fc region can include heavy chains present in any useful isotype (A, E, G, or M), such as Immunoglobulin G (e.g., IgG1, IgG2a, or IgG3). The Fab region can include domains from the heavy chains, including the variable heavy (VH) domains. Within the VH domain, CDRs can be configured to bind to a target of interest. The VHH domain can include CDRs configured to bind to a target of interest.

The first and second sdABs can be the same or different. In an embodiment, the first sdAB is configured to target to the lung tissue and the second sdAB is configured to act as a pharmaceutically or biochemically active agent. In an embodiment, both sdABs are configured for targeting the lung tissue (while still being the same or different) and another portion of the sdAB construct is configured to couple to a biochemical or pharmaceutically active cargo through linkage to the Fc domain.

The Fc region of the constructs herein can include a native immunoglobulin, i.e., as formed by the dimeric association of the respective Fc domains (or Fc moieties) of its two heavy chains, in which a native Fc region is homodimeric and comprises two polypeptide chains; or a genetically-fused Fc region or a single-chain Fc region (scFc region), in which a synthetic dimeric Fc region comprised of Fc domains (or Fc moieties) are genetically linked within a single polypeptide chain (i.e., encoded in a single contiguous genetic sequence) as described. In one embodiment, the construct includes a complete Fc region, whether present as one polypeptide chain (an scFc molecule) or in the wild-type form as two polypeptide chains.

The Fc region can include a hinge (e.g., upper, middle, and/or lower hinge region) domain, a CH2 domain, a CH3 domain, a CH4 domain, or a variant, portion, or fragment thereof. In other embodiments, an Fc moiety comprises a complete Fc domain (i.e., a hinge domain, a CH2 domain, and a CH3 domain). In one embodiment, a Fc moiety comprises a hinge domain (or portion thereof) fused to a CH3 domain (or portion thereof). In another embodiment, an Fc moiety comprises a CH2 domain (or portion thereof) fused to a CH3 domain (or portion thereof). In another embodiment, an Fc moiety consists of a CH3 domain or portion thereof. In another embodiment, an Fc moiety consists of a hinge domain (or portion thereof) and a CH3 domain (or portion thereof). In another embodiment, a Fc moiety consists of a CH2 domain (or portion thereof) and a CH3 domain. In another embodiment, a Fc moiety consists of a hinge domain (or portion thereof) and a CH2 domain (or portion thereof). In one embodiment, an Fc moiety lacks at least a portion of a CH2 domain (e.g., all or part of a CH2 domain).

In an embodiment, the Fc region includes an upper hinge, a core, and a lower hinge, connected in that order. The upper hinge is connected to the FR4 region of the sdAB and the lower hinge is connected to the human Fc region. These components may have the following sequences presented in Table 1, or a sequence having at least 90% sequence identity, such as at least 95%, or at least 98% sequence identity. In an exemplary embodiment, a sdAB coupled to a human Fc region is in accordance with SEQ ID NO: 406. In SEQ ID NO: 406, the upper hinge corresponds to SEQ ID NO: 401, the core is SEQ ID NO: 402, the lower hinge corresponds to SEQ ID NO: 403, and the mutated human Fc region is SEQ ID NO: 405. SEQ. ID. NO: 404 is non-mutated human Fc region. SEQ ID NO: 409 is an example sequence of a full sdAB plus Fc region with A as a linker between the fourth FR and the upper hinge. All SEQ ID NOS: 76-100 included A as a linker to the Fc region as tested in the Example below. In SEQ ID NO: 409 the Fc region is underlined, the A linker is bolded and underlined, and the CDRs are bolded.

complete heavy chains (such as, domain deleted antibodies or minibodies); engineered antibodies having synthetic linkers, such as any described herein; and multispecific forms of antibodies (e.g., bispecific, trispecific, etc., forms of any antibody, such as a sdAB) altered to bind to two or more different antigens, e.g., to a virus, such as a coronavirus and another therapeutically relevant target binding site, e.g., a lung tissue.

Modified antibodies can include other types of modifications, such as chemical modification (e.g., pegylation, glycosylation, lipidation, etc.), attachment to a particle or liposome, or bonding to a protein (e.g., a serum protein, a cytokine) or a cell (e.g., a CAR-T cell).

The constructs herein can be "chimeric" or "fusion" proteins. Such proteins comprise a first amino acid sequence linked to a second amino acid sequence to which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created using methods well known in the art, for example, by chemical synthesis, or by creating and translating a polynucleotide in which the peptide regions are encoded in the desired relationship.

Such forms or fusions can include a linker disposed between any number of domains, in which non-limiting

TABLE 1

| Description | SEQ ID NO: | Sequence |
|---|---|---|
| Upper Hinge | 401 | EPKSCDKTHT |
| Core | 402 | CPPC |
| Lower Hinge | 403 | PAPELLGGP |
| Human Fc Region | 404 | SVFLFPPKPKDTLMISRTPEVTCVVVDVSHEDPEVKFNW YVDGVEVHNAKTKPREEQYNSTYRVVSVLTVLHQD WLNGKEYKCKVSNKALPAPIEKTISKAKGQPREPQV YTLPPSRDELTKNQVSLTCLVKGFYPSDIA VEWESNG QPENNYKTTPPVLDSDGSFFLYSKLTVDKSRWQQGN VFSCSVMHEALHNHYTQKSLSLSPGK |
| Example SdAB coupled to human Fc Region | 409 | EVQLQASGGGFVQPGGSLRLSCAASGFAYSIDIMGWFRQAPGKEREF VSAISSWRGGPSKYADSVKGRFTISRDNSKNTVYLQMNSLRAEDTATYY CALTVDKGGSIYWGQGTQVTVSS<u>AEPKSCDKTHTCPPCPAPELLGGPSVFLF PPKPKDTLMISRTPEVTCVVVDVSHEDPEVKFNWYVDGVEVHNAKTKPREE QYNSTYRVVSVLTVLHQDWLNGKEYKCKVSNKALPAPIEKTISKAKGQPREP QVYTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGK</u> |

The Fc domains or moieties of a polypeptide may be from any isotype (A, E, G, or M) and may be derived from different immunoglobulin molecules. For example, an Fc domain or moiety of a polypeptide may comprise a $CH_2$ and/or $CH_3$ domain derived from an IgG1 molecule and a hinge region derived from an IgG3 molecule. In another example, an Fc domain or moiety can comprise a chimeric hinge region derived, in part, from an IgG1 molecule and, in part, from an IgG3 molecule. In another example, an Fc domain or moiety can comprise a chimeric hinge derived, in part, from an IgG1 molecule and, in part, from an IgG4 molecule.

The constructs herein can be modified antibodies, which includes synthetic forms of antibodies that are altered such that they are not naturally occurring, e.g., antibodies that comprise at least two heavy chain portions but not two linkers are described herein. Any useful linker can be employed, such as a peptide linker that can be cleavable or non-cleavable. Linkers can include or consist of a sequence according to the formula $[(Gly)_m(Ser)]_n(Gly)_p$, where each of m, n, and p is, independently, 0, 1, 2, 3, 4, 5, 6, 7, 8, 9, 10, 11, 12, 13, 14, 15, 16, 17, 18, 19, or 20. In some embodiments, m=1, 2, 3, 4, 5, or 6; n=1, 2, 3, 4, 5, 6, 7, 8, 9, or 10; and p=0, 1, 2, 3, or 4. Alternatively, the linker sequence includes or consists of a sequence according to the formula $(Gly)_p[(Ser)(Gly)_m]_n$, where each of m, n, and p is, independently, 0, 1, 2, 3, 4, 5, 6, 7, 8, 9, 10, 11, 12, 13, 14, 15, 16, 17, 18, 19, or 20. In some embodiments, m=1, 2, 3, 4, 5, or 6; n=1, 2, 3, 4, 5, 6, 7, 8, 9, or 10; and p=0, 1, 2, 3, or 4. In another embodiment, the linker sequence includes or consists of a sequence according to the formula $[(Gly)_m(Ser)(Gly)_p]_n$, where each of m, n, and p is, independently, 0, 1, 2, 3, 4, 5, 6, 7, 8, 9, 10, 11, 12, 13, 14, 15, 16, 17, 18, 19, or 20. In some embodiments, m=1, 2, 3, 4, 5, or 6; n=1, 2, 3, 4, 5, 6, 7, 8, 9, or 10; and p=0, 1, 2, 3, or 4. In an embodiment, a linker between the lung-targeting sdAB (e.g., FR4) and an upper hinge region is alanine (A). Further non-limiting linkers include any described herein, such as in SEQ ID NOs: 310-319 (Table 2).

TABLE 2

Example linkers

| Name | Sequence | SEQ ID NO: |
|---|---|---|
| $G_3$ | GGG | |
| $G_3S$ | GGGS | 311 |
| $G_4$ | GGGG | 312 |
| $G_4S$ | GGGGS | 313 |
| $G_2SG$ | GGSG | 314 |
| $(G_4S)_2$ | GGGGSGGGGS | 315 |
| $(G_4S)_3$ | GGGGSGGGGSGGGGS | 316 |
| $(G_4S)_4$ | GGGGSGGGGSGGGGSGGGGS | 317 |
| $(G_2SG)_2$ | GGSGGGSG | 318 |
| $(G_2SG)_3$ | GGSGGGSGGGSG | 319 |

The constructs can include other variations. Such variations can include one or more amino acids that facilitate humanization of an initial sequence. Humanization can include use of one or more amino acids present in a human form of the constant or variable regions (e.g., frameworks regions or CDRs). In other embodiments, the variation can include a sequence that lacks Cys and Met residues. In yet other embodiments, the CDR can have an altered length, such as a length from about 4-9 amino acids, 9-12 amino acids, or 12-15 amino acids.

In an embodiment, the sdAB construct can bind or couple to a target (e.g., any described herein or any lung tissue cell or submucosal structure), in which such binding can be characterized by analysis of lung tissue samples in mice. In an embodiment, the sdAB construct can bind a target (e.g., any described herein) and be characterized by immunohistochemistry (IHC) or ELISA. In an embodiment, a sdAB disclosed herein has a molecular weight of 20 kDa to 10 kDa, such as 16 kDa to 12 kDa, or 15 kDa to 11 kDa. Through the library screening process and testing disclosed herein 25 sdABs with affinity for targeting the lungs were identified.

In one embodiment, the lung targeting sdAB includes or is a polypeptide sequence having at least 90% sequence identity to any one of SEQ ID NOs: 76-100, such as at least 95%, or at least 98% sequence identity).

The sequence identity percent, as that term is used herein, includes fragments within the given sequence identity percent. Examples of fragments can include a polypeptide that is, e.g., one amino acid shorter than the reference CDR sequence selected from SEQ ID NOs: 1-75. In an embodiment, the omitted amino acid can be removed from the C-terminus. This omission of others can also be covered as an absent amino acid under a percent sequence identity calculation.

In an embodiment, a sdAB construct comprises a first binding domain, wherein the first binding domain comprises: a first complementarity determining region comprising a polypeptide sequence having at least 80% sequence identity to any one of SEQ ID NOs: 1-25; a second complementarity determining region comprising a polypeptide sequence having at least 80% sequence identity to any one of SEQ ID NOs: 26-50; and a third complementarity determining region comprising a polypeptide sequence having at least 80% sequence identity to any one of SEQ ID NOs: 51-75.

The binding domain can also be characterized by its binding affinity to a binding sequence. The terms "binding sequence," "binding domain," or "binding site", as used herein, refer to the portion, region, or site of polypeptide that mediates specific binding with a target molecule (e.g., a lung cell or a cell resident in the lung). Exemplary binding domains include an antigen binding site (e.g., a VHH or VH domain) or molecules comprising such a binding site (e.g., an antibody or a single domain antibody). A plurality of CDRs together form a binding domain for the sdAB construct, such as CDR1, CDR2, and CDR3.

In an embodiment, within the variable domain of the sdAB construct, three CDRs can be present. The CDRs can include a first CDR, a second CDR, and a third CDR. Any of these CDRs can be a polypeptide sequence having at least 80% sequence identity to any of SEQ ID NOs: 1-75. A fragment can be covered by the at least 80% sequence identity, for example, including a polypeptide that is one, two, or three amino acids shorter than the reference sequence of any of SEQ ID NOs: 1-75. The omitted amino acid(s) can be removed from the C-terminus and/or the N-terminus. Omitted amino acid(s) can also be included under the sequence identity percentage. In an embodiment, the sdAB construct is different in the first and second binding regions, and the first and second binding regions are different from each other and each binding region binds to a different epitope on a target disclosed herein.

The sdABs can be arranged in a structure including the CDRs disclosed herein, and corresponding to the structure disclosed in FIG. 4. Such sdAB sequences include framework regions FR1, FR2, FR3, and FR4, and CDR1, CDR2, and CDR3. In an embodiment, a sdAB construct comprises CDRs and framework regions (FRs). As can be seen, each CDR can be disposed between two FRs. An exemplary construct can include framework region 1 (FR1) attached to an N-terminus of CDR1; FR2 disposed between CDR1 and CD2; FR3 disposed between CDR2 and CDR3; and FR4 attached to a C-terminus of CDR3. Examples of sequences for CDR1, CDR2, and CDR3 include, e.g., any sequences for first CDR, second CDR, and third CDR, respectively, as described herein.

In an embodiment, the targeting or any other sdABs of the sdAB construct have a structure corresponding to FIG. 4 and comprises a polypeptide sequence having at least 90% sequence identity (such as at least 95% or at least 98%) to any one of SEQ ID NOs: 76-100 (FIG. 5 and FIG. 6). In another embodiment, the FR regions of the sdAB can be selected from those disclosed below, but the CDR regions are selected from those in any one of SEQ ID NOs: 1-75 (FIG. 3) and in the same order of CDR1, CDR2, and CDR3. Such sdABs have usefulness as targeting lung tissue and have shown greater selectivity to the lung over other organs.

In an embodiment, the sdABs are part of a sdAB construct comprising: a first and second sdAB and an Fc domain and hinge region of human IgG1 protein. The first and second sdABs comprise a first framework region coupled to a first complementarity determining region, a second framework region coupled to the first complementarity determining region and a second complementarity determining region, a third framework region coupled to the second complementarity determining region and a third complementarity determining region, and a fourth framework region coupled to the third complementary determining region. The first complementarity determining region comprises a polypeptide sequence having at least 80% sequence identity (such as at least 85% or at least 90%) to any one of SEQ ID NOs: 1-25; the second complementarity determining region comprising a polypeptide sequence having at least 80% sequence identity (such as at least 85% or at least 90%) to any one of SEQ ID NOs: 26-50; and the third complementarity determining region comprising a polypeptide sequence having at least 80% sequence identity (such as at least 85% or at least 90%) to any one of SEQ ID NOs: 51-75. The sdAB is coupled to the hinge region of the Fc domain.

Figure 7:
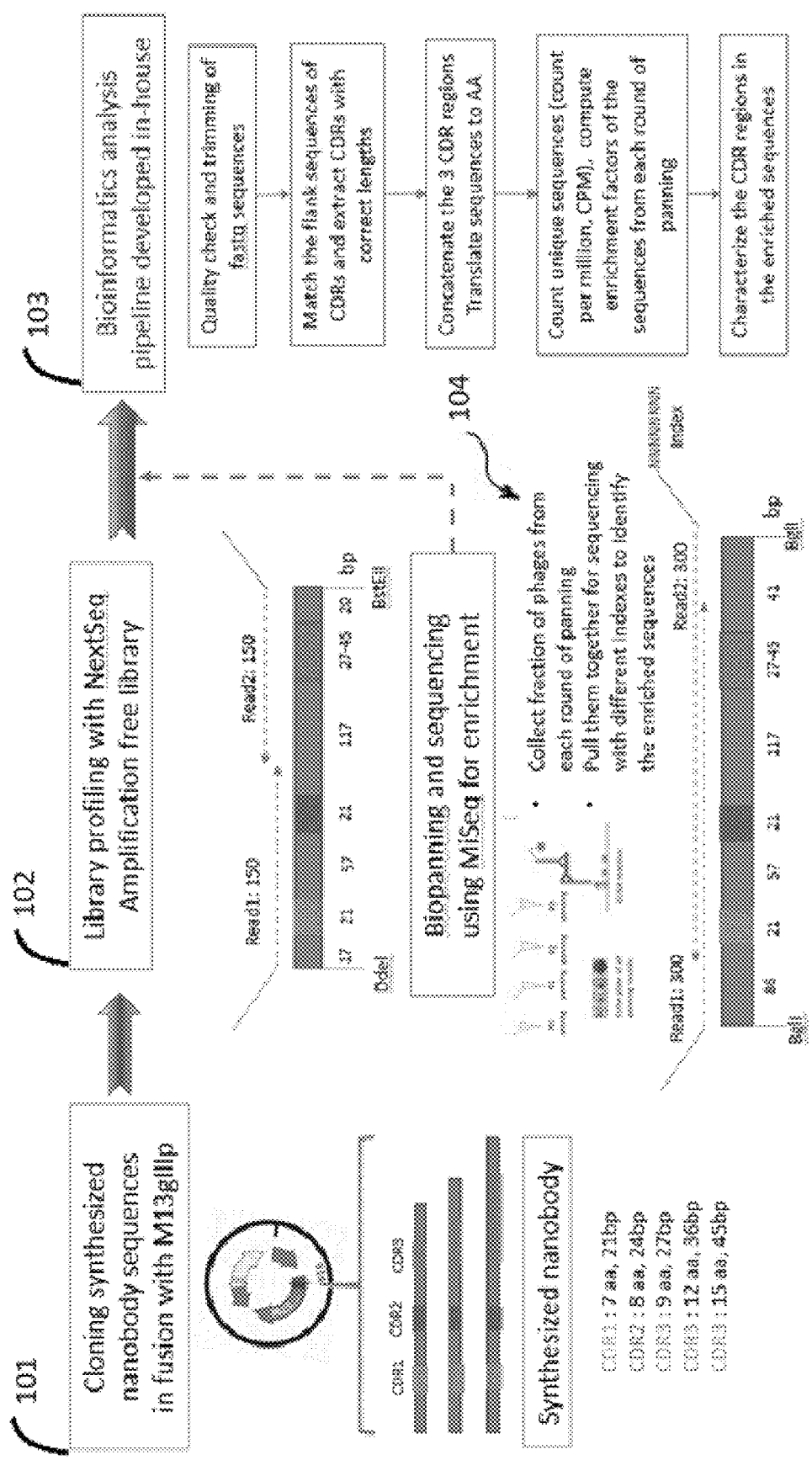
FIG. 7 is general schematic of exemplary library cloning, in vivo biopanning technique, and the bioinformatics analysis as disclosed herein.

FIG. 7 lists sequences for framework regions FR1, FR2, FR3, and FR4 (GGG, SEQ ID NOs. 311-313, respectively), which are disposed adjacent and/or between the regions indicated as CDR1, CDR2, and CDR3 as shown in FIG. 4. These framework regions are utilized in the examples herein.

FIG. 17 lists additional sequences for framework regions FR1, FR2, FR3, and FR4, which are disposed adjacent and/or between regions indicated as CDR1, CDR2, and CDR3 as shown in FIG. 4.

In an embodiment, the sdAB constructs herein include other FRs described herein. FIG. 18A provides non-limiting FR1 sequences. In some embodiments, the first FR includes or is a polypeptide sequence having at least 90% (such as at least 95% or at least 98%) sequence identity to SEQ ID NOs: 190-212.

FIG. 18B provides non-limiting FR2 sequences. In some embodiments, the second FR includes or is a polypeptide sequence having at least 90% (such as at least 95% or at least 98%) sequence identity to SEQ ID NOs: 220-243.

FIG. 18C provides non-limiting FR3 sequences. In some embodiments, the third FR includes or is a polypeptide sequence having at least 90% (such as at least 95% or at least 98%) sequence identity to SEQ ID NOs: 250-284.

FIG. 18D provides non-limiting FR4 sequences. In some embodiments, the fourth FR includes or is a polypeptide sequence having at least 90% (such as at least 95% or at least 98%) sequence identity to SEQ ID NOs: 290-301.

The sdAB construct may be expressed by a vector, such as a phage, yeast, mRNA, ribosomes, or a lentivirus. The phage is configured to express the sdAB with the binding domain comprising: a first complementarity determining region comprising a polypeptide sequence having at least 80% sequence identity to any one of SEQ ID NOs: 1-25; a second complementarity determining region comprising a polypeptide sequence having at least 80% sequence identity to any one of SEQ ID NOs: 26-50; and a third complementarity determining region comprising a polypeptide sequence having at least 80% sequence identity to any one of SEQ ID NOs: 51-75.

In an embodiment, the phage is a bacteriophage, such as a phage configured for the *E. coli* host, for example, T4, T7, Lambda, Fd, M3, M7, or M13 bacteriophage.

Figure 15:
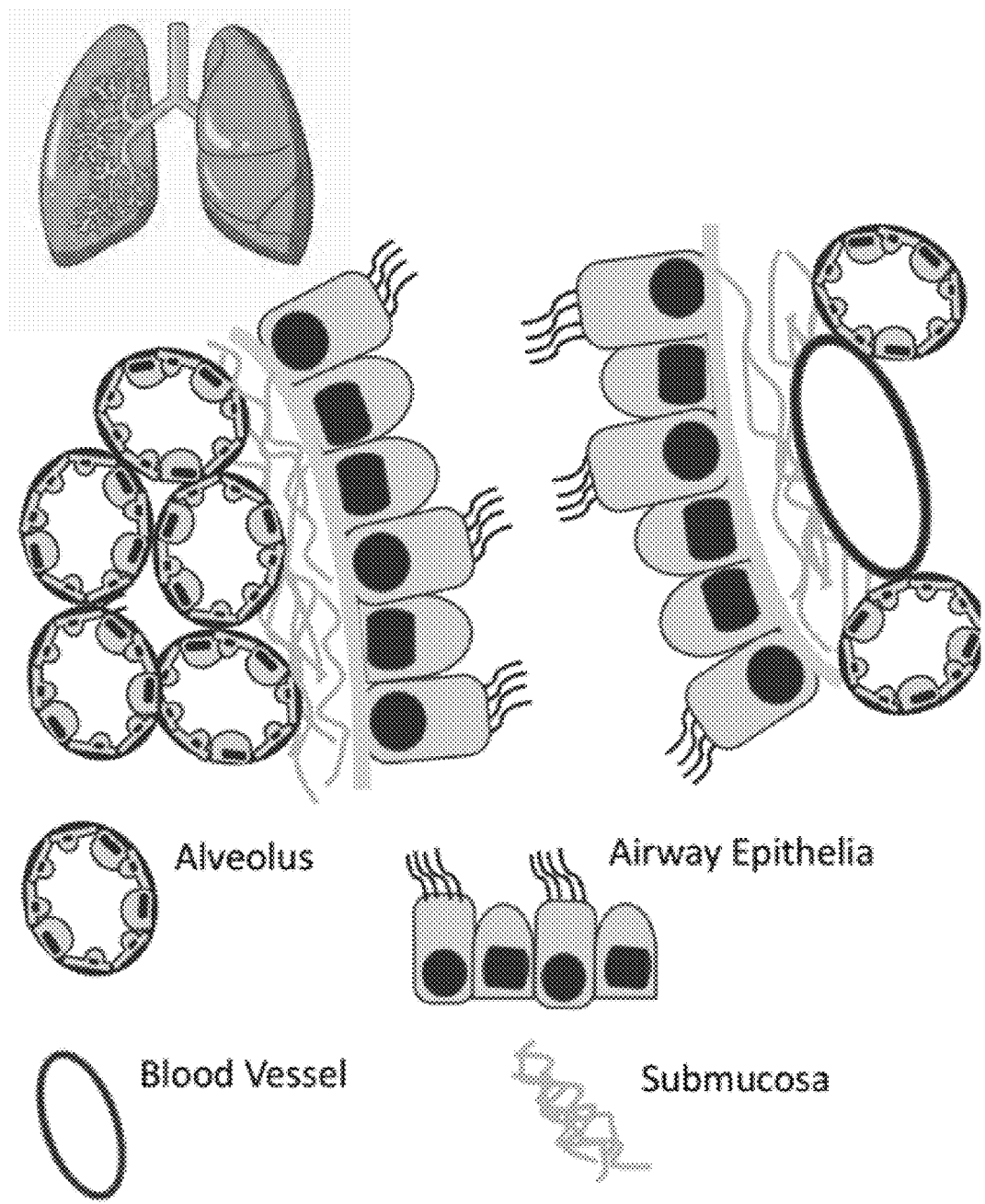
FIG. 15 is a graphic showing various example lung cell types.

The sdABs disclosed herein can include targets such as lung tissues, including cells or submucosal structures found in the human or mammal lungs. FIG. 15 generally shows cells found in the lungs. Cells found in the lungs include generally: (1) airway cells in bronchial and bronchiolar epithelium and bronchial glands (e.g., neuroendocrine, basal, ciliated, Clara, goblet, or submucosal glandular cells); (2) alveolar cells (e.g., Alveolar Epithelial Cells, AEC Type I, Type II, alveolar macrophages or fibroblasts in the interstitium); and (3) pulmonary vascular cells (endothelial cells smooth muscle cells, or adventitial fibroblasts). In particular, epitopes on these cell types may be primary targets for the sdAB shuttles disclosed herein.

A more specific listing of the cells found in the lungs, which the sdABs disclosed herein may target include:

Airway Epithelial Cells, selected from the group consisting of: goblet, ciliated, Clara cells, neuroendocrine (neuroendocrine bodies), basal, intermediate (or parabasal) cells, serous cell, brush cells, cells with numerous intracytoplasmic membrane-bound inclusions, oncocytes, nonciliated columnar cells, and metaplastic cells (squamous cells and Clara-mucous cells, bronchiolar metaplasia).

Alveolar cells selected from the group consisting of: type I and type II pneumocytes, cells at the transition between 1 and 2 consisting of cuboidal nonciliated cells, and alveolar macrophages.

Submucosal gland cells (in bronchi) selected from the group consisting of: serous cells, mucous cells, and ductal cells.

Interstitial connective tissue selected from the group consisting of: smooth muscle, cartilage, fibroblasts, myofibroblasts, meningothelioid cells of minute meningothelioid nodules, adipose tissue, and neural cells (intrapulmonary nerves).

Cells found in the blood vessels of the lungs selected from the group consisting of: endothelial cells (which have differences in arterioles versus veins versus capillaries), smooth muscle cells, fibroblasts/myofibroblasts, pericytes, and lymphatics (endothelial cells, smooth muscle cells, fibroblasts/myofibroblasts).

Cells found in the hematopoietic and lymphoid tissue selected from the group consisting of: lymphocytes, plasma cells, bronchial mucosal associated lymphoid tissue, megakaryocytes, macrophages, langerhans cells, mast cells, eosinophils, neutrophils, and basophils.

Cells found in the pleura selected from the group consisting of: mesothelial cell layer, pluripotent submesothelial fibroblasts, adipose cells—intrapleural fat, lymphatics (see above), stem cells, perivascular epithelioid cells (pec) (precursor for lam cells), pluripotent epithelial stem cell (precursor for lung cancer—especially small cell carcinoma), meningothelioid cells, endothelial progenitor cells, and mucinous cells in certain pediatric conditions.

A secondary target as disclosed herein is a target of the cargo of the sdAB construct, which can be an active biochemical species, such as another sdAB, or a pharmaceutical. The secondary target can be an antigen that can be bound by a sdAB construct described herein. Non-limiting targets include a virus, e.g., a coronavirus, a malignancy, such as cancer, or a bacterial infection.

Non-limiting portions of a coronavirus that may be a secondary target include SARS-CoV-2, includes a spike protein (e.g., a S-glycoprotein) or a receptor-binding domain (RBD).

The present disclosure encompasses a sdAB construct that can be directly or indirectly attached (i.e., coupled) to one or more therapeutic or diagnostic agents (cargo). Such agents can include a therapeutic antibody, a complementarity determining region (CDR) (e.g., from another sdAB), a small molecule drug, a chemotherapeutic agent, an antiviral agent, an antibacterial agent, an anti-inflammatory agent, a scavenging agent, an imaging agent, a marker, a dye, a detectable moiety, or a label.

Small size and water solubility of the sdAB construct are advantageous without additional attachments to promote delivery to the body, targeting lung tissue, and circulation within the body. The sdAB attached to a humanized Fc still provides solubility and targeting benefits, but also promotes signaling the body's own immune response and keeping the sdAB circulating in the blood stream without being filtered out by the kidneys.

Any of the constructs herein (e.g., sdABs, sdABs bound to humanized Fc) can be employed to bind to a target. Binding can be accomplished, e.g., by using CDRs specific for that target, such as those disclosed herein. In one embodiment, the construct includes one or more CDRs for viral targets. Exemplary targets include a virus, such as Coronaviridae (e.g., severe acute respiratory syndrome-related coronavirus (SARS-CoV), severe acute respiratory syndrome coronavirus 2 (SARS-CoV-2), or variants thereof); or a portion of a virus, such as a spike protein or a receptor-binding domain (RBD) of a coronavirus.

Other non-limiting therapeutic or diagnostic agents include a nucleic acid (e.g., oligonucleotides, polynucleotides, nucleotides, nucleosides, molecules of DNA, or molecules of RNA, including a chromosome, a plasmid, a viral genome, a primer, or a gene); a protein (e.g., a glycoprotein, a metalloprotein, an enzyme, a prion, or an immunoglobulin); a metabolite; a sugar; a lipid; or a lipopolysaccharide.

Non-limiting detectable moieties for diagnostic agents may be a radioisotope (e.g., $^{32}P$), a fluorescent or chemiluminescent compound such as rhodamine or luciferin, or an enzyme, such as alkaline phosphatase or horseradish peroxidase. Non-limiting labels include a radiolabel, an isotope, a visible or near-infrared fluorescent label, a reporter molecule, or biotin.

The therapeutic or diagnostic agent can be a peptide, an enzyme (e.g., horseradish peroxidase, alkaline phosphatase, glucose-6-phosphatase or Beta-galactosidase), a nucleic acid, a virus, a fluorophore (e.g., green fluorescent protein (GFP), blue fluorescent dyes excited at wavelengths in the ultraviolet (UV) part of the spectrum (e.g., AMCA (7-amino-4-methylcoumarin-3-acetic acid); Alexa Fluor 350), green fluorescent dyes excited by blue light (e.g., FITC, CY2 (cyanine dye), ALEXA FLUOR 488 (fluorescent dye)), red fluorescent dyes excited by green light (e.g., rhodamines, TEXAS RED (sulforhodamine 101 acid chloride), CY3 (cyanine dye), ALEXA FLUOR 546, 564 and 594 (fluorescent dyes)), or dyes excited with far-red light (e.g., CY5 (cyanine dye)) to be visualized with electronic detectors (CCD cameras, photomultipliers)), a heavy metal (including chelates thereof, such as those including europium, lanthanum or yttrium), a chemical entity, or a radioisotope (e.g., [$^{18}F$]fluorodeoxy glucose, $^{11}C$-, $^{125}I$-, $^{131}I$-, $^{3}H$-, $^{14}C$-, $^{35}S$-, or $^{99}Tc$-labelled compounds).

The therapeutic or diagnostic agent can include a drug, an antigen binding fragment of an antibody molecule or portion thereof (e.g., F(ab), scFv, a VH domain, or a VL domain) (e.g., to impart, induce or block a biological response), a ligand binding portion of a receptor or a receptor binding portion of a ligand, an enzyme, therapeutically useful amino acids, peptides, proteins, nucleic acids, including but not limited to polynucleotides, oligonucleotides, carbohydrates and lipids. Yet other exemplary agents include cytokines, neurotrophic factors, growth factors, enzymes, antibodies, neurotransmitters, neuromodulators, antibiotics, antiviral agents, antifungal agents, imaging or detectable agents, isotopes, and chemotherapeutic agents, and the like. The therapeutic or diagnostic agents can also include drugs, prodrugs, and precursors that can be activated when the therapeutic agent is delivered to the target tissue.

The present disclosure also encompasses methods that employ any construct described herein. In particular embodiments, the methods include methods of treatment or prophylaxis of one or more diseases, malignancies, or conditions.

Methods can also include use of the construct as a therapeutic or diagnostic agent, which can be administered to a subject (a mammal or a human) by inhalation, oral, nasal, injection, intravenous, intraperitoneal, intramuscular or subcutaneous injection. The constructs herein (e.g., with a therapeutic or diagnostic agent) can be used in imaging, identifying or diagnosing diseases or malignancies, or in diagnosing viral spread.

Methods can also include providing a construct or a pharmaceutical composition thereof (e.g., as described herein) for use in the treatment of viral infections or any malignancy or condition herein. A pharmaceutical composition can include any construct, described herein either with a therapeutic or diagnostic agent, and a pharmaceutically acceptable carrier.

As used herein, "pharmaceutically acceptable carrier" is intended to include pharmaceutically acceptable salts, adjuvants, dispersion media, coatings, antibacterial and antifungal agents, isotonic and absorption delaying agents, and the like, compatible with pharmaceutical administration. Pharmaceutically acceptable salts include the acid addition salts (formed with the free amino groups of the polypeptide or antibody molecule) which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like. Suitable carriers include those disclosed in the most recent edition of Remington's Pharmaceutical Sciences, a standard reference text in the field. Preferred examples of such carriers or diluents include, but are not limited to, water, saline, Ringer's solutions, dextrose solution, and 5% human serum albumin. Liposomes, cationic lipids and non-aqueous vehicles such as fixed oils may also be used. The use of such media and agents for pharmaceutically active substances is well known in the art. Except insofar as any conventional media or agent is incompatible with a therapeutic agent as defined hereabove, use thereof in the composition of the present invention is contemplated.

In an embodiment, nanoparticles such as those disclosed in U.S. 2019/0091150 may be part of the sdAB construct, wherein the shuttle sdAB is a cargo on the nanoparticle and another cargo is associated with the same construct.

For performing the in vivo biopanning methods were developed for concentrating and purifying the phage library so that the living organisms could better process the phage/sdABs. To this end, an isoelectric precipitation and endotoxin removal step were employed.

In an embodiment, lysate of the phagemid cells comprising DNA inserts of a sequence configured to allow for expression of the sdAB, e.g., the sdABs disclosed herein are mixed with an acid, such as a strong acid, e.g., HCl. (See FIG. 8, 802.) The addition of acid may reduce the pH of the solution by 1 to 3 pH, such as 1.25 to 2.5, or 1.5 to 2 pH. In an embodiment, the initial pH of the solution is 5 to 7 pH, such as, 5.5 to 6.5 or about 6.0.

This causes an isoelectric precipitation in the solution, resulting in a precipitate of the lysate. Precipitation can be encouraged by gravimetric means, such as centrifugation.

After isolation of the precipitate, it can be resuspended and precipitated multiple times with a polar liquid, e.g., sterilized water. After 1 to 5, e.g., 2 to 3 resuspension steps, the suspended product in polar liquid can be stored with refrigeration and pH can be adjusted to 6.5 to 7.5 pH, or approximately neutral.

In an endotoxin removal step, a nonionic surfactant, such as TRITON-X-114 (a secondary alcohol ethoxylate, non-ionic surfactant) is added to neutralize endotoxins in the purified phage lysate sample. Other endotoxin removal agents can be used instead of or in addition to the nonionic surfactant, for example, an organic solvent such as 1-octanol, or an enzymatic inactivating agent using alkaline phosphatase. The resulting mixture can be mixed, e.g., vortexed. Optionally, the process can be accelerated by alternately cooling and heating. For example, cooling can be with an ice bath or freezer, at just above freezing (near 32° F.) to 45° F., e.g., 33° F. to 40° F. for cooling such as with an ice bath. Heating, for example, can be performed in a heat block set at, e.g., 30° C. to 50° C., such as, e.g., 35 to 40° C., or about 37° C. Heating and cooling intervals may be, for example, be 2 to 15 minutes, such as 3 to 10 minutes, or about 5 minutes each. An amount of 1% endotoxin removal agent can be used. In an embodiment, 0.1 to 5% endotoxin removal agent may be used, such as, e.g., 0.5% to 1.5%, or 0.75% to 1.25%.

The suspension should look cloudy when finished. The cloudy suspension can then be separated, for example, with gravimetric means, such as centrifuging, and at elevated temperature, such as 30° C. to 50° C., such as, e.g., 35 to 40° C., or about 37° C. Separation should produce a supernatant at the top of the tube and an oily residue at the bottom at the tube. The final product is the purified and concentrated sdAB encoding phage derived from the library.

EXAMPLES

Example 1: SdAB Development and Library

A high-diversity synthetic sdAB phage library was used to identify humanized sdABs that show affinity to lung tissue. In particular, a high diversity humanized sdAB library (more than $3 \times 10^{10}$ sdAB variants) was developed and designed to have three different CDR3 lengths and incorporated the natural prevalence of amino acids at specific CDR positions for CDR1 and CDR2 derived from numerous effective sdABs. For CDR3, all amino acids were used with the exception of cysteine and methionine. The sequence used for the framework to house the custom made CDRs, hs2dAb, was derived from Moutel et al. In this framework, multiple residues are changed such that the framework more closely mirrors germline human VH3 immunoglobin. To obtain sufficient diversity coverage for the library (i.e., transformants), 150 electroporations were performed yielding approximately $3.38 \times 10^{10}$ transformants. To determine the level of success for the ligation of the library into the vector backbone, colony PCR was performed. Of the 408 colonies selected, 395 contained the correct size amplified DNA fragment (95.9%). This value was used to adjust the calculated value for library diversity to $3.24 \times 10^{10}$. Finally, library diversity, quality, and the distribution of CDR3 lengths were assessed by NGS from a total of 39,870,360 reads. The 9-amino acid CDR3 was the most prevalent at 40%, followed by 12-amino acid CDR3 at 34%, and lastly the 15-amino acid CDR3 at 25% of the observed diversity. Overall, there was good coverage of all represented CDR3s. Approximately 1% of sequences contained a stop codon and 99% of reads were unique sequences (38,592,027 reads). Roughly 1% of reads were duplicates, and 0.01% (1,095 sequences) were present in triplicate. With these corrections the adjusted diversity for this sdAB library is $3.18 \times 10^{10}$.

FIG. 1 generally discloses a method of constructing a sdAB phage library. In particular, the library was constructed using novel DNA synthesis technology, thereby ensuring high quality and full length sdABs with low incidence of stop codons. These attributes allowed for the identification of highly potent binders to desired targets with femtomolar to nanomolar dissociation constants.

Example 2

FIG. 7 shows an overview of the process by which the sdABs from the library were sequenced and enriched for determination of interaction with the lung tissue.

At 101, library was developed by cloning into the pADL20c M13 phagemid vector, which allows for expression of sdABs as a fusion protein to coat protein gIIIp of M13 phage. To display sdAB on M13 phage, the phagemids were constructed with pADL20c as backbone template and with synthesized DNA inserts of the sdAB sequences which were designed by incorporating the natural prevalence of amino acids at positions in CDR1, CDR2 and highly diversified CDR3 with 3 different lengths (9-, 12-, and 15-amino acids).

At 102, library profiling and enriched sequence analysis was performed. Next generation sequencing was performed to evaluate the diversity of the phage library and identify the enriched sequences enrichment from the rounds of biopanning. (See Example 3.) The minimum region containing all 3 CDR domains, approximately 300 bps, was excised by two-step restriction digests, BglI followed by DdeI/BstEII double digests on the gel-purified small fragment from the BglI restriction reaction to cover the entire length of CDR sequences. The sequencing library was prepared with unique indexes for each sample and sequenced on Illumina NextSeq 500/550 platform with High Output v2.5 300-cycles, paired-end mode.

At 103, bioinformatic analysis of the library was performed. Raw sequencing files of the library were converted to FASTQ and demultiplexed by the index sequences. The sequences were processed with quality filtering (Q>=30) and adaptor trimming using fastp with the following parameters, -q 30 -l 100 -x 7. The processed sequences were reformatted to be reverse complemented and merged with R1 Read using BBTools (BBMap). Sequences were aligned by conserved region and variable regions extracted. Three CDR domains with correct sequence lengths were extracted, concatenated and translated using a custom python script. The normalized abundance was calculated per million sequences for each round of panning and enriched sequence analysis was performed using a custom R script. Sequence counts that are 5 and less were removed and normalized by total reads of each sample per million. The sequences were further filtered by one and above in the enrichment factor, normalized counts of the third round (R3) divided by normalized count of the second round (R2) panning. The CDR3 sequences were clustered to find common motifs.

Example 3

The following steps were taken to scale up the sdAB library and purify it for use in in vivo bio-panning. First, three reagents were made for the steps discussed below.

1. SMPB 5.8 g of NaCl, 2 g of MgSO4, 50 mL of 1M Tris-HCl (pH 7.5) were mixed, and the volume was brough to to 1 L and put in an autoclave set at 121° C. for 20 minutes.

2. LB TA (Lysogeny Broth Top Agar).

25 g of LB broth, 5 g of agar were mixed in 1 L of $H_2O$. Then the mixture was put in an autoclave.

3. 2.5 M NaCl/20% PEG-8000

100 g PEG-8000 (20% w/v) and 75 g NaCl (2.5M) were dissolved in 400 mL $H_2O$ and brought to final volume of 500 mL. This was filtered and sterilized.

Phage Spot Titer

100 µL of TG1 *E. coli* bacteria were mixed with 3 mL of LB TA (as described above) in a 14 mL tube and pipetted onto an LB agar plate (1 plate per titer). These were allowed to dry for about 10-20 minutes. A 10-fold serial dilution of phage was performed (for CM13 dilution out to $10^{-10}$) in SMPB (formula for SMPB is described above). CM13 is an interference resistant helper phage engineered for phage display and is available from Antibody Design Labs of San Diego, CA.

3 µL of each dilution were spotted onto the plate and allowed to dry about 20 minutes, then incubated, agar side down, at 37° C. overnight.

The next day results were viewed and one or more spots had individual plaques. The individual plaques were counted. Titer calculation: titer=pfu/µL spotted*1000*dilution factor.

Phage Full Plate Titer

100 µL aliquots of TG1 were added into 14 mL tubes for each dilution planned for plating. A 10-fold serial dilution of phage was conducted in SMPB.

Then each tube of TG1 was infected with 100 µL of an appropriate dilution of phage and swirled. (CM13 was diluted to $10^{-6}$ to $10^{-10}$). Infection was performed for 15 minutes at room temperature (e.g., 72° C.). Then 3 mL of LB TA were added to mix the bacteria/phage infection and then plated onto LB agar. The plates were allowed to dry for about 20 minutes, incubate agar side up overnight at 37° C.

Plaques on all plates were counted and titer was calculated as above.

Plate Lysates

A web plate was taken from a previous full plate titer. 8 mL of SMPB were added and this was allowed to sit for 4 hours at room temperature. The liquid was removed with a syringe, and filtered with a 0.2 µM filter.

Liquid Growth of CM13

20 mL of 2×YT media (available from Sigma Aldrich) were added to 200 µL of a TG1 *E. coli* bacteria culture grown overnight, and 1 µl of CM13 (titer >$10^{10}$). The mixture was shaken at 37° C. for 4 hours. This was then spun at 4500×g for 10 minutes.

Large Scale Phage Precipitation 16 mL of supernatant were transferred to a new tube and 4 mL of 2.5 M NaCl/20% PEG-8000 (w/v) were added and mixed briefly. Phage was allowed to precipitated for 1 hr to overnight (e.g., 11 to 16 hours) at 4° C. (1 hr, 4 hr, and overnight were all performed with good results). This can be done at other volumes with a ratio of about 4:1 lysate to PEG, e.g., 2:1 to 8:1, or 3:1 to 5:1.

Phage was pelleted by centrifugation at 12000×g for 15 min. Supernatant was decanted and the pellet was resuspend in 1 mL TBS and transferred to an Eppendorf tube. The tube was spun for 30 seconds at max speed. Then the supernatant was removed to a new tube and titered. (See FIG. 8, 801.)

Isoelectric Precipitation 5 mL of CM13 lysate was swirled to mix with 29 µL of 6N HCl. (See FIG. 8, 802.) The initial pH was about 6.0 and between 4.0 and 4.5 after HCl addition using pH strips.

The mixture was spun at 10,000×g for 10 min at 20° C. The supernatant was removed with a serological pipette (decanting is also an option). A white pellet was visible along the side of the 50 mL conical tube.

1 mL of filter-sterilized milli-Q water was added and the pellet was vortexed for 1 minute to resuspend it, and spin at 10,000×g for 10 min at 20° C.

Again, the supernatant was removed and the pellet resuspended in 500 µL filter-sterilized milli-Q water. The pH was adjusted to about 7.0 with 1 µL of ION NaOH and stored at 4° C.

Endotoxin Removal

5 µL of TRITON-X-114 (a secondary alcohol ethoxylate, nonionic surfactant) was added to 500 µL of phage lysate from the isoelectric precipitation above. This was mixed in a tube (vortexed) for 20 seconds. (See FIG. 8, 803.)

The tube was placed in an ice bath for 5 minutes and vortexed for 5 seconds every minute for the 5 minutes. The tube was then placed in a heat block set at 37° C. for 5 minutes. The solution was very cloudy when finished. The cloudy solution was then spun at 37° C. 20,000×g for 30 seconds. (There was an oily droplet at the bottom at the tube.)

6.400 µL were removed from the top of the tube being very careful to not disturb the oily droplet. This final product was the purified and concentrated sdAB encoding phage from the library.

The table of FIG. 9 shows the titers of the CM13 phage at the various stages shown in FIG. 8 and the original library stock as received from the lab. The phage was concentrated and purified with a final product titer of $1 \times 10^{1}4$.

Example 4

Figure 12:
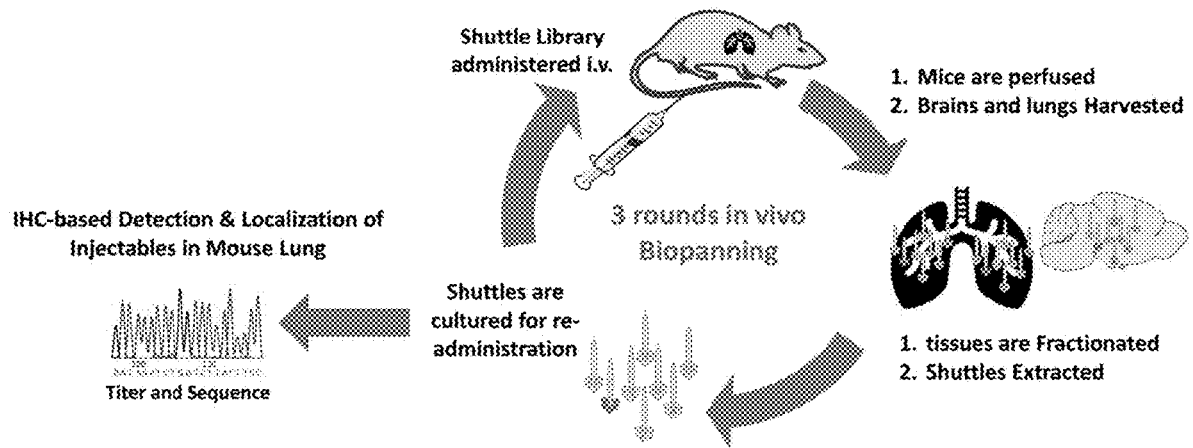
FIG. 12 is a schematic showing the in vivo biopanning technique used in the Examples herein.

The purified final product of Example 3 was then used for in vivo bio-panning in mice (See FIG. 7, step 104, FIG. 8, step 804, and FIG. 12). FIG. 12 shows the general process of the in vivo biopanning wherein the sdAB constructs are described as shuttles. The purified and concentrated library was intravenously injected into five mice. The lungs were dissociated, and the phage was extracted, grown up, and re-purified. The reprocessed lung-phages were re-injected into five mice two additional times (harvested and reprocessed as described above) to ensure lung-targeting sdAB enrichment in the lung above other tissues.

The mouse lungs were harvested one-hour later. For harvesting, the mice were anesthetized using isoflurane. Transcardial perfusion with cold, heparinized saline was performed by inserting a butterfly needle into the left ventricle and clipping a lobe of the liver for drainage; perfusion media was conducted using a peristaltic pump. The organs were harvested and kept on ice for analysis and processing.

FIG. 10 shows data of phage populations at each round of in vivo biopanning and shows the input and output CFUs for each round. The output sample was sequenced to gauge enrichment and selection over time. From this in vivo biopanning campaign 25 top candidate sdABs for lung-targeting were identified. These correspond to SEQ ID NOs: 76-100.

FIG. 11 is a table showing the functional enrichment of the top 25 sequences in Round 2 and Round 3 biopanning in terms of enrichment factor.

By the end of the third round of biopanning 30805 sdABs (28118 of which were unique) found in the lung had been reduced down to a total of 744 (735 of which were unique). Furthermore, the final sequences had been enriched 10 fold or higher.

Example 5

Figure 13:
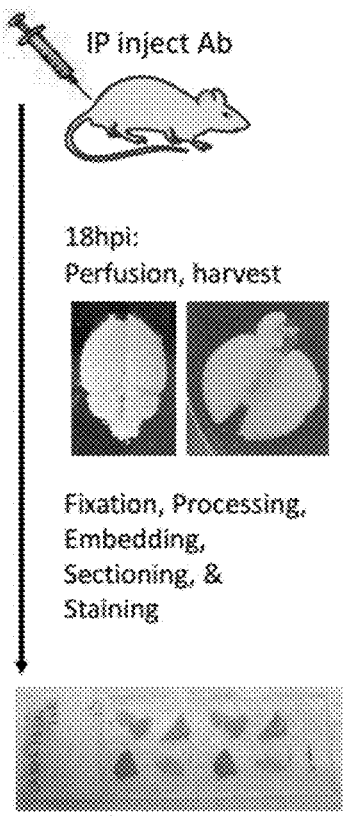
FIG. 13 is a timeline showing more detail on the steps of the biopanning technique used in the Examples.

Further confirmation screening using sdAB-human Fc fusion protein versions of these 25 candidates was also performed by intraperitoneal (IP) injection into mice (3 mice per sdAB, for a total of 75 individuals), and after 18 hours, perfusion and harvesting of the mouse lungs and other tissues was performed. Then after fixation, processing, embedding, and sectioning, validation by immunohistochemistry staining was performed (see FIG. 13). The staining analysis showed spatial and temporal lung-targeting efficacy of several of the tested sdAB constructs of SEQ ID NOS: 76-100.

Figure 14:
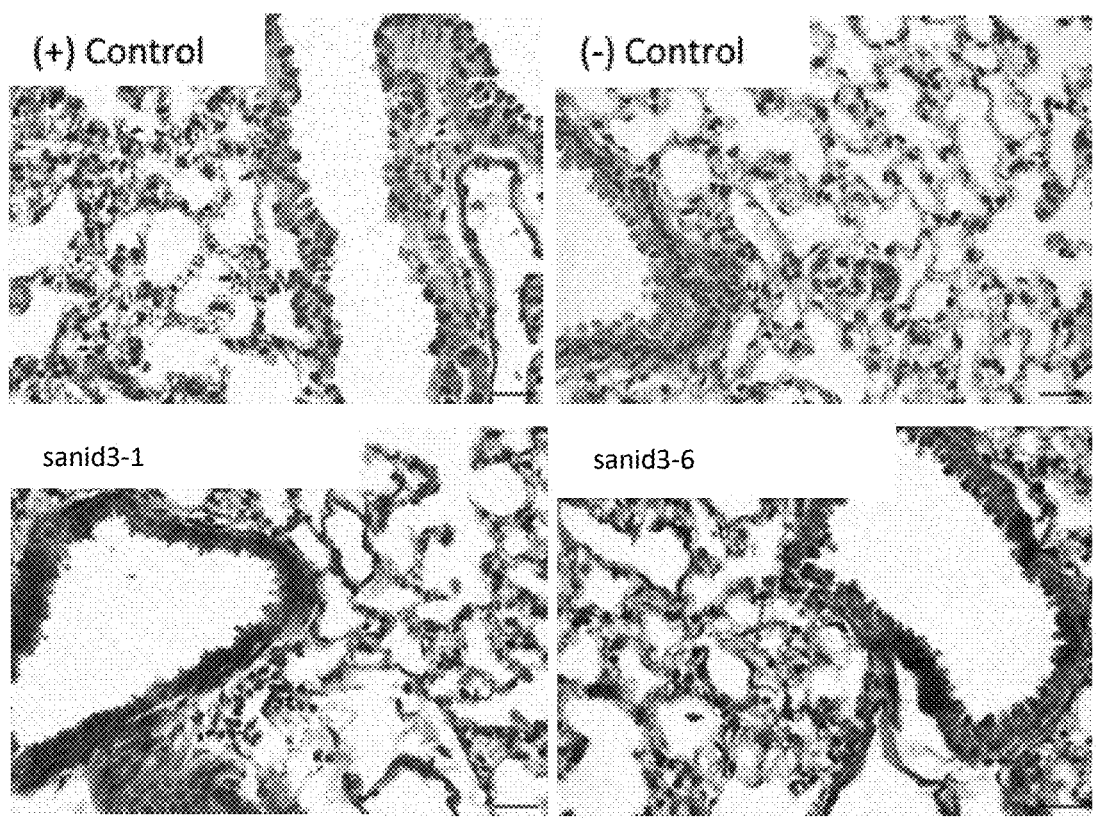
FIG. 14 shows at the top two panels: positive and negative controls of immunohistograms; and in the bottom two panels lung immunohistograms for two of the Examples.

FIG. 14 discloses positive and negative controls as well as representative images of specific, positive staining in the lung for two different sdABs present in the lungs of all three mice tested for each sdAB. The same sdABs were not found to be enriched in other tissues that were also analyzed, indicating that the enrichment was specific to the lungs.

All publications, patents, and patent applications mentioned in this specification are incorporated herein by reference to the same extent as if each independent publication or patent application was specifically and individually indicated to be incorporated by reference.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the detailed description or the claims, such a term is intended to be inclusive in a manner similar to the term "comprising" as "comprising" is interpreted when employed as a transitional word in a claim. The term "consisting essentially" as used herein means the specified materials or steps and those that do not materially affect the basic and novel characteristics of the material or method. Unless the context indicates otherwise, all percentages and averages are by weight. If not specified above, the properties mentioned herein may be determined by applicable ASTM standards, or if an ASTM standard does not exist for the property, the most commonly used standard known by those of skill in the art may be used. The articles "a," "an," and "the," should be interpreted to mean "one or more" unless the context indicates the contrary.

The invention claimed is:

1. A single-domain antibody construct, comprising a first single-domain antibody with a binding domain, wherein the binding domain comprises:
 a first polypeptide comprising first, second, and third complementarity determining regions selected from the group consisting of the following combinations:
 SEQ ID NOs: 1, 26, and 51, respectively;
 SEQ ID NOs: 2, 27, and 52, respectively;
 SEQ ID NOs: 3, 28, and 53, respectively;
 SEQ ID NOs: 4, 29, and 54, respectively;
 SEQ ID NOs: 5, 30, and 55, respectively;
 SEQ ID NOs: 6, 31, and 56, respectively;
 SEQ ID NOs: 7, 32, and 57, respectively;
 SEQ ID NOs: 8, 33, and 58, respectively;
 SEQ ID NOs: 9, 34, and 59, respectively;
 SEQ ID NOs: 10, 35, and 60, respectively;
 SEQ ID NOs: 11, 36, and 61, respectively;
 SEQ ID NOs: 12, 37, and 62, respectively;
 SEQ ID NOs: 13, 38, and 63, respectively;
 SEQ ID NOs: 14, 39, and 64, respectively;
 SEQ ID NOs: 15, 40, and 65, respectively;
 SEQ ID NOs: 16, 41, and 66, respectively;
 SEQ ID NOs: 17, 42, and 67, respectively;
 SEQ ID NOs: 18, 43, and 68, respectively;
 SEQ ID NOs: 19, 44, and 69, respectively;
 SEQ ID NOs: 20, 45, and 70, respectively;
 SEQ ID NOs: 21, 46, and 71, respectively;
 SEQ ID NOs: 22, 47, and 72, respectively;
 SEQ ID NOs: 23, 48, and 73, respectively;
 SEQ ID NOs: 24, 49, and 74, respectively; and
 SEQ ID NOs: 25, 50, and 75, respectively.

2. The single-domain antibody construct of claim 1, further comprising one or more therapeutic or diagnostic agents.

3. The single-domain antibody construct of claim 1, further comprising a therapeutic agent selected from the group consisting of: a therapeutic antibody, a small molecule drug, a chemotherapeutic agent, an antiviral agent, an antibacterial agent, an anti-inflammatory agent, and a scavenging agent.

4. The single-domain antibody construct of claim 1, further comprising a diagnostic agent selected from the group consisting of: an imaging agent, a marker, a dye, a detectable moiety, and a label.

5. The single-domain antibody construct of claim 1, further comprising a second single-domain antibody with a second binding domain, wherein the binding domain is configured to target lung cells; and the second binding domain is configured to treat or diagnose a disease or malignancy.

6. The single-domain antibody construct of claim 1, further comprising a therapeutic agent with antiviral activity against a coronavirus.

7. The single-domain antibody construct of claim 1, wherein the single-domain antibody further comprises:
 a first framework region attached to an N-terminus of the first complementarity determining region;
 a second framework region disposed between the first and second complementarity determining regions;
 a third framework region disposed between the second and third complementarity determining regions; and
 a fourth framework region attached to a C-terminus of the third complementarity determining region.

8. The single-domain antibody construct of claim 1, wherein the first single-domain antibody is a polypeptide sequence having at least 99% sequence identity to any one of SEQ ID NOs: 76-100.

9. The single-domain antibody construct of claim 1, wherein the first single-domain antibody comprises a first, second, third, and fourth framework region selected from the group consisting of the following combinations:
SEQ ID NOs.: 191, 221, 252, and 290, respectively; and
SEQ ID NOs: 190, 220, 251, and 290, respectively.

10. The single-domain antibody construct of claim 8, wherein the first single-domain antibody is a polypeptide sequence corresponding to any one of SEQ ID NOs: 76-100.

11. The single-domain antibody construct of claim 1, wherein the binding domain is configured to target mouse lung tissue.

12. The single-domain antibody construct of claim 11, wherein the lung tissue comprises a cell selected from the group consisting of: airway cells in bronchial and bronchiolar epithelium, bronchial gland cells, alveolar cells, pulmonary vascular cells, and submucosal cells.

13. The single-domain antibody construct of claim 1, wherein the single-domain antibody construct is expressed as a fusion protein coating protein gIIIp of M13 phage.

14. The single-domain antibody construct of claim 1, wherein the first polypeptide comprising first, second, and third complementarity determining regions is selected from the group consisting of the following combinations:
SEQ ID NOs: 1, 26, and 51, respectively; and
SEQ ID NOs: 2, 27, and 52, respectively.

15. The single-domain antibody construct of claim 1, wherein the first polypeptide comprising first, second, and third complementarity determining regions is selected from the group consisting of the following combinations:
SEQ ID NOs: 3, 28, and 53, respectively;
SEQ ID NOs: 4, 29, and 54, respectively;
SEQ ID NOs: 5, 30, and 55, respectively;
SEQ ID NOs: 6, 31, and 56, respectively;
SEQ ID NOs: 7, 32, and 57, respectively;
SEQ ID NOs: 8, 33, and 58, respectively; and
SEQ ID NOs: 9, 34, and 59, respectively.

16. The single-domain antibody construct of claim 1, wherein the first polypeptide comprising first, second, and third complementarity determining regions is selected from the group consisting of the following combinations:
SEQ ID NOs: 11, 36, and 61, respectively;
SEQ ID NOs: 12, 37, and 62, respectively;
SEQ ID NOs: 13, 38, and 63, respectively;
SEQ ID NOs: 14, 39, and 64, respectively;
SEQ ID NOs: 15, 40, and 65, respectively;
SEQ ID NOs: 16, 41, and 66, respectively;
SEQ ID NOs: 17, 42, and 67, respectively;
SEQ ID NOs: 18, 43, and 68, respectively;
SEQ ID NOs: 19, 44, and 69, respectively;
SEQ ID NOs: 20, 45, and 70, respectively;
SEQ ID NOs: 21, 46, and 71, respectively;
SEQ ID NOs: 22, 47, and 72, respectively;
SEQ ID NOs: 23, 48, and 73, respectively;
SEQ ID NOs: 24, 49, and 74, respectively; and
SEQ ID NOs: 25, 50, and 75, respectively.

17. A vector comprising:
a phage configured to express a single-domain antibody with a binding domain, wherein the binding domain comprises:
a first polypeptide comprising first, second, and third complementarity determining regions selected from the group consisting of the following combinations:
SEQ ID NOs: 1, 26, and 51, respectively;
SEQ ID NOs: 2, 27, and 52, respectively;
SEQ ID NOs: 3, 28, and 53, respectively;
SEQ ID NOs: 4, 29, and 54, respectively;
SEQ ID NOs: 5, 30, and 55, respectively;
SEQ ID NOs: 6, 31, and 56, respectively;
SEQ ID NOs: 7, 32, and 57, respectively;
SEQ ID NOs: 8, 33, and 58, respectively;
SEQ ID NOs: 9, 34, and 59, respectively;
SEQ ID NOs: 10, 35, and 60, respectively;
SEQ ID NOs: 11, 36, and 61, respectively;
SEQ ID NOs: 12, 37, and 62, respectively;
SEQ ID NOs: 13, 38, and 63, respectively;
SEQ ID NOs: 14, 39, and 64, respectively;
SEQ ID NOs: 15, 40, and 65, respectively;
SEQ ID NOs: 16, 41, and 66, respectively;
SEQ ID NOs: 17, 42, and 67, respectively;
SEQ ID NOs: 18, 43, and 68, respectively;
SEQ ID NOs: 19, 44, and 69, respectively;
SEQ ID NOs: 20, 45, and 70, respectively;
SEQ ID NOs: 21, 46, and 71, respectively;
SEQ ID NOs: 22, 47, and 72, respectively;
SEQ ID NOs: 23, 48, and 73, respectively;
SEQ ID NOs: 24, 49, and 74, respectively; and
SEQ ID NOs: 25, 50, and 75, respectively.

18. The vector of claim 17, wherein the phage comprises an M13 bacteriophage.

19. The vector of claim 17, wherein the single-domain antibody is expressed as a fusion protein to coat protein gIIIp of M13 bacteriophage.

20. The vector of claim 17, wherein the first polypeptide comprising first, second, and third complementarity determining regions is selected from the group consisting of the following combinations:
SEQ ID NOs: 1, 26, and 51, respectively; and
SEQ ID NOs: 2, 27, and 52, respectively.

* * * * *

SEQUENCE LISTING

```
Sequence total quantity: 409
SEQ ID NO: 1             moltype = AA  length = 7
FEATURE                  Location/Qualifiers
REGION                   1..7
                         note = Synthetic
source                   1..7
                         mol_type = protein
                         organism = synthetic construct
SEQUENCE: 1
GTYSITH                                                                  7

SEQ ID NO: 2             moltype = AA  length = 7
FEATURE                  Location/Qualifiers
REGION                   1..7
                         note = Synthetic
source                   1..7
                         mol_type = protein
                         organism = synthetic construct
SEQUENCE: 2
RTFQQDG                                                                  7

SEQ ID NO: 3             moltype = AA  length = 7
FEATURE                  Location/Qualifiers
REGION                   1..7
                         note = Synthetic
source                   1..7
                         mol_type = protein
                         organism = synthetic construct
SEQUENCE: 3
GTFDQYT                                                                  7

SEQ ID NO: 4             moltype = AA  length = 7
FEATURE                  Location/Qualifiers
REGION                   1..7
                         note = Synthetic
source                   1..7
                         mol_type = protein
                         organism = synthetic construct
SEQUENCE: 4
TFFSFQG                                                                  7

SEQ ID NO: 5             moltype = AA  length = 7
```

-continued

```
FEATURE              Location/Qualifiers
REGION               1..7
                     note = Synthetic
source               1..7
                     mol_type = protein
                     organism = synthetic construct
SEQUENCE: 5
GTSRSYH                                                                 7

SEQ ID NO: 6         moltype = AA  length = 7
FEATURE              Location/Qualifiers
REGION               1..7
                     note = Synthetic
source               1..7
                     mol_type = protein
                     organism = synthetic construct
SEQUENCE: 6
FAYSIDI                                                                 7

SEQ ID NO: 7         moltype = AA  length = 7
FEATURE              Location/Qualifiers
REGION               1..7
                     note = Synthetic
source               1..7
                     mol_type = protein
                     organism = synthetic construct
SEQUENCE: 7
STFQYSD                                                                 7

SEQ ID NO: 8         moltype = AA  length = 7
FEATURE              Location/Qualifiers
REGION               1..7
                     note = Synthetic
source               1..7
                     mol_type = protein
                     organism = synthetic construct
SEQUENCE: 8
STFSGYH                                                                 7

SEQ ID NO: 9         moltype = AA  length = 7
FEATURE              Location/Qualifiers
REGION               1..7
                     note = Synthetic
source               1..7
                     mol_type = protein
                     organism = synthetic construct
SEQUENCE: 9
GPFSGYD                                                                 7

SEQ ID NO: 10        moltype = AA  length = 7
FEATURE              Location/Qualifiers
REGION               1..7
                     note = Synthetic
source               1..7
                     mol_type = protein
                     organism = synthetic construct
SEQUENCE: 10
RTFTAVW                                                                 7

SEQ ID NO: 11        moltype = AA  length = 7
FEATURE              Location/Qualifiers
REGION               1..7
                     note = Synthetic
source               1..7
                     mol_type = protein
                     organism = synthetic construct
SEQUENCE: 11
RTFDTWD                                                                 7

SEQ ID NO: 12        moltype = AA  length = 7
FEATURE              Location/Qualifiers
REGION               1..7
                     note = Synthetic
source               1..7
                     mol_type = protein
                     organism = synthetic construct
SEQUENCE: 12
QTFSQFT                                                                 7
```

```
SEQ ID NO: 13          moltype = AA  length = 7
FEATURE                Location/Qualifiers
REGION                 1..7
                       note = Synthetic
source                 1..7
                       mol_type = protein
                       organism = synthetic construct
SEQUENCE: 13
GADGEYS                                                                  7

SEQ ID NO: 14          moltype = AA  length = 7
FEATURE                Location/Qualifiers
REGION                 1..7
                       note = Synthetic
source                 1..7
                       mol_type = protein
                       organism = synthetic construct
SEQUENCE: 14
RISSDYD                                                                  7

SEQ ID NO: 15          moltype = AA  length = 7
FEATURE                Location/Qualifiers
REGION                 1..7
                       note = Synthetic
source                 1..7
                       mol_type = protein
                       organism = synthetic construct
SEQUENCE: 15
GTFREYQ                                                                  7

SEQ ID NO: 16          moltype = AA  length = 7
FEATURE                Location/Qualifiers
REGION                 1..7
                       note = Synthetic
source                 1..7
                       mol_type = protein
                       organism = synthetic construct
SEQUENCE: 16
QFFSIST                                                                  7

SEQ ID NO: 17          moltype = AA  length = 7
FEATURE                Location/Qualifiers
REGION                 1..7
                       note = Synthetic
source                 1..7
                       mol_type = protein
                       organism = synthetic construct
SEQUENCE: 17
RIFSHYR                                                                  7

SEQ ID NO: 18          moltype = AA  length = 7
FEATURE                Location/Qualifiers
REGION                 1..7
                       note = Synthetic
source                 1..7
                       mol_type = protein
                       organism = synthetic construct
SEQUENCE: 18
GTYQIYS                                                                  7

SEQ ID NO: 19          moltype = AA  length = 7
FEATURE                Location/Qualifiers
REGION                 1..7
                       note = Synthetic
source                 1..7
                       mol_type = protein
                       organism = synthetic construct
SEQUENCE: 19
QTSTFQP                                                                  7

SEQ ID NO: 20          moltype = AA  length = 7
FEATURE                Location/Qualifiers
REGION                 1..7
                       note = Synthetic
source                 1..7
                       mol_type = protein
                       organism = synthetic construct
SEQUENCE: 20
QPFGIYG                                                                  7
```

```
SEQ ID NO: 21              moltype = AA   length = 7
FEATURE                    Location/Qualifiers
REGION                     1..7
                           note = Synthetic
source                     1..7
                           mol_type = protein
                           organism = synthetic construct
SEQUENCE: 21
RSFSDYI                                                                    7

SEQ ID NO: 22              moltype = AA   length = 7
FEATURE                    Location/Qualifiers
REGION                     1..7
                           note = Synthetic
source                     1..7
                           mol_type = protein
                           organism = synthetic construct
SEQUENCE: 22
TTFQRSD                                                                    7

SEQ ID NO: 23              moltype = AA   length = 7
FEATURE                    Location/Qualifiers
REGION                     1..7
                           note = Synthetic
source                     1..7
                           mol_type = protein
                           organism = synthetic construct
SEQUENCE: 23
RAFGIYR                                                                    7

SEQ ID NO: 24              moltype = AA   length = 7
FEATURE                    Location/Qualifiers
REGION                     1..7
                           note = Synthetic
source                     1..7
                           mol_type = protein
                           organism = synthetic construct
SEQUENCE: 24
FSFRYYG                                                                    7

SEQ ID NO: 25              moltype = AA   length = 7
FEATURE                    Location/Qualifiers
REGION                     1..7
                           note = Synthetic
source                     1..7
                           mol_type = protein
                           organism = synthetic construct
SEQUENCE: 25
RADSWQD                                                                    7

SEQ ID NO: 26              moltype = AA   length = 8
FEATURE                    Location/Qualifiers
REGION                     1..8
                           note = Synthetic
source                     1..8
                           mol_type = protein
                           organism = synthetic construct
SEQUENCE: 26
DWGSPSTY                                                                   8

SEQ ID NO: 27              moltype = AA   length = 8
FEATURE                    Location/Qualifiers
REGION                     1..8
                           note = Synthetic
source                     1..8
                           mol_type = protein
                           organism = synthetic construct
SEQUENCE: 27
SQQQNWVY                                                                   8

SEQ ID NO: 28              moltype = AA   length = 8
FEATURE                    Location/Qualifiers
REGION                     1..8
                           note = Synthetic
source                     1..8
                           mol_type = protein
                           organism = synthetic construct
SEQUENCE: 28
```

```
SWSGSFAY                                                                        8

SEQ ID NO: 29           moltype = AA  length = 8
FEATURE                 Location/Qualifiers
REGION                  1..8
                        note = Synthetic
source                  1..8
                        mol_type = protein
                        organism = synthetic construct
SEQUENCE: 29
SFTDGSTY                                                                        8

SEQ ID NO: 30           moltype = AA  length = 8
FEATURE                 Location/Qualifiers
REGION                  1..8
                        note = Synthetic
source                  1..8
                        mol_type = protein
                        organism = synthetic construct
SEQUENCE: 30
GGTGGNGW                                                                        8

SEQ ID NO: 31           moltype = AA  length = 8
FEATURE                 Location/Qualifiers
REGION                  1..8
                        note = Synthetic
source                  1..8
                        mol_type = protein
                        organism = synthetic construct
SEQUENCE: 31
SWRGGPSK                                                                        8

SEQ ID NO: 32           moltype = AA  length = 8
FEATURE                 Location/Qualifiers
REGION                  1..8
                        note = Synthetic
source                  1..8
                        mol_type = protein
                        organism = synthetic construct
SEQUENCE: 32
STRGHWTY                                                                        8

SEQ ID NO: 33           moltype = AA  length = 8
FEATURE                 Location/Qualifiers
REGION                  1..8
                        note = Synthetic
source                  1..8
                        mol_type = protein
                        organism = synthetic construct
SEQUENCE: 33
RSSGTFTY                                                                        8

SEQ ID NO: 34           moltype = AA  length = 8
FEATURE                 Location/Qualifiers
REGION                  1..8
                        note = Synthetic
source                  1..8
                        mol_type = protein
                        organism = synthetic construct
SEQUENCE: 34
STSAHWTY                                                                        8

SEQ ID NO: 35           moltype = AA  length = 8
FEATURE                 Location/Qualifiers
REGION                  1..8
                        note = Synthetic
source                  1..8
                        mol_type = protein
                        organism = synthetic construct
SEQUENCE: 35
RTSGDWAH                                                                        8

SEQ ID NO: 36           moltype = AA  length = 8
FEATURE                 Location/Qualifiers
REGION                  1..8
                        note = Synthetic
source                  1..8
                        mol_type = protein
                        organism = synthetic construct
```

```
SEQUENCE: 36
SRSGNWTY                                                                        8

SEQ ID NO: 37           moltype = AA  length = 8
FEATURE                 Location/Qualifiers
REGION                  1..8
                        note = Synthetic
source                  1..8
                        mol_type = protein
                        organism = synthetic construct
SEQUENCE: 37
ASSGKSTD                                                                        8

SEQ ID NO: 38           moltype = AA  length = 8
FEATURE                 Location/Qualifiers
REGION                  1..8
                        note = Synthetic
source                  1..8
                        mol_type = protein
                        organism = synthetic construct
SEQUENCE: 38
SATGSFTY                                                                        8

SEQ ID NO: 39           moltype = AA  length = 8
FEATURE                 Location/Qualifiers
REGION                  1..8
                        note = Synthetic
source                  1..8
                        mol_type = protein
                        organism = synthetic construct
SEQUENCE: 39
RRTSQWTY                                                                        8

SEQ ID NO: 40           moltype = AA  length = 8
FEATURE                 Location/Qualifiers
REGION                  1..8
                        note = Synthetic
source                  1..8
                        mol_type = protein
                        organism = synthetic construct
SEQUENCE: 40
AGQGHATY                                                                        8

SEQ ID NO: 41           moltype = AA  length = 8
FEATURE                 Location/Qualifiers
REGION                  1..8
                        note = Synthetic
source                  1..8
                        mol_type = protein
                        organism = synthetic construct
SEQUENCE: 41
SWRDKTTH                                                                        8

SEQ ID NO: 42           moltype = AA  length = 8
FEATURE                 Location/Qualifiers
REGION                  1..8
                        note = Synthetic
source                  1..8
                        mol_type = protein
                        organism = synthetic construct
SEQUENCE: 42
HQSQHTQY                                                                        8

SEQ ID NO: 43           moltype = AA  length = 8
FEATURE                 Location/Qualifiers
REGION                  1..8
                        note = Synthetic
source                  1..8
                        mol_type = protein
                        organism = synthetic construct
SEQUENCE: 43
SWTGFSTY                                                                        8

SEQ ID NO: 44           moltype = AA  length = 8
FEATURE                 Location/Qualifiers
REGION                  1..8
                        note = Synthetic
source                  1..8
                        mol_type = protein
```

```
                                organism = synthetic construct
SEQUENCE: 44
SRYGQSYY                                                                        8

SEQ ID NO: 45           moltype = AA   length = 8
FEATURE                 Location/Qualifiers
REGION                  1..8
                        note = Synthetic
source                  1..8
                        mol_type = protein
                        organism = synthetic construct
SEQUENCE: 45
SRQGFTVQ                                                                        8

SEQ ID NO: 46           moltype = AA   length = 8
FEATURE                 Location/Qualifiers
REGION                  1..8
                        note = Synthetic
source                  1..8
                        mol_type = protein
                        organism = synthetic construct
SEQUENCE: 46
SRTAWWAW                                                                        8

SEQ ID NO: 47           moltype = AA   length = 8
FEATURE                 Location/Qualifiers
REGION                  1..8
                        note = Synthetic
source                  1..8
                        mol_type = protein
                        organism = synthetic construct
SEQUENCE: 47
QAAQGWTY                                                                        8

SEQ ID NO: 48           moltype = AA   length = 8
FEATURE                 Location/Qualifiers
REGION                  1..8
                        note = Synthetic
source                  1..8
                        mol_type = protein
                        organism = synthetic construct
SEQUENCE: 48
GSDGGHVL                                                                        8

SEQ ID NO: 49           moltype = AA   length = 8
FEATURE                 Location/Qualifiers
REGION                  1..8
                        note = Synthetic
source                  1..8
                        mol_type = protein
                        organism = synthetic construct
SEQUENCE: 49
HQSGGWTY                                                                        8

SEQ ID NO: 50           moltype = AA   length = 8
FEATURE                 Location/Qualifiers
REGION                  1..8
                        note = Synthetic
source                  1..8
                        mol_type = protein
                        organism = synthetic construct
SEQUENCE: 50
QRAQHWTY                                                                        8

SEQ ID NO: 51           moltype = AA   length = 15
FEATURE                 Location/Qualifiers
REGION                  1..15
                        note = Synthetic
source                  1..15
                        mol_type = protein
                        organism = synthetic construct
SEQUENCE: 51
LARWEQSQNV FRRSW                                                               15

SEQ ID NO: 52           moltype = AA   length = 9
FEATURE                 Location/Qualifiers
REGION                  1..9
                        note = Synthetic
source                  1..9
```

```
                            mol_type = protein
                            organism = synthetic construct
SEQUENCE: 52
HIQPGQVAE                                                                    9

SEQ ID NO: 53               moltype = AA   length = 9
FEATURE                     Location/Qualifiers
REGION                      1..9
                            note = Synthetic
source                      1..9
                            mol_type = protein
                            organism = synthetic construct
SEQUENCE: 53
QLVDGKRKG                                                                    9

SEQ ID NO: 54               moltype = AA   length = 9
FEATURE                     Location/Qualifiers
REGION                      1..9
                            note = Synthetic
source                      1..9
                            mol_type = protein
                            organism = synthetic construct
SEQUENCE: 54
HIQPGQVTP                                                                    9

SEQ ID NO: 55               moltype = AA   length = 9
FEATURE                     Location/Qualifiers
REGION                      1..9
                            note = Synthetic
source                      1..9
                            mol_type = protein
                            organism = synthetic construct
SEQUENCE: 55
THFNWQNVR                                                                    9

SEQ ID NO: 56               moltype = AA   length = 9
FEATURE                     Location/Qualifiers
REGION                      1..9
                            note = Synthetic
source                      1..9
                            mol_type = protein
                            organism = synthetic construct
SEQUENCE: 56
LTVDKGGSI                                                                    9

SEQ ID NO: 57               moltype = AA   length = 9
FEATURE                     Location/Qualifiers
REGION                      1..9
                            note = Synthetic
source                      1..9
                            mol_type = protein
                            organism = synthetic construct
SEQUENCE: 57
NIQVNQFSD                                                                    9

SEQ ID NO: 58               moltype = AA   length = 9
FEATURE                     Location/Qualifiers
REGION                      1..9
                            note = Synthetic
source                      1..9
                            mol_type = protein
                            organism = synthetic construct
SEQUENCE: 58
ESADWIVPN                                                                    9

SEQ ID NO: 59               moltype = AA   length = 9
FEATURE                     Location/Qualifiers
REGION                      1..9
                            note = Synthetic
source                      1..9
                            mol_type = protein
                            organism = synthetic construct
SEQUENCE: 59
FWEWRATNH                                                                    9

SEQ ID NO: 60               moltype = AA   length = 9
FEATURE                     Location/Qualifiers
REGION                      1..9
                            note = Synthetic
```

-continued

```
source                    1..9
                          mol_type = protein
                          organism = synthetic construct
SEQUENCE: 60
HVRPGGPHI                                                                      9

SEQ ID NO: 61             moltype = AA   length = 9
FEATURE                   Location/Qualifiers
REGION                    1..9
                          note = Synthetic
source                    1..9
                          mol_type = protein
                          organism = synthetic construct
SEQUENCE: 61
PNLQCNIQI                                                                      9

SEQ ID NO: 62             moltype = AA   length = 9
FEATURE                   Location/Qualifiers
REGION                    1..9
                          note = Synthetic
source                    1..9
                          mol_type = protein
                          organism = synthetic construct
SEQUENCE: 62
GKTHNSAKF                                                                      9

SEQ ID NO: 63             moltype = AA   length = 12
FEATURE                   Location/Qualifiers
REGION                    1..12
                          note = Synthetic
source                    1..12
                          mol_type = protein
                          organism = synthetic construct
SEQUENCE: 63
FPLHDQGGGK KL                                                                 12

SEQ ID NO: 64             moltype = AA   length = 9
FEATURE                   Location/Qualifiers
REGION                    1..9
                          note = Synthetic
source                    1..9
                          mol_type = protein
                          organism = synthetic construct
SEQUENCE: 64
WFGSLLGLF                                                                      9

SEQ ID NO: 65             moltype = AA   length = 12
FEATURE                   Location/Qualifiers
REGION                    1..12
                          note = Synthetic
source                    1..12
                          mol_type = protein
                          organism = synthetic construct
SEQUENCE: 65
SYRWDTSSTQ PE                                                                 12

SEQ ID NO: 66             moltype = AA   length = 9
FEATURE                   Location/Qualifiers
REGION                    1..9
                          note = Synthetic
source                    1..9
                          mol_type = protein
                          organism = synthetic construct
SEQUENCE: 66
VKATTGRSF                                                                      9

SEQ ID NO: 67             moltype = AA   length = 9
FEATURE                   Location/Qualifiers
REGION                    1..9
                          note = Synthetic
source                    1..9
                          mol_type = protein
                          organism = synthetic construct
SEQUENCE: 67
VRTDNGEYY                                                                      9

SEQ ID NO: 68             moltype = AA   length = 12
FEATURE                   Location/Qualifiers
REGION                    1..12
```

```
                        note = Synthetic
source                  1..12
                        mol_type = protein
                        organism = synthetic construct
SEQUENCE: 68
DFGRAYNGQV NV                                                            12

SEQ ID NO: 69           moltype = AA  length = 15
FEATURE                 Location/Qualifiers
REGION                  1..15
                        note = Synthetic
source                  1..15
                        mol_type = protein
                        organism = synthetic construct
SEQUENCE: 69
VLHNTNQSED IDYTQ                                                         15

SEQ ID NO: 70           moltype = AA  length = 9
FEATURE                 Location/Qualifiers
REGION                  1..9
                        note = Synthetic
source                  1..9
                        mol_type = protein
                        organism = synthetic construct
SEQUENCE: 70
VLQWQTADV                                                                 9

SEQ ID NO: 71           moltype = AA  length = 9
FEATURE                 Location/Qualifiers
REGION                  1..9
                        note = Synthetic
source                  1..9
                        mol_type = protein
                        organism = synthetic construct
SEQUENCE: 71
FEQNIDTWY                                                                 9

SEQ ID NO: 72           moltype = AA  length = 9
FEATURE                 Location/Qualifiers
REGION                  1..9
                        note = Synthetic
source                  1..9
                        mol_type = protein
                        organism = synthetic construct
SEQUENCE: 72
FVAASGIST                                                                 9

SEQ ID NO: 73           moltype = AA  length = 12
FEATURE                 Location/Qualifiers
REGION                  1..12
                        note = Synthetic
source                  1..12
                        mol_type = protein
                        organism = synthetic construct
SEQUENCE: 73
KWNHDKDHES RI                                                            12

SEQ ID NO: 74           moltype = AA  length = 15
FEATURE                 Location/Qualifiers
REGION                  1..15
                        note = Synthetic
source                  1..15
                        mol_type = protein
                        organism = synthetic construct
SEQUENCE: 74
VLQTTEQKIF EDYIN                                                         15

SEQ ID NO: 75           moltype = AA  length = 15
FEATURE                 Location/Qualifiers
REGION                  1..15
                        note = Synthetic
source                  1..15
                        mol_type = protein
                        organism = synthetic construct
SEQUENCE: 75
RLPAFSGNAR SPYDN                                                         15

SEQ ID NO: 76           moltype = AA  length = 125
FEATURE                 Location/Qualifiers
```

```
REGION                  1..125
                        note = Synthetic
source                  1..125
                        mol_type = protein
                        organism = synthetic construct
SEQUENCE: 76
EVQLQASGGG FVQPGGSLRL SCAASGGTYS ITHMGWFRQA PGKEREFVSA ISDWGSPSTY   60
YADSVKGRFT ISRDNSKNTV YLQMNSLRAE DTATYYCALA RWEQSQNVFR RSWYWGQGTQ  120
VTVSS                                                              125

SEQ ID NO: 77           moltype = AA  length = 119
FEATURE                 Location/Qualifiers
REGION                  1..119
                        note = Synthetic
source                  1..119
                        mol_type = protein
                        organism = synthetic construct
SEQUENCE: 77
EVQLQASGGG FVQPGGSLRL SCAASGRTFQ QDGMGWFRQA PGKEREFVSA ISSQQQNWVY   60
YADSVKGRFT ISRDNSKNTV YLQMNSLRAE DTATYYCAHI QPGQVAEYWG QGTQVTVSS   119

SEQ ID NO: 78           moltype = AA  length = 119
FEATURE                 Location/Qualifiers
REGION                  1..119
                        note = Synthetic
source                  1..119
                        mol_type = protein
                        organism = synthetic construct
SEQUENCE: 78
EVQLQASGGG FVQPGGSLRL SCAASGGTFD QYTMGWFRQA PGKEREFVSA ISSWSGSFAY   60
YADSVKGRFT ISRDNSKNTV YLQMNSLRAE DTATYYCAQL VDGKRKGYWG QGTQVTVSS   119

SEQ ID NO: 79           moltype = AA  length = 119
FEATURE                 Location/Qualifiers
REGION                  1..119
                        note = Synthetic
source                  1..119
                        mol_type = protein
                        organism = synthetic construct
SEQUENCE: 79
EVQLQASGGG FVQPGGSLRL SCAASGTFFS FQGMGWFRQA PGKEREFVSA ISSFTDGSTY   60
YADSVKGRFT ISRDNSKNTV YLQMNSLRAE DTATYYCAHI QPGQVTPYWG QGTQVTVSS   119

SEQ ID NO: 80           moltype = AA  length = 119
FEATURE                 Location/Qualifiers
REGION                  1..119
                        note = Synthetic
source                  1..119
                        mol_type = protein
                        organism = synthetic construct
SEQUENCE: 80
EVQLQASGGG FVQPGGSLRL SCAASGGTSR SYHMGWFRQA PGKEREFVSA ISGGTGGNGW   60
YADSVKGRFT ISRDNSKNTV YLQMNSLRAE DTATYYCATH FNWQNVRYWG QGTQVTVSS   119

SEQ ID NO: 81           moltype = AA  length = 119
FEATURE                 Location/Qualifiers
REGION                  1..119
                        note = Synthetic
source                  1..119
                        mol_type = protein
                        organism = synthetic construct
SEQUENCE: 81
EVQLQASGGG FVQPGGSLRL SCAASGFAYS IDIMGWFRQA PGKEREFVSA ISSWRGGPSK   60
YADSVKGRFT ISRDNSKNTV YLQMNSLRAE DTATYYCALT VDKGGSIYWG QGTQVTVSS   119

SEQ ID NO: 82           moltype = AA  length = 119
FEATURE                 Location/Qualifiers
REGION                  1..119
                        note = Synthetic
source                  1..119
                        mol_type = protein
                        organism = synthetic construct
SEQUENCE: 82
EVQLQASGGG FVQPGGSLRL SCAASGSTFQ YSDMGWFRQA PGKEREFVSA ISSTRGHWTY   60
YADSVKGRFT ISRDNSKNTV YLQMNSLRAE DTATYYCANI QVNQFSDYWG QGTQVTVSS   119

SEQ ID NO: 83           moltype = AA  length = 119
FEATURE                 Location/Qualifiers
REGION                  1..119
```

```
                              note = Synthetic
source                        1..119
                              mol_type = protein
                              organism = synthetic construct
SEQUENCE: 83
EVQLQASGGG FVQPGGSLRL SCAASGSTFS GYHMGWFRQA PGKEREFVSA ISRSSGTFTY    60
YADSVKGRFT ISRDNSKNTV YLQMNSLRAE DTATYYCAES ADWIVPNYWG QGTQVTVSS    119

SEQ ID NO: 84                 moltype = AA   length = 119
FEATURE                       Location/Qualifiers
REGION                        1..119
                              note = Synthetic
source                        1..119
                              mol_type = protein
                              organism = synthetic construct
SEQUENCE: 84
EVQLQASGGG FVQPGGSLRL SCAASGGPFS GYDMGWFRQA PGKEREFVSA ISSTSAHWTY    60
YADSVKGRFT ISRDNSKNTV YLQMNSLRAE DTATYYCAFW EWRATNHYWG QGTQVTVSS    119

SEQ ID NO: 85                 moltype = AA   length = 119
FEATURE                       Location/Qualifiers
REGION                        1..119
                              note = Synthetic
source                        1..119
                              mol_type = protein
                              organism = synthetic construct
SEQUENCE: 85
EVQLQASGGG FVQPGGSLRL SCAASGRTFT AVWMGWFRQA PGKEREFVSA ISRTSGDWAH    60
YADSVKGRFT ISRDNSKNTV YLQMNSLRAE DTATYYCAHV RPGGPHIYWG QGTQVTVSS    119

SEQ ID NO: 86                 moltype = AA   length = 119
FEATURE                       Location/Qualifiers
REGION                        1..119
                              note = Synthetic
source                        1..119
                              mol_type = protein
                              organism = synthetic construct
SEQUENCE: 86
EVQLQASGGG FVQPGGSLRL SCAASGRTFD TWDMGWFRQA PGKEREFVSA ISSRSGNWTY    60
YADSVKGRFT ISRDNSKNTV YLQMNSLRAE DTATYYCAPN LQCNIQIYWG QGTQVTVSS    119

SEQ ID NO: 87                 moltype = AA   length = 119
FEATURE                       Location/Qualifiers
REGION                        1..119
                              note = Synthetic
source                        1..119
                              mol_type = protein
                              organism = synthetic construct
SEQUENCE: 87
EVQLQASGGG FVQPGGSLRL SCAASGQTFS QFTMGWFRQA PGKEREFVSA ISASSGKSTD    60
YADSVKGRFT ISRDNSKNTV YLQMNSLRAE DTATYYCAGK THNSAKFYWG QGTQVTVSS    119

SEQ ID NO: 88                 moltype = AA   length = 122
FEATURE                       Location/Qualifiers
REGION                        1..122
                              note = Synthetic
source                        1..122
                              mol_type = protein
                              organism = synthetic construct
SEQUENCE: 88
EVQLQASGGG FVQPGGSLRL SCAASGGADG EYSMGWFRQA PGKEREFVSA ISSATGSFTY    60
YADSVKGRFT ISRDNSKNTV YLQMNSLRAE DTATYYCAFP LHDQGGGKKL YWGQGTQVTV   120
SS                                                                 122

SEQ ID NO: 89                 moltype = AA   length = 119
FEATURE                       Location/Qualifiers
REGION                        1..119
                              note = Synthetic
source                        1..119
                              mol_type = protein
                              organism = synthetic construct
SEQUENCE: 89
EVQLQASGGG FVQPGGSLRL SCAASGRISS DYDMGWFRQA PGKEREFVSA ISRRTSQWTY    60
YADSVKGRFT ISRDNSKNTV YLQMNSLRAE DTATYYCAWF GSLLGLFYWG QGTQVTVSS    119

SEQ ID NO: 90                 moltype = AA   length = 122
FEATURE                       Location/Qualifiers
REGION                        1..122
                              note = Synthetic
```

```
                        source          1..122
                                        mol_type = protein
                                        organism = synthetic construct
SEQUENCE: 90
EVQLQASGGG FVQPGGSLRL SCAASGGTFR EYQMGWFRQA PGKEREFVSA ISAGQGHATY    60
YADSVKGRFT ISRDNSKNTV YLQMNSLRAE DTATYYCASY RWDTSSTQPE YWGQGTQVTV   120
SS                                                                 122

SEQ ID NO: 91           moltype = AA  length = 119
FEATURE                 Location/Qualifiers
REGION                  1..119
                        note = Synthetic
source                  1..119
                        mol_type = protein
                        organism = synthetic construct
SEQUENCE: 91
EVQLQASGGG FVQPGGSLRL SCAASGQFFS ISTMGWFRQA PGKEREFVSA ISSWRDKTTH    60
YADSVKGRFT ISRDNSKNTV YLQMNSLRAE DTATYYCAVK ATTGRSFYWG QGTQVTVSS   119

SEQ ID NO: 92           moltype = AA  length = 119
FEATURE                 Location/Qualifiers
REGION                  1..119
                        note = Synthetic
source                  1..119
                        mol_type = protein
                        organism = synthetic construct
SEQUENCE: 92
EVQLQASGGG FVQPGGSLRL SCAASGRIFS HYRMGWFRQA PGKEREFVSA ISHQSQHTQY    60
YADSVKGRFT ISRDNSKNTV YLQMNSLRAE DTATYYCAVR TDNGEYYYWG QGTQVTVSS   119

SEQ ID NO: 93           moltype = AA  length = 122
FEATURE                 Location/Qualifiers
REGION                  1..122
                        note = Synthetic
source                  1..122
                        mol_type = protein
                        organism = synthetic construct
SEQUENCE: 93
EVQLQASGGG FVQPGGSLRL SCAASGGTYQ IYSMGWFRQA PGKEREFVSA ISSWTGFSTY    60
YADSVKGRFT ISRDNSKNTV YLQMNSLRAE DTATYYCADF GRAYNGQVNV YWGQGTQVTV   120
SS                                                                 122

SEQ ID NO: 94           moltype = AA  length = 125
FEATURE                 Location/Qualifiers
REGION                  1..125
                        note = Synthetic
source                  1..125
                        mol_type = protein
                        organism = synthetic construct
SEQUENCE: 94
EVQLQASGGG FVQPGGSLRL SCAASGQTST FQPMGWFRQA PGKEREFVSA ISSRYGQSYY    60
YADSVKGRFT ISRDNSKNTV YLQMNSLRAE DTATYYCAVL HNTNQSEDID YTQYWGQGTQ   120
VTVSS                                                              125

SEQ ID NO: 95           moltype = AA  length = 119
FEATURE                 Location/Qualifiers
REGION                  1..119
                        note = Synthetic
source                  1..119
                        mol_type = protein
                        organism = synthetic construct
SEQUENCE: 95
EVQLQASGGG FVQPGGSLRL SCAASGQPFG IYGMGWFRQA PGKEREFVSA ISSRQGFTVQ    60
YADSVKGRFT ISRDNSKNTV YLQMNSLRAE DTATYYCAVL QWQTADVYWG QGTQVTVSS   119

SEQ ID NO: 96           moltype = AA  length = 119
FEATURE                 Location/Qualifiers
REGION                  1..119
                        note = Synthetic
source                  1..119
                        mol_type = protein
                        organism = synthetic construct
SEQUENCE: 96
EVQLQASGGG FVQPGGSLRL SCAASGRSFS DYIMGWFRQA PGKEREFVSA ISSRTAWWAW    60
YADSVKGRFT ISRDNSKNTV YLQMNSLRAE DTATYYCAFE QNIDTWYYWG QGTQVTVSS   119

SEQ ID NO: 97           moltype = AA  length = 119
FEATURE                 Location/Qualifiers
REGION                  1..119
```

```
                        note = Synthetic
source                  1..119
                        mol_type = protein
                        organism = synthetic construct
SEQUENCE: 97
EVQLQASGGG FVQPGGSLRL SCAASGTTFQ RSDMGWFRQA PGKEREFVSA ISQAAQGWTY    60
YADSVKGRFT ISRDNSKNTV YLQMNSLRAE DTATYYCAFV AASGISTYWG QGTQVTVSS    119

SEQ ID NO: 98           moltype = AA  length = 122
FEATURE                 Location/Qualifiers
REGION                  1..122
                        note = Synthetic
source                  1..122
                        mol_type = protein
                        organism = synthetic construct
SEQUENCE: 98
EVQLQASGGG FVQPGGSLRL SCAASGRAFG IYRMGWFRQA PGKEREFVSA ISGSDGGHVL    60
YADSVKGRFT ISRDNSKNTV YLQMNSLRAE DTATYYCAKW NHDKDHESRI YWGQGTQVTV   120
SS                                                                 122

SEQ ID NO: 99           moltype = AA  length = 125
FEATURE                 Location/Qualifiers
REGION                  1..125
                        note = Synthetic
source                  1..125
                        mol_type = protein
                        organism = synthetic construct
SEQUENCE: 99
EVQLQASGGG FVQPGGSLRL SCAASGFSFR YYGMGWFRQA PGKEREFVSA ISHQSGGWTY    60
YADSVKGRFT ISRDNSKNTV YLQMNSLRAE DTATYYCAVL QTTEQKIFED YINYWGQGTQ   120
VTVSS                                                              125

SEQ ID NO: 100          moltype = AA  length = 125
FEATURE                 Location/Qualifiers
REGION                  1..125
                        note = Synthetic
source                  1..125
                        mol_type = protein
                        organism = synthetic construct
SEQUENCE: 100
EVQLQASGGG FVQPGGSLRL SCAASGRADS WQDMGWFRQA PGKEREFVSA ISQRAQHWTY    60
YADSVKGRFT ISRDNSKNTV YLQMNSLRAE DTATYYCARL PAFSGNARSP YDNYWGQGTQ   120
VTVSS                                                              125

SEQ ID NO: 101          moltype =     length =
SEQUENCE: 101
000

SEQ ID NO: 102          moltype =     length =
SEQUENCE: 102
000

SEQ ID NO: 103          moltype =     length =
SEQUENCE: 103
000

SEQ ID NO: 104          moltype =     length =
SEQUENCE: 104
000

SEQ ID NO: 105          moltype =     length =
SEQUENCE: 105
000

SEQ ID NO: 106          moltype =     length =
SEQUENCE: 106
000

SEQ ID NO: 107          moltype =     length =
SEQUENCE: 107
000

SEQ ID NO: 108          moltype =     length =
SEQUENCE: 108
000

SEQ ID NO: 109          moltype =     length =
SEQUENCE: 109
000
```

SEQ ID NO: 110         moltype =      length =
SEQUENCE: 110
000

SEQ ID NO: 111         moltype =      length =
SEQUENCE: 111
000

SEQ ID NO: 112         moltype =      length =
SEQUENCE: 112
000

SEQ ID NO: 113         moltype =      length =
SEQUENCE: 113
000

SEQ ID NO: 114         moltype =      length =
SEQUENCE: 114
000

SEQ ID NO: 115         moltype =      length =
SEQUENCE: 115
000

SEQ ID NO: 116         moltype =      length =
SEQUENCE: 116
000

SEQ ID NO: 117         moltype =      length =
SEQUENCE: 117
000

SEQ ID NO: 118         moltype =      length =
SEQUENCE: 118
000

SEQ ID NO: 119         moltype =      length =
SEQUENCE: 119
000

SEQ ID NO: 120         moltype =      length =
SEQUENCE: 120
000

SEQ ID NO: 121         moltype =      length =
SEQUENCE: 121
000

SEQ ID NO: 122         moltype =      length =
SEQUENCE: 122
000

SEQ ID NO: 123         moltype =      length =
SEQUENCE: 123
000

SEQ ID NO: 124         moltype =      length =
SEQUENCE: 124
000

SEQ ID NO: 125         moltype =      length =
SEQUENCE: 125
000

SEQ ID NO: 126         moltype =      length =
SEQUENCE: 126
000

SEQ ID NO: 127         moltype =      length =
SEQUENCE: 127
000

SEQ ID NO: 128         moltype =      length =
SEQUENCE: 128
000

SEQ ID NO: 129         moltype =      length =
SEQUENCE: 129

000

SEQ ID NO: 130         moltype =    length =
SEQUENCE: 130
000

SEQ ID NO: 131         moltype =    length =
SEQUENCE: 131
000

SEQ ID NO: 132         moltype =    length =
SEQUENCE: 132
000

SEQ ID NO: 133         moltype =    length =
SEQUENCE: 133
000

SEQ ID NO: 134         moltype =    length =
SEQUENCE: 134
000

SEQ ID NO: 135         moltype =    length =
SEQUENCE: 135
000

SEQ ID NO: 136         moltype =    length =
SEQUENCE: 136
000

SEQ ID NO: 137         moltype =    length =
SEQUENCE: 137
000

SEQ ID NO: 138         moltype =    length =
SEQUENCE: 138
000

SEQ ID NO: 139         moltype =    length =
SEQUENCE: 139
000

SEQ ID NO: 140         moltype =    length =
SEQUENCE: 140
000

SEQ ID NO: 141         moltype =    length =
SEQUENCE: 141
000

SEQ ID NO: 142         moltype =    length =
SEQUENCE: 142
000

SEQ ID NO: 143         moltype =    length =
SEQUENCE: 143
000

SEQ ID NO: 144         moltype =    length =
SEQUENCE: 144
000

SEQ ID NO: 145         moltype =    length =
SEQUENCE: 145
000

SEQ ID NO: 146         moltype =    length =
SEQUENCE: 146
000

SEQ ID NO: 147         moltype =    length =
SEQUENCE: 147
000

SEQ ID NO: 148         moltype =    length =
SEQUENCE: 148
000

SEQ ID NO: 149         moltype =    length =

SEQUENCE: 149
000

SEQ ID NO: 150          moltype =     length =
SEQUENCE: 150
000

SEQ ID NO: 151          moltype =     length =
SEQUENCE: 151
000

SEQ ID NO: 152          moltype =     length =
SEQUENCE: 152
000

SEQ ID NO: 153          moltype =     length =
SEQUENCE: 153
000

SEQ ID NO: 154          moltype =     length =
SEQUENCE: 154
000

SEQ ID NO: 155          moltype =     length =
SEQUENCE: 155
000

SEQ ID NO: 156          moltype =     length =
SEQUENCE: 156
000

SEQ ID NO: 157          moltype =     length =
SEQUENCE: 157
000

SEQ ID NO: 158          moltype =     length =
SEQUENCE: 158
000

SEQ ID NO: 159          moltype =     length =
SEQUENCE: 159
000

SEQ ID NO: 160          moltype =     length =
SEQUENCE: 160
000

SEQ ID NO: 161          moltype =     length =
SEQUENCE: 161
000

SEQ ID NO: 162          moltype =     length =
SEQUENCE: 162
000

SEQ ID NO: 163          moltype =     length =
SEQUENCE: 163
000

SEQ ID NO: 164          moltype =     length =
SEQUENCE: 164
000

SEQ ID NO: 165          moltype =     length =
SEQUENCE: 165
000

SEQ ID NO: 166          moltype =     length =
SEQUENCE: 166
000

SEQ ID NO: 167          moltype =     length =
SEQUENCE: 167
000

SEQ ID NO: 168          moltype =     length =
SEQUENCE: 168
000

```
SEQ ID NO: 169          moltype =    length =
SEQUENCE: 169
000

SEQ ID NO: 170          moltype =    length =
SEQUENCE: 170
000

SEQ ID NO: 171          moltype =    length =
SEQUENCE: 171
000

SEQ ID NO: 172          moltype =    length =
SEQUENCE: 172
000

SEQ ID NO: 173          moltype =    length =
SEQUENCE: 173
000

SEQ ID NO: 174          moltype =    length =
SEQUENCE: 174
000

SEQ ID NO: 175          moltype =    length =
SEQUENCE: 175
000

SEQ ID NO: 176          moltype =    length =
SEQUENCE: 176
000

SEQ ID NO: 177          moltype =    length =
SEQUENCE: 177
000

SEQ ID NO: 178          moltype =    length =
SEQUENCE: 178
000

SEQ ID NO: 179          moltype =    length =
SEQUENCE: 179
000

SEQ ID NO: 180          moltype =    length =
SEQUENCE: 180
000

SEQ ID NO: 181          moltype =    length =
SEQUENCE: 181
000

SEQ ID NO: 182          moltype =    length =
SEQUENCE: 182
000

SEQ ID NO: 183          moltype = AA  length = 95
FEATURE                 Location/Qualifiers
REGION                  1..95
                        note = Synthetic construct
SITE                    26..27
                        note = CDR1 insertion site
SITE                    45..46
                        note = CDR2 insertion site
SITE                    83..84
                        note = CDR3 insertion site
source                  1..95
                        mol_type = protein
                        organism = synthetic construct
SEQUENCE: 183
EVQLQASGGG FVQPGGSLRL SCAASGMGWF RQAPGKEREF VSAISYADSV KGRFTISRDN   60
SKNTVYLQMN SLRAEDTATY YCAYWGQGTQ VTVSS                              95

SEQ ID NO: 184          moltype = AA  length = 95
FEATURE                 Location/Qualifiers
REGION                  1..95
                        note = Synthetic construct
SITE                    26..27
                        note = CDR1 insertion site
```

```
SITE                    45..46
                        note = CDR2 insertion site
SITE                    83..84
                        note = CDR3 insertion site
source                  1..95
                        mol_type = protein
                        organism = synthetic construct
SEQUENCE: 184
EVQLQASGGG FVQPGGSLRL SCAASGMGWF RQAPGKEREF VSAISYADSV KGRFTISRDN    60
SKNTVYLQMN SLRAEDTATY YCAYWGQGTQ VTVSS                               95

SEQ ID NO: 185          moltype = AA  length = 96
FEATURE                 Location/Qualifiers
REGION                  1..96
                        note = Synthetic construct
SITE                    26..27
                        note = CDR1 insertion site
SITE                    45..46
                        note = CDR2 insertion site
SITE                    83..84
                        note = CDR3 insertion site
source                  1..96
                        mol_type = protein
                        organism = synthetic construct
SEQUENCE: 185
EVQLQASGGG FVQAGGSLRL SCAASGMGWF RQAPGKEREF VAAISYYADS VKGRFTISRD    60
NAKNTVYLQM NSLKPEDTAT YYCAYWGQGT QVTVSS                              96

SEQ ID NO: 186          moltype = AA  length = 96
FEATURE                 Location/Qualifiers
REGION                  1..96
                        note = Synthetic construct
SITE                    26..27
                        note = CDR1 insertion site
SITE                    45..46
                        note = CDR2 insertion site
SITE                    83..84
                        note = CDR3 insertion site
source                  1..96
                        mol_type = protein
                        organism = synthetic construct
SEQUENCE: 186
EVQLQASGGG FVQAGGSLRL SCAASGMGWF RQAPGKEREF VAAISYYADS VKGRFTISRD    60
NAKNTVYLQM NSLKPEDTAT YYCAYWGQGT QVTVSS                              96

SEQ ID NO: 187          moltype =    length =
SEQUENCE: 187
000

SEQ ID NO: 188          moltype =    length =
SEQUENCE: 188
000

SEQ ID NO: 189          moltype =    length =
SEQUENCE: 189
000

SEQ ID NO: 190          moltype = AA  length = 26
FEATURE                 Location/Qualifiers
REGION                  1..26
                        note = Synthetic construct
source                  1..26
                        mol_type = protein
                        organism = synthetic construct
SEQUENCE: 190
EVQLQASGGG FVQAGGSLRL SCAASG                                         26

SEQ ID NO: 191          moltype = AA  length = 26
FEATURE                 Location/Qualifiers
REGION                  1..26
                        note = Synthetic construct
source                  1..26
                        mol_type = protein
                        organism = synthetic construct
SEQUENCE: 191
EVQLQASGGG FVQPGGSLRL SCAASG                                         26

SEQ ID NO: 192          moltype = AA  length = 30
FEATURE                 Location/Qualifiers
```

```
REGION                    1..30
                          note = Synthetic construct
source                    1..30
                          mol_type = protein
                          organism = synthetic construct
SEQUENCE: 192
QVQLVESGGG SVQAGGSLRL SCTASGGSEY                                            30

SEQ ID NO: 193            moltype = AA  length = 26
FEATURE                   Location/Qualifiers
REGION                    1..26
                          note = Synthetic construct
source                    1..26
                          mol_type = protein
                          organism = synthetic construct
SEQUENCE: 193
QVQLVESGGG SVQAGGSLRL SCTASG                                                26

SEQ ID NO: 194            moltype = AA  length = 30
FEATURE                   Location/Qualifiers
REGION                    1..30
                          note = Synthetic construct
source                    1..30
                          mol_type = protein
                          organism = synthetic construct
SEQUENCE: 194
QVQLVESGGG SVQAGGSLRL SCTASGFSRE                                            30

SEQ ID NO: 195            moltype = AA  length = 30
FEATURE                   Location/Qualifiers
REGION                    1..30
                          note = Synthetic construct
source                    1..30
                          mol_type = protein
                          organism = synthetic construct
SEQUENCE: 195
QVQLQESGPS LVRPSQTLSL TCTISGFSRE                                            30

SEQ ID NO: 196            moltype = AA  length = 26
FEATURE                   Location/Qualifiers
REGION                    1..26
                          note = Synthetic construct
source                    1..26
                          mol_type = protein
                          organism = synthetic construct
SEQUENCE: 196
QVQLQESGPS LVRPSQTLSL TCTISG                                                26

SEQ ID NO: 197            moltype = AA  length = 30
FEATURE                   Location/Qualifiers
REGION                    1..30
                          note = Synthetic construct
source                    1..30
                          mol_type = protein
                          organism = synthetic construct
SEQUENCE: 197
QVQLVESGGN LVQPGGSLRL SCAASGFTFG                                            30

SEQ ID NO: 198            moltype = AA  length = 26
FEATURE                   Location/Qualifiers
REGION                    1..26
                          note = Synthetic construct
source                    1..26
                          mol_type = protein
                          organism = synthetic construct
SEQUENCE: 198
QVQLVESGGN LVQPGGSLRL SCAASG                                                26

SEQ ID NO: 199            moltype = AA  length = 30
FEATURE                   Location/Qualifiers
REGION                    1..30
                          note = Synthetic construct
source                    1..30
                          mol_type = protein
                          organism = synthetic construct
SEQUENCE: 199
QVQLVESGGA LVQPGGSLRL SCAASGFPVN                                            30

SEQ ID NO: 200            moltype = AA  length = 30
```

```
FEATURE                 Location/Qualifiers
REGION                  1..30
                        note = Synthetic construct
source                  1..30
                        mol_type = protein
                        organism = synthetic construct
SEQUENCE: 200
QVQLVESGGA LVQPGGSLRL SCAASGFTFG                                    30

SEQ ID NO: 201          moltype = AA  length = 30
FEATURE                 Location/Qualifiers
REGION                  1..30
                        note = Synthetic construct
source                  1..30
                        mol_type = protein
                        organism = synthetic construct
SEQUENCE: 201
QVQLVESGGG LVQPGGSLRL SCAASGFTFG                                    30

SEQ ID NO: 202          moltype = AA  length = 26
FEATURE                 Location/Qualifiers
REGION                  1..26
                        note = Synthetic construct
source                  1..26
                        mol_type = protein
                        organism = synthetic construct
SEQUENCE: 202
QVQLVESGGA LVQPGGSLRL SCAASG                                        26

SEQ ID NO: 203          moltype = AA  length = 26
FEATURE                 Location/Qualifiers
REGION                  1..26
                        note = Synthetic construct
source                  1..26
                        mol_type = protein
                        organism = synthetic construct
SEQUENCE: 203
QVQLVESGGG LVQAGGSLRL SCAASG                                        26

SEQ ID NO: 204          moltype = AA  length = 26
FEATURE                 Location/Qualifiers
REGION                  1..26
                        note = Synthetic construct
source                  1..26
                        mol_type = protein
                        organism = synthetic construct
SEQUENCE: 204
QVQLVESGGG LMQAGGSLRL SCAVSG                                        26

SEQ ID NO: 205          moltype = AA  length = 26
FEATURE                 Location/Qualifiers
REGION                  1..26
                        note = Synthetic construct
source                  1..26
                        mol_type = protein
                        organism = synthetic construct
SEQUENCE: 205
QVQLQESGGG LVQAGGSLRL SCAASG                                        26

SEQ ID NO: 206          moltype = AA  length = 26
FEATURE                 Location/Qualifiers
REGION                  1..26
                        note = Synthetic construct
source                  1..26
                        mol_type = protein
                        organism = synthetic construct
SEQUENCE: 206
HVQLVESGGG LVQAGGSLRL SCAASG                                        26

SEQ ID NO: 207          moltype = AA  length = 26
FEATURE                 Location/Qualifiers
REGION                  1..26
                        note = Synthetic construct
source                  1..26
                        mol_type = protein
                        organism = synthetic construct
SEQUENCE: 207
DVQLVESGGG LVQAGGSLRL SCAASG                                        26
```

```
SEQ ID NO: 208           moltype = AA  length = 26
FEATURE                  Location/Qualifiers
REGION                   1..26
                         note = Synthetic construct
source                   1..26
                         mol_type = protein
                         organism = synthetic construct
SEQUENCE: 208
EVQLVESGGG LVQAGGSLRL SCAASG                                          26

SEQ ID NO: 209           moltype = AA  length = 30
FEATURE                  Location/Qualifiers
REGION                   1..30
                         note = Synthetic construct
source                   1..30
                         mol_type = protein
                         organism = synthetic construct
SEQUENCE: 209
EVQLVESGGG VVQPGRSLRL SCAASGFTFD                                      30

SEQ ID NO: 210           moltype = AA  length = 26
FEATURE                  Location/Qualifiers
REGION                   1..26
                         note = Synthetic construct
source                   1..26
                         mol_type = protein
                         organism = synthetic construct
SEQUENCE: 210
EVQLVESGGG VVQPGRSLRL SCAASG                                          26

SEQ ID NO: 211           moltype = AA  length = 30
FEATURE                  Location/Qualifiers
REGION                   1..30
                         note = Synthetic construct
source                   1..30
                         mol_type = protein
                         organism = synthetic construct
SEQUENCE: 211
DVQLQASGGG LVQAGGSLRL SCAASGFKIT                                      30

SEQ ID NO: 212           moltype = AA  length = 26
FEATURE                  Location/Qualifiers
REGION                   1..26
                         note = Synthetic construct
source                   1..26
                         mol_type = protein
                         organism = synthetic construct
SEQUENCE: 212
DVQLQASGGG LVQAGGSLRL SCAASG                                          26

SEQ ID NO: 213           moltype =     length =
SEQUENCE: 213
000

SEQ ID NO: 214           moltype =     length =
SEQUENCE: 214
000

SEQ ID NO: 215           moltype =     length =
SEQUENCE: 215
000

SEQ ID NO: 216           moltype =     length =
SEQUENCE: 216
000

SEQ ID NO: 217           moltype =     length =
SEQUENCE: 217
000

SEQ ID NO: 218           moltype =     length =
SEQUENCE: 218
000

SEQ ID NO: 219           moltype =     length =
SEQUENCE: 219
000

SEQ ID NO: 220           moltype = AA  length = 19
```

```
FEATURE                 Location/Qualifiers
REGION                  1..19
                        note = Synthetic construct
source                  1..19
                        mol_type = protein
                        organism = synthetic construct
SEQUENCE: 220
MGWFRQAPGK EREFVAAIS                                                    19

SEQ ID NO: 221          moltype = AA  length = 19
FEATURE                 Location/Qualifiers
REGION                  1..19
                        note = Synthetic construct
source                  1..19
                        mol_type = protein
                        organism = synthetic construct
SEQUENCE: 221
MGWFRQAPGK EREFVSAIS                                                    19

SEQ ID NO: 222          moltype = AA  length = 14
FEATURE                 Location/Qualifiers
REGION                  1..14
                        note = Synthetic construct
source                  1..14
                        mol_type = protein
                        organism = synthetic construct
SEQUENCE: 222
WFRQAPGQER EAVA                                                         14

SEQ ID NO: 223          moltype = AA  length = 17
FEATURE                 Location/Qualifiers
REGION                  1..17
                        note = Synthetic construct
source                  1..17
                        mol_type = protein
                        organism = synthetic construct
SEQUENCE: 223
WFRQAPGQER EAVAAIA                                                      17

SEQ ID NO: 224          moltype = AA  length = 14
FEATURE                 Location/Qualifiers
REGION                  1..14
                        note = Synthetic construct
source                  1..14
                        mol_type = protein
                        organism = synthetic construct
SEQUENCE: 224
WVRQAPGKAL EWLG                                                         14

SEQ ID NO: 225          moltype = AA  length = 16
FEATURE                 Location/Qualifiers
REGION                  1..16
                        note = Synthetic construct
source                  1..16
                        mol_type = protein
                        organism = synthetic construct
SEQUENCE: 225
WVRQAPGKAL EWLGRI                                                       16

SEQ ID NO: 226          moltype = AA  length = 14
FEATURE                 Location/Qualifiers
REGION                  1..14
                        note = Synthetic construct
source                  1..14
                        mol_type = protein
                        organism = synthetic construct
SEQUENCE: 226
WFRQAPGQER EWLG                                                         14

SEQ ID NO: 227          moltype = AA  length = 16
FEATURE                 Location/Qualifiers
REGION                  1..16
                        note = Synthetic construct
source                  1..16
                        mol_type = protein
                        organism = synthetic construct
SEQUENCE: 227
WFRQAPGQER EWLGRI                                                       16
```

```
SEQ ID NO: 228          moltype = AA   length = 14
FEATURE                 Location/Qualifiers
REGION                  1..14
                        note = Synthetic construct
source                  1..14
                        mol_type = protein
                        organism = synthetic construct
SEQUENCE: 228
WVRQAPGGGL EWVA                                                            14

SEQ ID NO: 229          moltype = AA   length = 14
FEATURE                 Location/Qualifiers
REGION                  1..14
                        note = Synthetic construct
source                  1..14
                        mol_type = protein
                        organism = synthetic construct
SEQUENCE: 229
WYRQATGKER EWVA                                                            14

SEQ ID NO: 230          moltype = AA   length = 16
FEATURE                 Location/Qualifiers
REGION                  1..16
                        note = Synthetic construct
source                  1..16
                        mol_type = protein
                        organism = synthetic construct
SEQUENCE: 230
MSWYRQATGK EREWVA                                                          16

SEQ ID NO: 231          moltype = AA   length = 19
FEATURE                 Location/Qualifiers
REGION                  1..19
                        note = Synthetic construct
source                  1..19
                        mol_type = protein
                        organism = synthetic construct
SEQUENCE: 231
MGWFRQAPGK EREFVAAIR                                                       19

SEQ ID NO: 232          moltype = AA   length = 18
FEATURE                 Location/Qualifiers
REGION                  1..18
                        note = Synthetic construct
source                  1..18
                        mol_type = protein
                        organism = synthetic construct
SEQUENCE: 232
MGWFRQAPGK EREFVAAI                                                        18

SEQ ID NO: 233          moltype = AA   length = 16
FEATURE                 Location/Qualifiers
REGION                  1..16
                        note = Synthetic construct
source                  1..16
                        mol_type = protein
                        organism = synthetic construct
SEQUENCE: 233
MGWFRQAPGK EREFVA                                                          16

SEQ ID NO: 234          moltype = AA   length = 16
FEATURE                 Location/Qualifiers
REGION                  1..16
                        note = Synthetic construct
source                  1..16
                        mol_type = protein
                        organism = synthetic construct
SEQUENCE: 234
MGWYRQAPGK ERELVA                                                          16

SEQ ID NO: 235          moltype = AA   length = 17
FEATURE                 Location/Qualifiers
REGION                  1..17
                        note = Synthetic construct
source                  1..17
                        mol_type = protein
                        organism = synthetic construct
SEQUENCE: 235
MGWYRQAPGK ERELVAA                                                         17
```

```
SEQ ID NO: 236            moltype = AA   length = 19
FEATURE                   Location/Qualifiers
REGION                    1..19
                          note = Synthetic construct
source                    1..19
                          mol_type = protein
                          organism = synthetic construct
SEQUENCE: 236
MGWYRQAPGK ERELVAAID                                                    19

SEQ ID NO: 237            moltype = AA   length = 19
FEATURE                   Location/Qualifiers
REGION                    1..19
                          note = Synthetic construct
source                    1..19
                          mol_type = protein
                          organism = synthetic construct
SEQUENCE: 237
MGWYRQAPGK ERELVAVIS                                                    19

SEQ ID NO: 238            moltype = AA   length = 16
FEATURE                   Location/Qualifiers
REGION                    1..16
                          note = Synthetic construct
source                    1..16
                          mol_type = protein
                          organism = synthetic construct
SEQUENCE: 238
MGWFRQAPGK EREGVA                                                       16

SEQ ID NO: 239            moltype = AA   length = 14
FEATURE                   Location/Qualifiers
REGION                    1..14
                          note = Synthetic construct
source                    1..14
                          mol_type = protein
                          organism = synthetic construct
SEQUENCE: 239
WFRQAPGKER EGVA                                                         14

SEQ ID NO: 240            moltype = AA   length = 16
FEATURE                   Location/Qualifiers
REGION                    1..16
                          note = Synthetic construct
source                    1..16
                          mol_type = protein
                          organism = synthetic construct
SEQUENCE: 240
MGWFRQAPGK EREFVA                                                       16

SEQ ID NO: 241            moltype = AA   length = 14
FEATURE                   Location/Qualifiers
REGION                    1..14
                          note = Synthetic construct
source                    1..14
                          mol_type = protein
                          organism = synthetic construct
SEQUENCE: 241
WFRQAPGKER EFVA                                                         14

SEQ ID NO: 242            moltype = AA   length = 14
FEATURE                   Location/Qualifiers
REGION                    1..14
                          note = Synthetic construct
source                    1..14
                          mol_type = protein
                          organism = synthetic construct
SEQUENCE: 242
WVRQAPGKGP EWVA                                                         14

SEQ ID NO: 243            moltype = AA   length = 14
FEATURE                   Location/Qualifiers
REGION                    1..14
                          note = Synthetic construct
source                    1..14
                          mol_type = protein
                          organism = synthetic construct
SEQUENCE: 243
```

```
WFRQAPGKER EFVS                                                             14

SEQ ID NO: 244          moltype =   length =
SEQUENCE: 244
000

SEQ ID NO: 245          moltype =   length =
SEQUENCE: 245
000

SEQ ID NO: 246          moltype =   length =
SEQUENCE: 246
000

SEQ ID NO: 247          moltype =   length =
SEQUENCE: 247
000

SEQ ID NO: 248          moltype =   length =
SEQUENCE: 248
000

SEQ ID NO: 249          moltype =   length =
SEQUENCE: 249
000

SEQ ID NO: 250          moltype = AA   length = 38
FEATURE                 Location/Qualifiers
REGION                  1..38
                        note = Synthetic construct
source                  1..38
                        mol_type = protein
                        organism = synthetic construct
SEQUENCE: 250
YADSVKGRFT ISRDNAKNTV YLQMNSLKPE DTATYYCA                                    38

SEQ ID NO: 251          moltype = AA   length = 39
FEATURE                 Location/Qualifiers
REGION                  1..39
                        note = Synthetic construct
source                  1..39
                        mol_type = protein
                        organism = synthetic construct
SEQUENCE: 251
YYADSVKGRF TISRDNAKNT VYLQMNSLKP EDTATYYCA                                   39

SEQ ID NO: 252          moltype = AA   length = 38
FEATURE                 Location/Qualifiers
REGION                  1..38
                        note = Synthetic construct
source                  1..38
                        mol_type = protein
                        organism = synthetic construct
SEQUENCE: 252
YADSVKGRFT ISRDNSKNTV YLQMNSLRAE DTATYYCA                                    38

SEQ ID NO: 253          moltype = AA   length = 39
FEATURE                 Location/Qualifiers
REGION                  1..39
                        note = Synthetic construct
source                  1..39
                        mol_type = protein
                        organism = synthetic construct
SEQUENCE: 253
YYADSVKGRF TISRDNSKNT VYLQMNSLRA EDTATYYCA                                   39

SEQ ID NO: 254          moltype = AA   length = 31
FEATURE                 Location/Qualifiers
REGION                  1..31
                        note = Synthetic construct
source                  1..31
                        mol_type = protein
                        organism = synthetic construct
SEQUENCE: 254
RFTISRDNAK NTVTLQMNNL KPEDTAIYYC A                                           31

SEQ ID NO: 255          moltype = AA   length = 32
FEATURE                 Location/Qualifiers
REGION                  1..32
```

```
                         note = Synthetic construct
source                   1..32
                         mol_type = protein
                         organism = synthetic construct
SEQUENCE: 255
RFTISRDNAK NTVTLQMNNL KPEDTAIYYC AA                              32

SEQ ID NO: 256           moltype = AA   length = 31
FEATURE                  Location/Qualifiers
REGION                   1..31
                         note = Synthetic construct
source                   1..31
                         mol_type = protein
                         organism = synthetic construct
SEQUENCE: 256
RLTITRDISK SQVSLSLSSV TLEDTAEYYC V                               31

SEQ ID NO: 257           moltype = AA   length = 32
FEATURE                  Location/Qualifiers
REGION                   1..32
                         note = Synthetic construct
source                   1..32
                         mol_type = protein
                         organism = synthetic construct
SEQUENCE: 257
RLTITRDISK SQVSLSLSSV TLEDTAEYYC VY                              32

SEQ ID NO: 258           moltype = AA   length = 31
FEATURE                  Location/Qualifiers
REGION                   1..31
                         note = Synthetic construct
source                   1..31
                         mol_type = protein
                         organism = synthetic construct
SEQUENCE: 258
RFTISRDIAK NTVTLQMNNL KPEDTAIYYV Y                               31

SEQ ID NO: 259           moltype = AA   length = 32
FEATURE                  Location/Qualifiers
REGION                   1..32
                         note = Synthetic construct
source                   1..32
                         mol_type = protein
                         organism = synthetic construct
SEQUENCE: 259
RFTISRDIAK NTVTLQMNNL KPEDTAIYYV YA                              32

SEQ ID NO: 260           moltype = AA   length = 39
FEATURE                  Location/Qualifiers
REGION                   1..39
                         note = Synthetic construct
source                   1..39
                         mol_type = protein
                         organism = synthetic construct
SEQUENCE: 260
YYADSVKGRF TISRDNAKNT VTLQMNNLKP EDTAIYYCA                       39

SEQ ID NO: 261           moltype = AA   length = 40
FEATURE                  Location/Qualifiers
REGION                   1..40
                         note = Synthetic construct
source                   1..40
                         mol_type = protein
                         organism = synthetic construct
SEQUENCE: 261
YYADSVKGRF TISRDNAKNT VTLQMNNLKP EDTAIYYCAA                      40

SEQ ID NO: 262           moltype = AA   length = 39
FEATURE                  Location/Qualifiers
REGION                   1..39
                         note = Synthetic construct
source                   1..39
                         mol_type = protein
                         organism = synthetic construct
SEQUENCE: 262
YEDSVKGRFC ISRDDARNTV YLQMNSLKPE DTAVYYCNV                       39

SEQ ID NO: 263           moltype = AA   length = 38
FEATURE                  Location/Qualifiers
```

```
                               -continued

REGION                  1..38
                        note = Synthetic construct
source                  1..38
                        mol_type = protein
                        organism = synthetic construct
SEQUENCE: 263
YEDSVKGRFC ISRDDARNTV YLQMNSLKPE DTAVYYCN                            38

SEQ ID NO: 264          moltype = AA   length = 39
FEATURE                 Location/Qualifiers
REGION                  1..39
                        note = Synthetic construct
source                  1..39
                        mol_type = protein
                        organism = synthetic construct
SEQUENCE: 264
YADSVKGRFT ISRDNAKNSV YLQMNSLRVE DTAVYYCAR                           39

SEQ ID NO: 265          moltype = AA   length = 38
FEATURE                 Location/Qualifiers
REGION                  1..38
                        note = Synthetic construct
source                  1..38
                        mol_type = protein
                        organism = synthetic construct
SEQUENCE: 265
YADSVKGRFT ISRDNAKNSV YLQMNSLRVE DTAVYYCA                            38

SEQ ID NO: 266          moltype = AA   length = 39
FEATURE                 Location/Qualifiers
REGION                  1..39
                        note = Synthetic construct
source                  1..39
                        mol_type = protein
                        organism = synthetic construct
SEQUENCE: 266
YADSVKGRFT ISRDNARNTV YLQMNSLKPE DTAVYYCAR                           39

SEQ ID NO: 267          moltype = AA   length = 38
FEATURE                 Location/Qualifiers
REGION                  1..38
                        note = Synthetic construct
source                  1..38
                        mol_type = protein
                        organism = synthetic construct
SEQUENCE: 267
YADSVKGRFT ISRDNARNTV YLQMNSLKPE DTAVYYCA                            38

SEQ ID NO: 268          moltype = AA   length = 39
FEATURE                 Location/Qualifiers
REGION                  1..39
                        note = Synthetic construct
source                  1..39
                        mol_type = protein
                        organism = synthetic construct
SEQUENCE: 268
YADSVKGRFT ISRDNARNTV YLQMNSLKPE DTAVYYCAR                           39

SEQ ID NO: 269          moltype = AA   length = 32
FEATURE                 Location/Qualifiers
REGION                  1..32
                        note = Synthetic construct
source                  1..32
                        mol_type = protein
                        organism = synthetic construct
SEQUENCE: 269
RFTISRDNAR NTVYLQMNSL KPEDTAVYYC AR                                  32

SEQ ID NO: 270          moltype = AA   length = 39
FEATURE                 Location/Qualifiers
REGION                  1..39
                        note = Synthetic construct
source                  1..39
                        mol_type = protein
                        organism = synthetic construct
SEQUENCE: 270
YADSVKGRFT ISRDKGKNTV YLQMDSLKPE DTATYYCAA                           39

SEQ ID NO: 271          moltype = AA   length = 32
```

```
FEATURE                 Location/Qualifiers
REGION                  1..32
                        note = Synthetic construct
source                  1..32
                        mol_type = protein
                        organism = synthetic construct
SEQUENCE: 271
RFTISRDKGK NTVYLQMDSL KPEDTATYYC AA                                    32

SEQ ID NO: 272          moltype = AA   length = 38
FEATURE                 Location/Qualifiers
REGION                  1..38
                        note = Synthetic construct
source                  1..38
                        mol_type = protein
                        organism = synthetic construct
SEQUENCE: 272
YADSVKGRFT ISRDKGKNTV YLQMDSLKPE DTATYYCA                              38

SEQ ID NO: 273          moltype = AA   length = 31
FEATURE                 Location/Qualifiers
REGION                  1..31
                        note = Synthetic construct
source                  1..31
                        mol_type = protein
                        organism = synthetic construct
SEQUENCE: 273
RFTISRDKGK NTVYLQMDSL KPEDTATYYC A                                     31

SEQ ID NO: 274          moltype = AA   length = 39
FEATURE                 Location/Qualifiers
REGION                  1..39
                        note = Synthetic construct
source                  1..39
                        mol_type = protein
                        organism = synthetic construct
SEQUENCE: 274
YYADSVKGRF TISRDKAKNT VYLQMNSLKY EDTAVYYCA                             39

SEQ ID NO: 275          moltype = AA   length = 38
FEATURE                 Location/Qualifiers
REGION                  1..38
                        note = Synthetic construct
source                  1..38
                        mol_type = protein
                        organism = synthetic construct
SEQUENCE: 275
YADSVKGRFT ISRDKAKNTV YLQMNSLKYE DTAVYYCA                              38

SEQ ID NO: 276          moltype = AA   length = 39
FEATURE                 Location/Qualifiers
REGION                  1..39
                        note = Synthetic construct
source                  1..39
                        mol_type = protein
                        organism = synthetic construct
SEQUENCE: 276
YYADSVKGRF TISRDNAKNT VYLQMNSLKP EDTAVYYCA                             39

SEQ ID NO: 277          moltype = AA   length = 39
FEATURE                 Location/Qualifiers
REGION                  1..39
                        note = Synthetic construct
source                  1..39
                        mol_type = protein
                        organism = synthetic construct
SEQUENCE: 277
LHNPALKSRL TITRDISKSQ VSLSLSSVTL EDTAEYYCV                             39

SEQ ID NO: 278          moltype = AA   length = 40
FEATURE                 Location/Qualifiers
REGION                  1..40
                        note = Synthetic construct
source                  1..40
                        mol_type = protein
                        organism = synthetic construct
SEQUENCE: 278
LHNPALKSRL TITRDISKSQ VSLSLSSVTL EDTAEYYCVY                            40
```

```
SEQ ID NO: 279          moltype = AA   length = 40
FEATURE                 Location/Qualifiers
REGION                  1..40
                        note = Synthetic construct
source                  1..40
                        mol_type = protein
                        organism = synthetic construct
SEQUENCE: 279
LHNPALKSRF TISRDIAKNT VTLQMNNLKP EDTAIYYVYA                              40

SEQ ID NO: 280          moltype = AA   length = 39
FEATURE                 Location/Qualifiers
REGION                  1..39
                        note = Synthetic construct
source                  1..39
                        mol_type = protein
                        organism = synthetic construct
SEQUENCE: 280
YADSVKGRFT ISRDNAKNTV YLQMNSLKPE DTAVYYCAA                               39

SEQ ID NO: 281          moltype = AA   length = 38
FEATURE                 Location/Qualifiers
REGION                  1..38
                        note = Synthetic construct
source                  1..38
                        mol_type = protein
                        organism = synthetic construct
SEQUENCE: 281
YADSVKGRFT ISRDNAKNTV YLQMNSLKPE DTAVYYCA                                38

SEQ ID NO: 282          moltype = AA   length = 40
FEATURE                 Location/Qualifiers
REGION                  1..40
                        note = Synthetic construct
source                  1..40
                        mol_type = protein
                        organism = synthetic construct
SEQUENCE: 282
YYADSVKGRF TISRDNAKNT VYLQMNSLKP EDTAVYYCAA                              40

SEQ ID NO: 283          moltype = AA   length = 32
FEATURE                 Location/Qualifiers
REGION                  1..32
                        note = Synthetic construct
source                  1..32
                        mol_type = protein
                        organism = synthetic construct
SEQUENCE: 283
RFTISRDNSK NTLYLQMNSL RAEDTAVYYC AK                                      32

SEQ ID NO: 284          moltype = AA   length = 32
FEATURE                 Location/Qualifiers
REGION                  1..32
                        note = Synthetic construct
source                  1..32
                        mol_type = protein
                        organism = synthetic construct
SEQUENCE: 284
RFTISRDNAK NTVYLQMNSL KPEDTADYYC AA                                      32

SEQ ID NO: 285          moltype =    length =
SEQUENCE: 285
000

SEQ ID NO: 286          moltype =    length =
SEQUENCE: 286
000

SEQ ID NO: 287          moltype =    length =
SEQUENCE: 287
000

SEQ ID NO: 288          moltype =    length =
SEQUENCE: 288
000

SEQ ID NO: 289          moltype =    length =
SEQUENCE: 289
000
```

```
SEQ ID NO: 290         moltype = AA   length = 12
FEATURE                Location/Qualifiers
REGION                 1..12
                       note = Synthetic construct
source                 1..12
                       mol_type = protein
                       organism = synthetic construct
SEQUENCE: 290
YWGQGTQVTV SS                                                            12

SEQ ID NO: 291         moltype = AA   length = 11
FEATURE                Location/Qualifiers
REGION                 1..11
                       note = Synthetic construct
source                 1..11
                       mol_type = protein
                       organism = synthetic construct
SEQUENCE: 291
WGQGTQVTVS S                                                             11

SEQ ID NO: 292         moltype = AA   length = 12
FEATURE                Location/Qualifiers
REGION                 1..12
                       note = Synthetic construct
source                 1..12
                       mol_type = protein
                       organism = synthetic construct
SEQUENCE: 292
VWGPGLLLTV SS                                                            12

SEQ ID NO: 293         moltype = AA   length = 11
FEATURE                Location/Qualifiers
REGION                 1..11
                       note = Synthetic construct
source                 1..11
                       mol_type = protein
                       organism = synthetic construct
SEQUENCE: 293
WGPGLLLTVS S                                                             11

SEQ ID NO: 294         moltype = AA   length = 10
FEATURE                Location/Qualifiers
REGION                 1..10
                       note = Synthetic construct
source                 1..10
                       mol_type = protein
                       organism = synthetic construct
SEQUENCE: 294
WGQGTLVTVS                                                               10

SEQ ID NO: 295         moltype = AA   length = 11
FEATURE                Location/Qualifiers
REGION                 1..11
                       note = Synthetic construct
source                 1..11
                       mol_type = protein
                       organism = synthetic construct
SEQUENCE: 295
WGQGTLVTVS S                                                             11

SEQ ID NO: 296         moltype = AA   length = 10
FEATURE                Location/Qualifiers
REGION                 1..10
                       note = Synthetic construct
source                 1..10
                       mol_type = protein
                       organism = synthetic construct
SEQUENCE: 296
WGQGTQVTVS                                                               10

SEQ ID NO: 297         moltype = AA   length = 11
FEATURE                Location/Qualifiers
REGION                 1..11
                       note = Synthetic construct
source                 1..11
                       mol_type = protein
                       organism = synthetic construct
SEQUENCE: 297
```

```
WGQGTQVTVS S                                                                                  11

SEQ ID NO: 298         moltype = AA  length = 12
FEATURE                Location/Qualifiers
REGION                 1..12
                       note = Synthetic construct
source                 1..12
                       mol_type = protein
                       organism = synthetic construct
SEQUENCE: 298
QWGQGTQVTV SS                                                                                 12

SEQ ID NO: 299         moltype = AA  length = 11
FEATURE                Location/Qualifiers
REGION                 1..11
                       note = Synthetic construct
source                 1..11
                       mol_type = protein
                       organism = synthetic construct
SEQUENCE: 299
YWGQGTQVTV S                                                                                  11

SEQ ID NO: 300         moltype = AA  length = 11
FEATURE                Location/Qualifiers
REGION                 1..11
                       note = Synthetic construct
source                 1..11
                       mol_type = protein
                       organism = synthetic construct
SEQUENCE: 300
WGQGTTVVVS S                                                                                  11

SEQ ID NO: 301         moltype = AA  length = 11
FEATURE                Location/Qualifiers
REGION                 1..11
                       note = Synthetic construct
source                 1..11
                       mol_type = protein
                       organism = synthetic construct
SEQUENCE: 301
WGKGTQVTVS S                                                                                  11

SEQ ID NO: 302         moltype =     length =
SEQUENCE: 302
000

SEQ ID NO: 303         moltype =     length =
SEQUENCE: 303
000

SEQ ID NO: 304         moltype =     length =
SEQUENCE: 304
000

SEQ ID NO: 305         moltype =     length =
SEQUENCE: 305
000

SEQ ID NO: 306         moltype =     length =
SEQUENCE: 306
000

SEQ ID NO: 307         moltype =     length =
SEQUENCE: 307
000

SEQ ID NO: 308         moltype =     length =
SEQUENCE: 308
000

SEQ ID NO: 309         moltype =     length =
SEQUENCE: 309
000

SEQ ID NO: 310         moltype =     length =
SEQUENCE: 310
000

SEQ ID NO: 311         moltype = AA  length = 4
```

```
FEATURE              Location/Qualifiers
REGION               1..4
                     note = Synthetic construct
source               1..4
                     mol_type = protein
                     organism = synthetic construct
SEQUENCE: 311
GGGS                                                                    4

SEQ ID NO: 312       moltype = AA  length = 4
FEATURE              Location/Qualifiers
REGION               1..4
                     note = Synthetic construct
source               1..4
                     mol_type = protein
                     organism = synthetic construct
SEQUENCE: 312
GGGG                                                                    4

SEQ ID NO: 313       moltype = AA  length = 5
FEATURE              Location/Qualifiers
REGION               1..5
                     note = Synthetic construct
source               1..5
                     mol_type = protein
                     organism = synthetic construct
SEQUENCE: 313
GGGGS                                                                   5

SEQ ID NO: 314       moltype = AA  length = 4
FEATURE              Location/Qualifiers
REGION               1..4
                     note = Synthetic construct
source               1..4
                     mol_type = protein
                     organism = synthetic construct
SEQUENCE: 314
GGSG                                                                    4

SEQ ID NO: 315       moltype = AA  length = 10
FEATURE              Location/Qualifiers
REGION               1..10
                     note = Synthetic construct
source               1..10
                     mol_type = protein
                     organism = synthetic construct
SEQUENCE: 315
GGGGSGGGGS                                                             10

SEQ ID NO: 316       moltype = AA  length = 15
FEATURE              Location/Qualifiers
REGION               1..15
                     note = Synthetic construct
source               1..15
                     mol_type = protein
                     organism = synthetic construct
SEQUENCE: 316
GGGGSGGGGS GGGGS                                                       15

SEQ ID NO: 317       moltype = AA  length = 20
FEATURE              Location/Qualifiers
REGION               1..20
                     note = Synthetic construct
source               1..20
                     mol_type = protein
                     organism = synthetic construct
SEQUENCE: 317
GGGGSGGGGS GGGGSGGGGS                                                  20

SEQ ID NO: 318       moltype = AA  length = 8
FEATURE              Location/Qualifiers
REGION               1..8
                     note = Synthetic construct
source               1..8
                     mol_type = protein
                     organism = synthetic construct
SEQUENCE: 318
GGSGGGSG                                                                8
```

```
SEQ ID NO: 319          moltype = AA   length = 12
FEATURE                 Location/Qualifiers
REGION                  1..12
                        note = Synthetic construct
source                  1..12
                        mol_type = protein
                        organism = synthetic construct
SEQUENCE: 319
GGSGGGSGGG SG                                                         12

SEQ ID NO: 320          moltype =    length =
SEQUENCE: 320
000

SEQ ID NO: 321          moltype =    length =
SEQUENCE: 321
000

SEQ ID NO: 322          moltype =    length =
SEQUENCE: 322
000

SEQ ID NO: 323          moltype =    length =
SEQUENCE: 323
000

SEQ ID NO: 324          moltype =    length =
SEQUENCE: 324
000

SEQ ID NO: 325          moltype =    length =
SEQUENCE: 325
000

SEQ ID NO: 326          moltype =    length =
SEQUENCE: 326
000

SEQ ID NO: 327          moltype =    length =
SEQUENCE: 327
000

SEQ ID NO: 328          moltype =    length =
SEQUENCE: 328
000

SEQ ID NO: 329          moltype =    length =
SEQUENCE: 329
000

SEQ ID NO: 330          moltype =    length =
SEQUENCE: 330
000

SEQ ID NO: 331          moltype =    length =
SEQUENCE: 331
000

SEQ ID NO: 332          moltype =    length =
SEQUENCE: 332
000

SEQ ID NO: 333          moltype =    length =
SEQUENCE: 333
000

SEQ ID NO: 334          moltype =    length =
SEQUENCE: 334
000

SEQ ID NO: 335          moltype =    length =
SEQUENCE: 335
000

SEQ ID NO: 336          moltype =    length =
SEQUENCE: 336
000

SEQ ID NO: 337          moltype =    length =
```

SEQUENCE: 337
000

SEQ ID NO: 338         moltype =    length =
SEQUENCE: 338
000

SEQ ID NO: 339         moltype =    length =
SEQUENCE: 339
000

SEQ ID NO: 340         moltype =    length =
SEQUENCE: 340
000

SEQ ID NO: 341         moltype =    length =
SEQUENCE: 341
000

SEQ ID NO: 342         moltype =    length =
SEQUENCE: 342
000

SEQ ID NO: 343         moltype =    length =
SEQUENCE: 343
000

SEQ ID NO: 344         moltype =    length =
SEQUENCE: 344
000

SEQ ID NO: 345         moltype =    length =
SEQUENCE: 345
000

SEQ ID NO: 346         moltype =    length =
SEQUENCE: 346
000

SEQ ID NO: 347         moltype =    length =
SEQUENCE: 347
000

SEQ ID NO: 348         moltype =    length =
SEQUENCE: 348
000

SEQ ID NO: 349         moltype =    length =
SEQUENCE: 349
000

SEQ ID NO: 350         moltype =    length =
SEQUENCE: 350
000

SEQ ID NO: 351         moltype =    length =
SEQUENCE: 351
000

SEQ ID NO: 352         moltype =    length =
SEQUENCE: 352
000

SEQ ID NO: 353         moltype =    length =
SEQUENCE: 353
000

SEQ ID NO: 354         moltype =    length =
SEQUENCE: 354
000

SEQ ID NO: 355         moltype =    length =
SEQUENCE: 355
000

SEQ ID NO: 356         moltype =    length =
SEQUENCE: 356
000

| | | |
|---|---|---|
| SEQ ID NO: 357
SEQUENCE: 357
000 | moltype = | length = |
| SEQ ID NO: 358
SEQUENCE: 358
000 | moltype = | length = |
| SEQ ID NO: 359
SEQUENCE: 359
000 | moltype = | length = |
| SEQ ID NO: 360
SEQUENCE: 360
000 | moltype = | length = |
| SEQ ID NO: 361
SEQUENCE: 361
000 | moltype = | length = |
| SEQ ID NO: 362
SEQUENCE: 362
000 | moltype = | length = |
| SEQ ID NO: 363
SEQUENCE: 363
000 | moltype = | length = |
| SEQ ID NO: 364
SEQUENCE: 364
000 | moltype = | length = |
| SEQ ID NO: 365
SEQUENCE: 365
000 | moltype = | length = |
| SEQ ID NO: 366
SEQUENCE: 366
000 | moltype = | length = |
| SEQ ID NO: 367
SEQUENCE: 367
000 | moltype = | length = |
| SEQ ID NO: 368
SEQUENCE: 368
000 | moltype = | length = |
| SEQ ID NO: 369
SEQUENCE: 369
000 | moltype = | length = |
| SEQ ID NO: 370
SEQUENCE: 370
000 | moltype = | length = |
| SEQ ID NO: 371
SEQUENCE: 371
000 | moltype = | length = |
| SEQ ID NO: 372
SEQUENCE: 372
000 | moltype = | length = |
| SEQ ID NO: 373
SEQUENCE: 373
000 | moltype = | length = |
| SEQ ID NO: 374
SEQUENCE: 374
000 | moltype = | length = |
| SEQ ID NO: 375
SEQUENCE: 375
000 | moltype = | length = |
| SEQ ID NO: 376
SEQUENCE: 376
000 | moltype = | length = |

| | | |
|---|---|---|
| SEQ ID NO: 377 SEQUENCE: 377 | moltype = 000 | length = |
| SEQ ID NO: 378 SEQUENCE: 378 | moltype = 000 | length = |
| SEQ ID NO: 379 SEQUENCE: 379 | moltype = 000 | length = |
| SEQ ID NO: 380 SEQUENCE: 380 | moltype = 000 | length = |
| SEQ ID NO: 381 SEQUENCE: 381 | moltype = 000 | length = |
| SEQ ID NO: 382 SEQUENCE: 382 | moltype = 000 | length = |
| SEQ ID NO: 383 SEQUENCE: 383 | moltype = 000 | length = |
| SEQ ID NO: 384 SEQUENCE: 384 | moltype = 000 | length = |
| SEQ ID NO: 385 SEQUENCE: 385 | moltype = 000 | length = |
| SEQ ID NO: 386 SEQUENCE: 386 | moltype = 000 | length = |
| SEQ ID NO: 387 SEQUENCE: 387 | moltype = 000 | length = |
| SEQ ID NO: 388 SEQUENCE: 388 | moltype = 000 | length = |
| SEQ ID NO: 389 SEQUENCE: 389 | moltype = 000 | length = |
| SEQ ID NO: 390 SEQUENCE: 390 | moltype = 000 | length = |
| SEQ ID NO: 391 SEQUENCE: 391 | moltype = 000 | length = |
| SEQ ID NO: 392 SEQUENCE: 392 | moltype = 000 | length = |
| SEQ ID NO: 393 SEQUENCE: 393 | moltype = 000 | length = |
| SEQ ID NO: 394 SEQUENCE: 394 | moltype = 000 | length = |
| SEQ ID NO: 395 SEQUENCE: 395 | moltype = 000 | length = |
| SEQ ID NO: 396 SEQUENCE: 396 | moltype = | length = |

```
000

SEQ ID NO: 397         moltype =    length =
SEQUENCE: 397
000

SEQ ID NO: 398         moltype =    length =
SEQUENCE: 398
000

SEQ ID NO: 399         moltype =    length =
SEQUENCE: 399
000

SEQ ID NO: 400         moltype =    length =
SEQUENCE: 400
000

SEQ ID NO: 401         moltype = AA  length = 10
FEATURE                Location/Qualifiers
REGION                 1..10
                       note = Synthetic
source                 1..10
                       mol_type = protein
                       organism = synthetic construct
SEQUENCE: 401
EPKSCDKTHT                                                                 10

SEQ ID NO: 402         moltype = AA  length = 4
FEATURE                Location/Qualifiers
REGION                 1..4
                       note = Synthetic
source                 1..4
                       mol_type = protein
                       organism = synthetic construct
SEQUENCE: 402
CPPC                                                                        4

SEQ ID NO: 403         moltype = AA  length = 9
FEATURE                Location/Qualifiers
REGION                 1..9
                       note = Synthetic
source                 1..9
                       mol_type = protein
                       organism = synthetic construct
SEQUENCE: 403
PAPELLGGP                                                                   9

SEQ ID NO: 404         moltype = AA  length = 209
FEATURE                Location/Qualifiers
REGION                 1..209
                       note = Synthetic
source                 1..209
                       mol_type = protein
                       organism = synthetic construct
SEQUENCE: 404
SVFLFPPKPK DTLMISRTPE VTCVVVDVSH EDPEVKFNWY VDGVEVHNAK TKPREEQYNS           60
TYRVVSVLTV LHQDWLNGKE YKCKVSNKAL PAPIEKTISK AKGQPREPQV YTLPPSRDEL          120
TKNQVSLTCL VKGFYPSDIA VEWESNGQPE NNYKTTPPVL DSDGSFFLYS KLTVDKSRWQ          180
QGNVFSCSVM HEALHNHYTQ KSLSLSPGK                                            209

SEQ ID NO: 405         moltype = AA  length = 26
FEATURE                Location/Qualifiers
REGION                 1..26
                       note = Synthetic
source                 1..26
                       mol_type = protein
                       organism = synthetic construct
SEQUENCE: 405
EVQLQASGGG FVQPGGSLRL SCAASG                                               26

SEQ ID NO: 406         moltype = AA  length = 19
FEATURE                Location/Qualifiers
REGION                 1..19
                       note = Synthetic
source                 1..19
                       mol_type = protein
                       organism = synthetic construct
SEQUENCE: 406
```

```
MGWFRQAPGK EREFVSAIS                                                            19

SEQ ID NO: 407         moltype = AA  length = 38
FEATURE                Location/Qualifiers
REGION                 1..38
                       note = Synthetic
source                 1..38
                       mol_type = protein
                       organism = synthetic construct
SEQUENCE: 407
YADSVKGRFT ISRDNSKNTV YLQMNSLRAE DTATYYCA                                       38

SEQ ID NO: 408         moltype = AA  length = 12
FEATURE                Location/Qualifiers
REGION                 1..12
                       note = Synthetic
source                 1..12
                       mol_type = protein
                       organism = synthetic construct
SEQUENCE: 408
YWGQGTQVTV SS                                                                   12

SEQ ID NO: 409         moltype = AA  length = 352
FEATURE                Location/Qualifiers
REGION                 1..352
                       note = Synthetic
source                 1..352
                       mol_type = protein
                       organism = synthetic construct
SEQUENCE: 409
EVQLQASGGG FVQPGGSLRL SCAASGFAYS IDIMGWFRQA PGKEREFVSA ISSWRGGPSK    60
YADSVKGRFT ISRDNSKNTV YLQMNSLRAE DTATYYCALT VDKGGSIYWG QGTQVTVSSA    120
EPKSCDKTHT CPPCPAPELL GGPSVFLFPP KPKDTLMISR TPEVTCVVVD VSHEDPEVKF    180
NWYVDGVEVH NAKTKPREEQ YNSTYRVVSV LTVLHQDWLN GKEYKCKVSN KALPAPIEKT    240
ISKAKGQPRE PQVYTLPPSR DELTKNQVSL TCLVKGFYPS DIAVEWESNG QPENNYKTTP    300
PVLDSDGSFF LYSKLTVDKS RWQQGNVFSC SVMHEALHNH YTQKSLSLSP GK            352
```